(12) United States Patent
Costa Fejoz et al.

(10) Patent No.: US 11,608,509 B2
(45) Date of Patent: Mar. 21, 2023

(54) NIPAH VIRUS ENVELOPE GLYCOPROTEIN PSEUDOTYPED LENTIVIRUS

(71) Applicants: Ecole Normale Superieure de Lyon, Lyons (FR); Centre National de la Recherche Scientifique (CNRS), Paris (FR); Université Claude Bernard Lyon 1, Villeurbanne (FR); Institut National de la Sante et de la Recherche Medicale (INSERM), Paris (FR)

(72) Inventors: Caroline Costa Fejoz, Lyons (FR); Els Verhoeyen, Nice (FR); François-Loïc Cosset, Lyons (FR); Ruben Bender, Frankfurt (DE); Christian Buchholz, Frankfurt (DE); Qi Zhou, Hitchin (GB)

(73) Assignees: Ecole Normale Superieure de Lyon, Lyons (FR); Centre National de la Recherche Scientifique (CNRS), Paris (FR); Université Claude Bernard Lyon 1, Villeurbanne (FR); Institut National de la Sante et de la Recherche Medicale (INSERM), Paris (FR)

( * ) Notice: Subject to any disclaimer, the term of this patent is extended or adjusted under 35 U.S.C. 154(b) by 773 days.

(21) Appl. No.: 16/094,636

(22) PCT Filed: Apr. 20, 2017

(86) PCT No.: PCT/EP2017/059435
§ 371 (c)(1),
(2) Date: Oct. 18, 2018

(87) PCT Pub. No.: WO2017/182585
PCT Pub. Date: Oct. 26, 2017

(65) Prior Publication Data
US 2019/0144885 A1    May 16, 2019

(30) Foreign Application Priority Data

Apr. 21, 2016    (EP) .................................... 16305468

(51) Int. Cl.
| C12N 15/86 | (2006.01) |
| A61P 35/00 | (2006.01) |
| C07K 14/005 | (2006.01) |
| C07K 14/54 | (2006.01) |
| C07K 16/28 | (2006.01) |
| C07K 16/32 | (2006.01) |
| A61K 39/00 | (2006.01) |

(52) U.S. Cl.
CPC ............. *C12N 15/86* (2013.01); *A61P 35/00* (2018.01); *C07K 14/005* (2013.01); *C07K 14/5418* (2013.01); *C07K 16/2812* (2013.01); *C07K 16/2815* (2013.01); *C07K 16/32* (2013.01); *A61K 2039/505* (2013.01); *C07K 2317/622* (2013.01); *C07K 2319/03* (2013.01); *C07K 2319/30* (2013.01); *C07K 2319/74* (2013.01); *C12N 2740/16043* (2013.01); *C12N 2740/16045* (2013.01); *C12N 2760/18222* (2013.01); *C12N 2760/18422* (2013.01)

(58) Field of Classification Search
None
See application file for complete search history.

(56) References Cited

U.S. PATENT DOCUMENTS

| 6,896,881 | B1 * | 5/2005 | Russell ................. C07K 14/485 424/192.1 |
| 9,486,539 | B2 | 11/2016 | Lee et al. |
| 10,064,958 | B2 | 9/2018 | Lee et al. |
| 2003/0207445 | A1 | 11/2003 | Schauber et al. |
| 2005/0070493 | A1 | 3/2005 | Fawell et al. |
| 2007/0031455 | A1 | 8/2007 | Audonnet |
| 2009/0041724 | A1 | 2/2009 | Steen et al. |
| 2017/0165348 | A1 | 6/2017 | Cantore et al. |
| 2019/0125898 | A1 | 5/2019 | Lee et al. |
| 2020/0060980 | A1 | 2/2020 | Von Maltzahn et al. |
| 2021/0137839 | A1 | 5/2021 | Von Maltzahn et al. |
| 2021/0187018 | A1 | 6/2021 | Von Maltzahn et al. |

(Continued)

FOREIGN PATENT DOCUMENTS

| EP | 1115879 | 7/2001 |
| EP | 2615176 | 1/2012 |

(Continued)

OTHER PUBLICATIONS

Smith (FEBS Journal, 276: 1-11, 2009) (Year: 2009).*

(Continued)

*Primary Examiner* — Anoop K Singh
*Assistant Examiner* — Magdalene K Sgagias
(74) *Attorney, Agent, or Firm* — Morrison & Foerster LLP

(57) ABSTRACT

The present invention relates to pseudotyped retrovirus-like particles or retroviral vectors comprising both engineered envelope glycoproteins derived from a virus of the Paramyxoviridae family fused to a cell targeting domain and fused to a functional domain. The present invention also relates to the use of said pseudotyped retrovirus-like particles or retroviral vectors to selectively modulate the activity of specific subsets of cells, in particular of specific immune cells. These pseudotyped retrovirus-like particles or retroviral vectors are particularly useful for gene therapy, immune therapy and/or vaccination.

10 Claims, 13 Drawing Sheets
Specification includes a Sequence Listing.

(56) References Cited

U.S. PATENT DOCUMENTS

| | | |
|---|---|---|
| 2021/0198698 A1 | 7/2021 | Von Maltzahn et al. |
| 2021/0228627 A1 | 7/2021 | Von Maltzahn et al. |

FOREIGN PATENT DOCUMENTS

| | | | | |
|---|---|---|---|---|
| EP | 2 615 176 | 7/2013 | | |
| WO | WO 2001/074861 | 10/2001 | | |
| WO | WO 2006/028786 | 3/2006 | | |
| WO | WO 2006/059141 | 6/2006 | | |
| WO | WO 2007/005244 | 1/2007 | | |
| WO | WO 2006/078221 | 7/2007 | | |
| WO | WO 2008/037458 | 4/2008 | | |
| WO | WO-2008037458 A2 * | 4/2008 | ............. | A61P 31/18 |
| WO | WO 2008/071959 | 6/2008 | | |
| WO | WO 2008/115199 | 11/2008 | | |
| WO | WO 2009/130208 | 10/2009 | | |
| WO | WO 2010/053489 | 5/2010 | | |
| WO | WO 2011/011584 | 1/2011 | | |
| WO | WO 2011/058052 | 5/2011 | | |
| WO | WO 2012/095535 | 7/2012 | | |
| WO | WO 2012/149376 | 11/2012 | | |
| WO | WO 2013/084000 | 6/2013 | | |
| WO | WO 2013/148327 | 10/2013 | | |
| WO | WO 2014/076137 | 5/2014 | | |
| WO | WO 2014/164553 | 10/2014 | | |
| WO | WO 2015/011478 | 1/2015 | | |
| WO | WO 2015/110957 | 7/2015 | | |
| WO | WO 2016/138525 | 9/2016 | | |
| WO | WO 2016/183482 | 11/2016 | | |
| WO | WO 2017/151717 | 9/2017 | | |
| WO | WO 2017/173034 | 10/2017 | | |
| WO | WO 2017/182585 | 10/2017 | | |
| WO | WO 2017/165245 | 11/2017 | | |
| WO | WO 2017/211945 | 12/2017 | | |
| WO | WO 2018/009923 | 1/2018 | | |
| WO | WO 2018/129563 | 1/2018 | | |
| WO | WO 2018/022749 | 2/2018 | | |
| WO | WO 2018/208728 | 11/2018 | | |
| WO | WO 2019/152692 | 1/2019 | | |
| WO | WO 2019/222403 | 5/2019 | | |
| WO | WO 2019/113512 | 6/2019 | | |
| WO | WO 2019/161281 | 8/2019 | | |
| WO | WO 2020/014209 | 1/2020 | | |
| WO | WO 2020/102485 | 5/2020 | | |
| WO | WO 2020/102499 | 5/2020 | | |
| WO | WO 2020/102503 | 5/2020 | | |
| WO | WO 2020/102578 | 5/2020 | | |

OTHER PUBLICATIONS

Moll (Journal of Virology 76(14): 7174-7186, 2002) (Year: 2002).*
Plemper (PLoS Pathogens, 7(6): 1-6, 2011) (Year: 2011).*
Aguilar et al., "Polybasic KKR Motif in the Cytoplasmic Tail of Nipah Virus Fusion Protein Modulates Membrane Fusion by Inside-Out Signaling," J Virol (2007) 81:4520-4532.
Bender et al., "Receptor-Targeted Nipah Virus Glycoproteins Improve Cell-Type Selective Gene Delivery and Reveal a Preference for Membrane-Proximal Cell Attachment," PLOS Pathogens 12(6):e1005641.
Bishop et al., "Identification of Hendra Virus G Glycoprotein Residues That Are Critical for Receptor Binding," J Virol (2007) 81:5893-5901.

Bowden et al., "Structural basis of Nipah and Hendra virus attachment to their cell-surface receptor ephrin-B2," Nature Structural & Molecular Biology (2008) 15(6):567-572.

Guillaume et al., "Evidence of a Potential Receptor-Binding Site on the Nipah Virus G Protein (NiV-G): Identification of Globular Head Residues with a Role in Fusion Promotion and Their Localization on an NiV-G Structural Model," J Virol (2006) 80:7546-7554.

Khetawat et al., "A Functional Henipavirus Envelope Glycoprotein Pseudotyped Lentivirus Assay System," Khetawat and Broder Virology Journal (2010) 7:312.

Levy et al., "Surface engineering of lentiviral vectors for gene transfer into gene therapy target cells," Current Opinion in Pharmacology (2015) 24:79-85.

Munch et al., "Off-target-free gene delivery by affinity-purified receptor-targeted viral vectors," Nature Communications (2015) 6:6246.

Negrete et al., "Single Amino Acid Changes in the Nipah and Hendra Virus Attachment Glycoproteins Distinguish EphrinB2 from EphrinB3 Usage," J Virol (2007) 81(19):10804-10814.

Palomares et al., "Nipah Virus Envelope-Pseudotyped Lentiviruses Efficiently Target ephrinB2-Positive Stem Cell Populations In Vitro and Bypass the Liver Sink When Administered In Vivo," J Virol (2013) 87:2094-2108.

Steffen et al., "Henipavirus mediated membrane fusion, virus entry and targeted therapeutics," Viruses (2012) 4:280-309.

Verhoeyen et al., "Lentiviral vector gene transfer into human T cells," Methods in Mol Biol (2009) 506:97-114.

Witting S.R. et al., Characterization of a 3rd Generation Lentiviral Vector Pseudotyped With Nipah Virus Envelope Proteins For Endothelial Cell Transduction. Gene Ther, May 23, 2013, vol. 20, No. 10.

Xu et al., "Host cell recognition by the henipaviruses: Crystal structures of the Nipah G attachment glycoprotein and its complex with ephrin-B3," PNAS (2008) 105(29):9953-9958.

Xu et al., "New Insights into the Hendra Virus Attachment and Entry Process from Structures of the Virus G Glycoprotein and Its Complex with Ephrin-B2," PLOS One (2012) 7(11):e48742.

Zhou et al., "Cell type specific gene delivery by lentiviral vectors," Onco Immunolgy (2013) 2:e22566.

Zhou Q et al. T cell receptor gene transfer exclusively to human CD8 cells enhances tumor killing. Blood Aug. 16, 2012, vol. 120 No 22:4334.

Anliker et al., *Specific gene transfer to neurons, endothelial cells and hematopoietic progenitors with lentiviral vectors*, 7(11) Nature Methods 929-937 (Nov. 2010).

Enkirch et al., *Targeted lentiviral vectors pseudotyped with the Tupaia paramyxovirus glycoproteins*, 20(1) Gene Therapy 16-23(2013).

Frecha et al., *Stable transduction of quiescent T cells without induction of cycle progression by a novel lentiviral vector pseudotyped with measles virus glycoproteins*, 112(13) Blood 4843-4852 (Dec. 15, 2008).

Funke et al., *Targeted Cell Entry of Lentiviral Vectors*, 16(8) Molecular Therapy 1427-1436 (Aug. 2008).

Imamura et al., *Autonomous growth and increased cytotoxicity of natural killer cells expressing membrane-bound interleukin-15*, 124(7) Blood 1081-1088 (Aug. 2014).

Kneissl et al., *Measles Virus Glycoprotein-Based Lentiviral Targeting Vectors That Avoid Neutralizing Antibodies*, 7(10) Plos One 1-8 (Oct. 2012).

Münch et al., *DARPins: An Efficient Targeting Domain for Lentiviral Vectors*, 19(4) Molecular Therapy 686-693 (2011).

Needleman et al., *A General Method Applicable to the Search for Similarities in the Amino Acid Sequence of Two Proteins*, 48 J. Mol. Biol. 443-453 (1970).

Verhoeyen et al., *IL-7 surface-engineered lentiviral vectors promote survival and efficient gene transfer in resting primary T lymphocytes*, 101 (6) Blood 2167-2174 (Mar. 15, 2003).

Zhou et al., *Exclusive Transduction of Human CD4$^+$ T Cells upon Systemic Delivery of CD4-Targeted Lentiviral Vectors*, 195(5) J. Immunol. 2493-2501 (2015).

International Search Report dated Jun. 13, 2017, in corresponding PCT Application No. PCT/EP2017/059435.

European Search Report dated Oct. 11, 2016, in corresponding EP Patent Application No. 16 30 5468.

Abengozar et al., "Blocking ephrinB2 with highly specific antibodies inhibits angiogenesis, lymphangiogenesis, and tumor growth". Blood 119(19):4565-76, 2012.

Aguilar et al. "N-glycans on nipah virus fusion protein protect against neutrilization but reduce membrane fusion and viral entry", Virol. (80) 4878-4889, 2006.

Alam et al., "Coexpression of EphB4 and ephrinB2 in tumor advancement of uterine cervical cancers", Gynecologic Oncology 114(1):84-88, 2009.

(56) References Cited

OTHER PUBLICATIONS

Barile et al., "Exosomes: Therapy delivery tools and biomarkers of diseases," Pharmacol Ther. (2017) 174: 63-78.
Bender et al., "Developing an Engineered Nipah Virus Glycoprotein Based Lentiviral Vector System Retargeted To Cell Surface Receptors of Choice," Mol. Ther. (2015) 23(1); S2.
Biering et al. "N-glycans on the nipah virus attachment glycoprotein modulate fusion and viral entry as they protect against antibody neutrilization" J Virol. (2012) 86(22): 11991-12002.
Chiriaco et al., "Dual-regulated lentiviral vector for gene therapy of X linked chronic granulomatosis." Molecular Therapy (2014) 22(8): 1472-1483.
Field et al.,"Comparison of lentiviral and sleeping beauty mediated alpha&bgr T cell receptor gene transfer." Plos One (2013) 8(6): e68201.
Friedel et al., "Receptor-targeted lentiviral vectors are exceptionally sensitive toward the biophysical properties of the displayed single-chain Fv," Protein Eng Des Sel. (2015) 28(4): 93-106. doi: 10.1093/protein/gzv005.
Haga et al.."Permanent, lowered HLA class I expression using lentivirus vectors with shRNA constructs: averting cytotoxicity by alloreactive T lymphocytes." Transplantation Proceedings (2006) 38(10):3184-3188.
Lattanzi et al. "A Strategy of antigen incoperation into exosomes: Comparing cross-presentation levels of antigens delivered by engineered exosomes and by lentiviral virus-like particles", Vaccine (2012) col. 20, No. 50; 7229.
Leavitt et al., "Concordant modulation of neutrilization resistance and high infectivity of the primary human immunodeficiency virus type 1 MN strain and definition of a potential gp41 binding site in gp120". Journal of Virology 560-570, 2003.
Lee et al. "Modes of paramyxovirus fusion: a Henipavirus perspective" 2011. Trends in Microbiology.Aug.;19(8):389-99.
Lentz et al. "Review, viral vectors for gene delivery to the central nervous system" Neurobiology of Disease 48:179-188, 2012.
Milani et al., "Genome editing for scalable produciton of alloantigen free lentiviral vectors for in vivo gene therapy." EMBO Molecular Medicine (2017) 9(11): 1558-1573.
Montagna et al., "VSV-G-Enveloped Vesicles for Traceless Delivery of CRISPR-Cas9" Mol Ther Nucleic Acids. (2018) 12:453-462.
Morizono et al., "Redirecting lentiviral vectors pseudotyped with sinbis virus-derived envelope proteins to DC-SIGN by modificiation of N-linked glycans of envelope proteins," J Virol. (2010) 84(14): 6923-34.
Nakamura et al., "Antibody-targeted cell fusion," Nat Biotechnol. (2004) 22(3): 331-336.
Negrete et al., "EphrinB2 is the entry receptor for Nipah virus, an emergent deadly paramyxovirus", Nature (436)401-405, 2005.
Nordlund et al.,"SNARE-fusion mediated insertion of membrane proteins into native and artificial membranes." Nat Commun. (2014) 5: 4303.
Pichard et al., "Specific Micro-RNA regulated TetR-KRAB Transcriptional control of transgene expression in viral vector transduced cells," Plos One (2012) 7(12):e51952.
Riazifar et al., "Stem Cell Extracellular Vesicles: Extended Messages of Regeneration," Annu Rev Pharmacol Toxicol. (2017) 57: 125-154.
Schauber-Plewa et al., "Complement regulatory proteins are incorporated into lentiviral vectors and protect particles against complement inactivation." Gene Therapy. (2004) 12(3): 238-245.
Sosale et al., "Marker of self: CD47 on lentiviral vectors decreases macrophage-mediated clearance and increases delivery to SIRPA-expressing lung carcinoma tumors." Molecular Therapy (2016) 3(7): 16080.
Stefan et al., "DARPins recognizing the tumor-associated antigen EpCAM selected by phage and ribosome display and engineered for multivalency," J Mol Biol. (2011) 413(4): 826-43.
Tang et al., "Therapeutic potential of CAR-T cell-derived exosomes: a cell-free modality for targeted cancer therapy." Oncotarget (2015) 6(42); 44179-44190.
Tomas et al., "Improved GaLV-TR glycoproteins to pseudotype lentiviral vectors: impact of viral protease activity in the production of LV pseudotypes." Molecular Therapy (2019) 15: 1-8.
Weiss et al., "Review, The blood-brain barrier in brain homeostasis and neurological diseases" Biochimica Biophys Acta. (2009) 1788: 841-857.
White et al., "Structures and mechanisms of viral membrane fusion proteins: multiple variations on a common theme," Crit Rev Biochem Mol Biol. (2008) 43(3): 189-219.
Yang et al., "Virus-mimetic fusogenic exosomes for direct delivery of integral membrane proteins to target cell membranes." Advanced Materials (2017) 29(13): 1605604.
Zakaria et al., "Combination of hepatocyte specific delivery and transformation dependent expression of shRNA inducing transcriptional gene silencing of c-Myc promoter in hepatocellular carcinoma cells", BMC Cancer, Biomed Central, London (2014) 14(1): 582.
Zhang et al., "Cell specific targeting of lentiviral vector mediated by fusion proteins derived from Sindbis virus, vesicular stomatitis virus, or avian sarcoma/leukosis virus", Retrovirology 7(3) 1-15, 2010.

* cited by examiner

FIG.10

NIPAH VIRUS ENVELOPE GLYCOPROTEIN PSEUDOTYPED LENTIVIRUS

CROSS-REFERENCE TO RELATED APPLICATIONS

This application is a U.S. National Stage Application pursuant to 35 U.S.C. § 371 of International Patent Application PCT/EP2017/059435, filed on Apr. 20, 2017, and published as WO 2017/182585 on Oct. 26, 2017, which claims priority to European Patent Application 16305468.7, filed on Apr. 21, 2016, all of which are incorporated herein by reference in their entireties for all purposes.

FIELD OF THE INVENTION

The present invention relates to methods for selectively modulating the activity of distinct subtypes of cells.

BACKGROUND

Cells of the immune system are involved in many types of pathologies. Enhancing or reducing their activity is therefore in focus of many therapeutic strategies. Many types of immune cells with very distinct functions can be distinguished by the expression of certain cell surface proteins. There is so far no technology available that allows the selective activation or deactivation of only a distinct cell subtype, especially in vivo.

The use of cytokines to induce or promote the generation of a desirable immune response is an attractive approach in immune therapy against cancer. Cytokines are typically used as unspecific auxiliary substances to support other immune therapies or are administered additionally to chemotherapy. But up to now, the cytokine-based treatments are rarely used because of unsolved systemic toxicity. Besides, cytokines are usually applied systemically, thereby hitting all cell types expressing the relevant cytokine receptor. A fine tuned modulation at the disease relevant site is therefore not possible.

To overcome this drawback, cytokines may be fused to an anti-tumor antibody or connected to micro- or nano-particles with an anti-tumor antibody, thereby targeting the cytokines to the tumor and reducing the systemic side effects. However, these fusion proteins or cytokine-antibody loaded particles are less stable and cleared fast in vivo, leading to a relative low cytokine concentration at the disease sites. In addition, the release of the cytokines by cytokine-antibody loaded particles is dependent on pH. Moreover, cytokines (such as IL-2) delivered to the tumor by these previous approaches non-selectively stimulate various types of different immune cells in the complicated tumor microenvironment, including both immune effective and suppressive cells, thus limiting their applications for cancer treatment.

With respect to gene therapy, important target cells such as resting human T cells, B cells and HSCs (hematopoietic stem cells) are refractory to transduction with lentiviral vectors. The transduction mediated by conventional VSV-LV occurs only when T cells have been activated. In the gene therapy trials performed to date, T cells have been activated via cognate antigen receptors, which usually induce phenotypic and functional changes in T cells and eventually lead to a reduced T cell persistence and anti-tumor effect in vivo.

To promote gene transfer in resting T cells, several chimeric lentiviral vectors have been generated. For example, Verhoeyen et al. (*Blood*, 2003, vol. 101, n° 6) disclose HIV-derived vectors pseudotyped with two types of envelope glycoproteins: a chimeric MLV (Murine Leukemia Virus) envelope glycoprotein (gp) N-terminally fused to IL-7 and VSV-G (Vesicular Stomatitis Virus glycoprotein). These IL-7 vector particles can efficiently transduce resting T cells and induce T cell activation, but equally transduce CD4+ and CD8+ T cells. Thus, they cannot discriminate between the different T cells subsets. Moreover, the fact that a non-targeted envelope gp, such as VSV-G gp, is needed will possibly allow transduction of unwanted hematopoietic or endothelial cells. One exception is measles virus (MeV) glycoprotein pseudotyped lentiviral vectors (MV-LV). MV-LV can mediate the transduction of resting T lymphocytes without changing the G0/G1a cell cycle status. Zhou et al. (*J Immunol*, 2015, vol. 195, n° 5) also disclose that CD4-targeted LV can transduce freshly isolated resting T cells, but with very low efficiency (less than 10%) at high particle dose.

Finally, current strategies for generating less differentiated tumor specific T cells for adoptive T cell therapy rely on optimizing the T cell stimulation and cultivation protocol. For example, to produce more $T_{SCM}$ cells (Stem memory T cells) or $T_{CM}$ cells (Central memory T cells), combinations of IL-15 and IL-7 or IL-21 and IL-7 are used for T cell stimulation and expansion. This cultivation system is very expensive since routine cytokine re-supplement (every two days) is required. Afterwards, several cell sorting steps are usually implemented to obtain the desirable cell types.

There is therefore still a need to provide methods for selectively and efficiently modulating the activity of distinct subtypes of immune cells.

DESCRIPTION OF THE INVENTION

The Inventors have surprisingly found that it is possible to selectively modulate the activity of distinct subtypes of immune cells by using pseudotyped retrovirus-like particles or retroviral vectors (for example lentivirus-like particles (VLP) or lentiviral vectors (LV)) carrying both a cell-specific targeting domain (for example specific for CD4+ T cells or for CD8+ T cells) and a functional domain, for example a cytokine, that are each fused to a glycoprotein of a virus of the Paramyxoviridae family. Said retroviral vectors also specifically and efficiently deliver a packaged gene into the targeted cells.

As a matter of fact, it was unexpectedly found that combining a functional domain with a cell-specific targeting domain on pseudotyped retrovirus-like particles or retroviral vectors greatly improved the selective activity modulation of the targeted subtypes of immune cells by comparison to the corresponding particles or vectors comprising only the cell-specific targeting domain.

For example, the Inventors have shown that stimulatory cytokine-displaying T cell targeted particles selectively activate the targeted T cell subsets in cultures of the mixed cell types and in vivo in a human blood system mouse model and also deliver the packaged gene into the targeted T cell subtype, without any need for stimulatory culture conditions. IL-7 (Interleukin-7)-displaying CD4-targeted particles based on MeV (measles virus) glycoproteins ($4^H$/IL$7^H$-VLP) indeed specifically activate and promote the survival of cultivated primary CD4+ cells, whereas IL7-displaying CD8-targeted particles based on NiV (Nipah virus) glycoproteins ($8^G$/IL$7^G$-VLP) selectively activate and promote the survival of CD8+ T cells. Besides, $4^H$/IL$7^H$-LV efficiently and specifically delivers GFP transgenes into CD4+ T cells in the cell mixture, in a dose-dependent manner. Compared to the parental CD4-targeted LV (not co-displaying IL-7), $4^H/IL7^H$-LV is more efficient in delivering the therapeutic ErbB2CAR transgene selectively into resting CD4+ T cells. Similar exclusive gene transfer and stimulation of CD8+ T cells has also been observed with the CD8/IL-7 co-displaying NiV glycoprotein pseudotyped lentiviral vectors ($8^G/IL7^G$-LV). Indeed, 8G/IL7G-LV is more efficient in selective CD8+ T cell activation and targeted gene delivery than $8^G$-LV (see examples).

The retrovirus-like particle and retroviral vector according to the invention present many advantages, such as:
- providing a high local concentration of cytokines at the cell target sites, thereby improving the efficiency and preventing severe side-effects of cytokine therapy,
- providing a more stable and constant stimulation of the target cells compared to soluble cytokines, thereby improving the efficiency of cytokine therapy,
- providing a very flexible system allowing to combine different types of cytokines and different types of targeting domains on a single particle or retroviral vector,
- allowing coupling of cell stimulation with cell-specific gene transfer in vitro or in vivo, which results in a more efficient transduction of the specific resting T cell subsets,
- allowing coupling of a T cell phenotype induction with gene transfer in vitro or in vivo, due to the interaction with the displayed cytokines on the particle or vector surface, the differentiation of the transduced cells being controlled, and more generally:
- allowing delivery of biological material and/or therapeutic drug(s), including but not limited to gene, mRNA, shRNA, microRNA, peptide, protein, protein fragment and theirs combinations to specific cells or subset of cells, in vitro or in vivo, p1 allowing an easier cell manufacturing process (for example T cell or hematopoietic cell manufacturing process) for adoptive therapy,
- preventing problems of resistance in vivo when using retrovirus-like particle or retroviral vector pseudotyped with glycoproteins from Nipah virus, thanks to low pre-existing antibodies in human beings.

The present invention thus relates to a pseudotyped retrovirus-like particle or retroviral vector comprising:
a) at least one cell targeting fusion protein comprising (i) a protein derived from an envelope glycoprotein G or H of a virus of the Paramyxoviridae family, said protein preferably lacking at least one part of the cytoplasmic region of said envelope glycoprotein G or H and being preferably at least partially unable to bind at least one natural receptor of said envelope glycoprotein G or H, or a transmembrane domain and (ii) at least one cell targeting domain,
b) at least one modulating fusion protein comprising (i) a protein derived from an envelope glycoprotein G or H of a virus of the Paramyxoviridae family, said protein preferably lacking at least one part of the cytoplasmic region of said envelope glycoprotein G or H and being preferably at least partially unable to bind at least one natural receptor of said envelope glycoprotein G or H, or a transmembrane domain and (ii) at least one functional domain, and
c) at least one glycoprotein derived from an envelope glycoprotein F of a virus of the Paramyxoviridae family and preferably lacking at least one part of the cytoplasmic region of said envelope glycoprotein F,
wherein said cell targeting fusion protein and/or said modulating fusion protein comprises a protein derived from an envelope glycoprotein G or H of a virus of the Paramyxoviridae family.

Said virus of the Paramyxoviridae family may be a virus of the *Morbillivirus* genus, for example selected in the group consisting of measles virus (MeV), canine distemper virus, Cetacean morbillivirus, Peste-des-petits-ruminants virus, Phocine distemper virus, and Rinderpest virus, or a virus of the *Henipavirus* genus, for example selected in the group consisting of Nipah virus (NiV), Cedar virus and Hendra virus.

The protein of a) and/or b) preferably comprises at least two mutations by comparison to the sequence of said envelope glycoprotein G or H, said at least two mutations resulting in the at least partially inability to bind at least one natural receptor of said envelope glycoprotein G or H.

Said cell targeting domain may be selected in the group consisting of a DARPin, a scFv, targeting peptide and their combinations and/or said functional domain may be selected in the group consisting of a cytokine, growth factor, hormone, neurotransmitter, apoptosis ligand and their combinations.

The target cells may be selected in the group consisting of cells of the hematopoietic system (including T cells, B cells, monocytes, Th1 cells, Th2 cells, Treg cells, mast cells, dendritic cells (DCs), natural killer (NK) cells, natural killer T (NKT) cells, macrophages, hematopoietic stem cells, progenitor T and/or B cells, erythroblasts, platelets and/or neutrophils), stroma cells, endothelial cells, liver cells, muscle cells, cells of the nervous system, diseased cells and their combinations.

The present invention also relates to the use of a pseudotyped retrovirus-like particle or retroviral vector as defined above, to selectively modulate the activity of target cells and/or selectively transduce target cells, the target cells being for example as defined above.

The present invention also relates to a method for selectively modulating the activity of target cells and/or selectively transducing target cells, wherein said method comprises contacting a pseudotyped retrovirus-like particle or retroviral vector as defined above with cells comprising said target cells, the target cells being for example as defined above.

The present invention also relates to a pseudotyped retrovirus-like particle or retroviral vector as defined above for use as a medicament, preferably in immune therapy gene therapy and/or vaccination, for example in the prevention and/or treatment of an immune disease (for example an auto-immune disease), cancer, genetic disease, allergic disease, inflammatory disease, infectious disease, metabolic disease, neurological disease (for example, neural dystrophy, Parkinson disease, Huntington disease, Alzheimer disease), muscular disease and their combinations.

The present invention also relates to a nucleic acid comprising a sequence encoding a cell targeting fusion protein and/or a sequence encoding a modulating fusion protein, wherein:
said cell targeting fusion protein comprises a protein derived from an envelope glycoprotein G or H of a virus of the Paramyxoviridae family or a transmembrane domain and (ii) at least one cell targeting domain, and
said modulating fusion protein comprises (i) a protein derived from an envelope glycoprotein G or H of a virus of the Paramyxoviridae family or a transmembrane domain and (ii) at least one functional domain.

The present invention also relates to a vector comprising a nucleic acid as defined above.

The present invention also relates to a method for producing a pseudotyped retrovirus-like particle or retroviral vector as defined above, wherein said method comprises co-transfecting a packaging cell line with:

(i) at least one nucleic acid encoding a cell targeting fusion protein, said cell targeting fusion protein comprising (i) a protein derived from an envelope glycoprotein G or H of a virus of the Paramyxoviridae family or a transmembrane domain and (ii) at least one cell targeting domain, (ii) at least one nucleic acid encoding a modulating fusion protein, said modulating fusion protein comprising (i) a protein derived from an envelope glycoprotein G or H of a virus of the Paramyxoviridae family or a transmembrane domain and (ii) at least one functional domain, (iii) at least one nucleic acid encoding a glycoprotein derived from an envelope glycoprotein F of a virus of the Paramyxoviridae family, (iv) at least one vector comprising a nucleic acid encoding core proteins from said retrovirus and (v) optionally, at least one vector comprising a packaging competent retroviral derived genome, wherein said cell targeting fusion protein and/or said modulating fusion protein comprises a protein derived from an envelope glycoprotein G or H of a virus of the Paramyxoviridae family.

Pseudotyped Retrovirus-Like Particle or Retroviral Vector

A "retrovirus-like particle" as used herein refers to a particle comprising retroviral proteins Gag, Pol and Env (envelope), but not comprising any retrovirus derived genetic information.

The Gag, Pol and Env proteins are derived from the retrovirus and are provided in trans by means of a packaging cell line.

As used herein, a "retroviral vector" comprises the Gag, Pol and Env (Envelope) proteins and a RNA molecule. Said RNA molecule does not contain any gag, env or pol gene, but comprises the psi element and LTRs which are required for an effective packaging of the RNA molecule into the resulting particles. Said RNA molecule may further comprise a gene of interest that is under the control of a suitable promoter and is thus expressed upon integration of said gene into the genome of the host or target cell.

A retrovirus-like particle or retroviral vector is a virus-like particle or viral vector, respectively, whose core proteins, i.e. the proteins encoded by the Gag and Pol genes, are derived from a retrovirus.

By the term "retrovirus", it is herein meant a virus whose genome consists of a RNA molecule and that comprises a reverse-transcriptase.

A retrovirus is a member of the Retroviridae family. The retrovirus may be an Oncovirus, Lentivirus or Spumavirus.

The oncovirus may be an alpharetrovirus, a betaretrovirus, a deltaretrovirus, an epsilonretrovirus or a gammaretrovirus.

When the retrovirus is an oncovirus, said retrovirus may be MLV (Murine leukemia virus), ASV (Avian sarcoma virus), Feline leukemia virus, Bovine leukemia virus, RSV (Rous sarcoma virus), MPMV (Mason-Pfizer monkey virus), HTLV I (Human T-cell leukemia virus-I) or HTLV II (Human T-cell leukemia virus-II).

When the retrovirus is a lentivirus, said retrovirus may be HIV (Human Immunodeficiency Virus), preferably HIV-1 or HIV-2, SIV (Simian Immunodeficiency Virus), EIAV (Equine Infectious Anemia Virus), FIV (Feline Immunodeficiency Virus) or CAEV (Caprine Arthritis Encephalitis Virus).

When the retrovirus is a spumavirus, said retrovirus may be HFV (Human Foamy Virus).

For example, the retroviral vector may be a lentiviral vector, an alpha retroviral vector, a murine retroviral vector or a FIV vector.

Genomes of such retroviruses are readily available in gene databases.

In a preferred embodiment, said retrovirus is a lentivirus, more preferably HIV, such as HIV-1 or HIV-2.

The present invention thus preferably relates to a lentivirus like particle (LVP) or a lentiviral vector (LV), preferably a HIV-derived LVP or LV.

The term "pseudotyped" in the expression "pseudotyped retrovirus-like particle or retroviral vector" herein means that the retrovirus-like particle or retroviral vector bears envelope glycoproteins that are derived from at least another virus than said retrovirus and/or that are engineered envelope glycoproteins, for example chimeric and/or mutated envelope glycoproteins.

The retrovirus-like particle or retroviral vector according to the invention is for example pseudotyped with engineered glycoproteins derived from a virus of the Paramyxoviridae family, preferably from a virus of the *Morbillivirus* genus or of the *Henipavirus* genus glycoproteins, as detailed below.

Envelope Glycoproteins of the Paramyxoviridae Family

The modified envelope glycoproteins used for pseudotyping the retrovirus-like particle or retroviral vector according to the invention are derived from envelope glycoproteins of a virus of the Paramyxoviridae family.

The virus of the Paramyxoviridae family is preferably a virus of the *Morbillivirus* genus or of the *Henipavirus* genus.

The viruses of the *Morbillivirus* genus and of the *Henipavirus* genus use two types of glycoproteins to enter into a target cell: an attachment protein (called glycoprotein G in a virus of the *Henipavirus* genus or glycoprotein H in a virus of the *Morbillivirus* genus) and a glycoprotein F (also called fusion protein or protein F). The protein F mediates the fusion of viral membranes with the cellular membranes of the host cell. The glycoprotein G/H recognizes the receptor on the target membrane and supports the F protein in its membrane fusion function. Both glycoprotein G/H and glycoprotein F are used in a modified form for pseudotyping the retrovirus-like particle or retroviral vector according to the invention.

A virus of the *Morbillivirus* genus is for example selected in the group consisting of measles virus, Canine distemper virus, Cetacean morbillivirus, Peste-des-petits-ruminants virus, Phocine distemper virus and Rinderpest virus.

A preferred virus of the *Morbillivirus* genus is a measles virus (MeV).

A virus of the *Henipavirus* genus is for example selected in the group consisting of Nipah virus, Cedar virus and Hendra virus.

A preferred virus of the *Henipavirus* genus is a Nipah virus (NiV).

In a preferred embodiment, the modified enveloped glycoproteins are derived from the envelope glycoprotein H and the glycoprotein F of a measles virus or from the envelope glycoprotein G and the glycoprotein F of a Nipah virus.

An example of sequence of Nipah virus envelope glycoprotein G is sequence SEQ ID NO: 9.

An example of sequence of Nipah virus envelope glycoprotein F is sequence SEQ ID NO: 11.

An example of sequence of measles virus envelope glycoprotein H (called glycoprotein H) is sequence SEQ ID NO: 10.

An example of sequence of measles virus envelope glycoprotein F is sequence SEQ ID NO: 12.

Protein Derived from an Envelope Glycoprotein G/H

The pseudotyped retrovirus-like particle or retroviral vector according to the invention comprises at least one cell targeting fusion protein and at least one modulating fusion protein. The cell targeting fusion protein and/or the modulating fusion protein comprise a first protein derived from an envelope glycoprotein G or H of a virus of the Paramyxoviridae family.

The envelope glycoprotein G or H is as defined above in the section "Envelope glycoproteins of the Paramyxoviridae family".

The virus of the Paramyxoviridae family is as defined above in the section "Pseudotyped retrovirus-like particle or retroviral vector".

By the expression "protein derived from an envelope glycoprotein G or H", it is herein meant that the protein comprises at least one modification by comparison to the sequence of the envelope glycoprotein G or H.

A preferred envelope glycoprotein G is a Nipah virus envelope glycoprotein G, also referred to as NiV envelope glycoprotein G, NiV G glycoprotein, or NiV-G.

A preferred envelope glycoprotein H is a measles virus envelope glycoprotein H, also referred to as MeV glycoprotein H, MeV hemagglutinin, or MV-H.

The envelope glycoprotein G or H is a wild-type or vaccine strain virus envelope glycoprotein or a variant thereof, provided that said variant retains the capacity of said wild-type or vaccine strain glycoprotein of recognizing the receptor on the target membrane and to support the F protein in its membrane fusion function.

A reference sequence for a NiV envelope glycoprotein G is sequence SEQ ID NO: 9.

The NiV envelope glycoprotein G may be of a sequence at least at least 80%, 85%, 90%, 95%, 96%, 97%, 98% or 99% identical to SEQ ID NO: 9. For example, the NiV envelope glycoprotein may be of sequence SEQ ID NO: 9.

A reference sequence for MeV hemagglutinin is sequence SEQ ID NO: 10.

The MeV hemagglutinin may be of a sequence at least at least 80%, 85%, 90%, 95%, 96%, 97%, 98% or 99% identical to SEQ ID NO: 10. For example, the MeV hemagglutinin may be of sequence SEQ ID NO: 10.

In a preferred embodiment, the protein derived from the envelope glycoprotein G lacks at least one part of the cytoplasmic region of said envelope glycoprotein G.

The protein lacking at least one part of the cytoplasmic region of said envelope glycoprotein G is also referred to as a protein truncated in its cytoplasmic region.

The expressions "protein lacking x amino acids of the cytoplasmic region", "protein truncated by x amino acids in its cytoplasmic region" and "protein Δax" are herein synonymous and may be used interchangeably.

Using an envelope glycoprotein G truncated in its cytoplasmic region greatly improves its incorporation into retrovirus-like particles and retroviral vectors, thereby allowing generating pseudotyped retrovirus-like particles or retroviral vectors with higher titers and production yield.

The cytoplasmic region of the envelope glycoprotein G is located at the N-terminus.

Thus, when ascertaining the location of the truncated part of a glycoprotein Δax by reference to the non-truncated glycoprotein G, one begins counting at the second amino acid residue of the N-terminal end of the envelope glycoprotein G, i.e. omitting the first methinonine residue.

As an example, a protein that lacks X amino acids in the cytoplasmic region of the glycoprotein G of sequence SEQ ID NO: Z differs from said glycoprotein G in that it lacks amino acids 2 to 1+X of sequence SEQ ID NO: Z.

The localisation of the cytoplasmic region in the envelope glycoprotein G sequence can be easily determined by the skilled person.

The cytoplasmic region of the MeV H glycoprotein for example consists of the amino acids 1 to 34 of sequence SEQ ID NO: 10.

The cytoplasmic region of the NiV G glycoprotein for example consists of the amino acids 1 to 45 of sequence SEQ ID NO: 9.

For example, the protein derived from the envelope glycoprotein G or H may lack at least 10 amino acids, at least 15 amino acids, at least 18 amino acids, at least 20 amino acids in the cytoplasmic region.

For example, the protein derived from the measles virus envelope glycoprotein H may lack at least 10 amino acids, at least 15 amino acids, at least 18 amino acids, at least 20 amino acids, at least 24 amino acids in the cytoplasmic region. In a preferred embodiment, the protein derived from the measles virus envelope glycoprotein H lacks 15, 18, 20 or 24 amino acids.

For example, the protein derived from the Nipah virus envelope glycoprotein G may lack at least 10 amino acids, at least 15 amino acids, at least 18 amino acids, at least 20 amino acids, at least 25 amino acids or at least 30 amino acids in the cytoplasmic region.

In a preferred embodiment, the protein derived from the Nipah virus envelope glycoprotein G lacks 34 amino acids.

In a preferred embodiment, the protein derived from the envelope glycoprotein G or H is at least partially unable to bind at least one natural receptor of said envelope glycoprotein G or H.

The at least partially inability to bind at least one natural receptor of said envelope glycoprotein G or H may be obtained by at least one mutation introduced in the sequence of said envelope glycoprotein G or H.

For example, the protein derived from the envelope glycoprotein G or H may comprise at least one point mutation, preferably at least two point mutations, by comparison to the sequence of said envelope glycoprotein.

The point mutation may be an amino acid deletion, addition or substitution.

In a preferred embodiment, the point mutation is a substitution.

In a preferred embodiment, the protein derived from the envelope glycoprotein G or H is unable to bind, ie completely unable to bind, at least one natural receptor of said envelope glycoprotein G or H.

The inability of the protein derived from the envelope glycoprotein G or H to bind to its natural receptor greatly increases cell targeting efficiency.

Assessing the ability to bind to at least one natural receptor of an envelope glycoprotein G may be assessed by any method well known by the skilled person.

The natural NiV receptors are Ephrin-B2 and -B3 NiV receptors.

The protein derived from the NiV envelope glycoprotein G is thus preferably at least partially unable to bind Ephrin-B2 receptor and/or Ephrin-B3 NiV receptor, preferably both Ephrin-B2 receptor and Ephrin-B3 NiV receptor.

For example, the envelope glycoprotein NiV-G may comprise at least two or at least three point mutations by comparison to sequence SEQ ID NO: 9, wherein said point mutations are selected in the group consisting of E501A, W504A, Q530A and E533A.

In a preferred embodiment, the glycoprotein NiV-G comprises or consists of the point mutations E501A, W504A, Q530A and E533A, thus leading to the inability to bind Ephrin-B2 receptor and Ephrin-B3 NiV receptor.

The natural MeV receptors are SLAM, nectin-4 and CD46.

The protein derived from the MeV envelope glycoprotein H is thus preferably at least partially unable to bind SLAM, nectin-4 and/or CD46, preferably at least both SLAM and CD46.

For example, the envelope glycoprotein MV-H may comprise at least two or at least three point mutations by comparison to sequence SEQ ID NO: 10, wherein said point mutations are selected in the group consisting of Y481A, R533A, S548L and F549S.

In one preferred embodiment, the envelope glycoprotein MV-H comprises or consists of the point mutations Y481A, R533A, S548L and F549S, thus leading to the inability to bind SLAM and CD46.

Thus, the protein derived from the envelope glycoprotein G or H preferably lacks at least one part of the cytoplasmic region of said envelope glycoprotein G or H and/or is at least partially unable to bind at least one natural receptor of said envelope glycoprotein G or H.

In a more preferred embodiment, the protein derived from the envelope glycoprotein G or H both lacks at least one part of the cytoplasmic region of said envelope glycoprotein G or H and is at least partially unable to bind at least one natural receptor of said envelope glycoprotein G or H.

By "a sequence at least x % identical to a reference sequence", it is herein intended that the sequence is identical to the reference sequence or differ from the reference sequence by up to 100-x amino acid alterations per each 100 amino acids of the reference sequence.

The alignment and the determination of the percentage of identity may be carried out manually or automatically using for instance the Needle program which is based on the Needleman and Wunsch algorithm, described in Needleman and Wunsch (1970) J. Mol Biol. 48:443-453, with for example the following parameters for polypeptide sequence comparison: comparison matrix: BLOSUM62, gap open penalty: 10 and gap extend penalty: 0.5, end gap penalty: false, end gap open penalty=10, end gap extend penalty=0.5; and the following parameters for polynucleotide sequence comparison: comparison matrix: DNAFULL; gap open penalty=10, gap extend penalty=0.5, end gap penalty: false, end gap open penalty=10, end gap extend penalty=0.5.

As defined herein, an amino acid sequence "at least 80%, 85%, 90%, 95%, 96%, 97%, 98% or 99% identical" to a reference sequence may comprise mutations, such as deletions, insertions and/or substitutions compared to the reference sequence.

In case of substitutions, the substitution preferably corresponds to a conservative substitution as indicated in the Table 1 below. In a preferred embodiment, the sequence at least 80%, 85%, 90%, 95%, 96%, 97%, 98% or 99% identical to a reference sequence only differs from the reference sequence by conservative substitutions.

TABLE 1

| Conservative substitutions | Type of Amino Acid |
| --- | --- |
| Ala, Val, Leu, Ile, Met, | Amino acids with aliphatic hydrophobic |

TABLE 1-continued

| Conservative substitutions | Type of Amino Acid |
| --- | --- |
| Pro, Phe, Trp | side chains |
| Ser, Tyr, Asn, Gln, Cys | Amino acids with uncharged but polar side chains |
| Asp, Glu | Amino acids with acidic side chains |
| Lys, Arg, His | Amino acids with basic side chains |
| Gly | Neutral side chain |

In another preferred embodiment, the amino acid sequence at least 80%, 85%, 90%, 95%, 96%, 97%, 98% or 99% identical to a reference sequence corresponds to a naturally-occurring allelic variant of the reference sequence.

Glycoprotein Derived from an Envelope Glycoprotein F

The pseudotyped retrovirus-like particle or retroviral vector according to the invention also comprises at least one glycoprotein derived from an envelope glycoprotein F of a virus of the Paramyxoviridae family, wherein said glycoprotein preferably lacks at least one part of the cytoplasmic region of said envelope glycoprotein F.

The envelope glycoprotein F is as defined above in the section "Envelope glycoproteins of the Paramyxoviridae family".

The virus of the Paramyxoviridae family is as defined above in the section "Pseudotyped retrovirus-like particle or retroviral vector".

By the expression "protein derived from an envelope glycoprotein F", it is herein meant that the protein comprises at least one modification by comparison to the sequence of the envelope glycoprotein F.

A preferred envelope glycoprotein F is a Nipah virus envelope glycoprotein F, also referred to as NiV envelope glycoprotein F, NiV F glycoprotein, or NiV-F.

Another preferred envelope glycoprotein F is a measles virus envelope glycoprotein F, also referred to as MeV glycoprotein F or MeV-F.

The envelope glycoprotein F is a wild-type virus or vaccine strain envelope glycoprotein or a variant thereof, provided that said variant retains the capacity of the wild-type or vaccine strain glycoprotein F to mediate the fusion of viral membranes with the cellular membrane of the targeted or host cell.

A reference sequence for a NiV envelope glycoprotein F is sequence SEQ ID NO: 11. The NiV envelope glycoprotein F may be of a sequence at least at least 80%, 85%, 90%, 95%, 96%, 97%, 98% or 99% identical to SEQ ID NO: 11. For example, the NiV envelope glycoprotein F may be of sequence SEQ ID NO: 11.

A reference sequence for MeV envelope glycoprotein F is sequence SEQ ID NO: 12.

The MeV envelope glycoprotein F may be of a sequence at least at least 80%, 85%, 90%, 95%, 96%, 97%, 98% or 99% identical to SEQ ID NO: 12. For example, the MeV envelope glycoprotein F may be of sequence SEQ ID NO: 12.

In a preferred embodiment, the protein derived from the envelope glycoprotein F lacks at least one part of the cytoplasmic region of said envelope glycoprotein F.

The protein lacking at least one part of the cytoplasmic region of said envelope glycoprotein F is also referred to as a protein truncated in its cytoplasmic region.

The expressions "protein lacking x amino acids of the cytoplasmic region", "protein truncated by x amino acids in its cytoplasmic region" and "protein Δax" are herein synonymous and may be used interchangeably.

Using an envelope glycoprotein F truncated in its cytoplasmic region greatly improves its incorporation into retrovirus-like particles and retroviral vectors, thereby allowing generating pseudotyped retrovirus-like particles or retroviral vectors with higher titers and production yield.

The cytoplasmic region of the envelope glycoprotein F is located at the C-terminus.

Thus, when ascertaining the location of the truncated part of a glycoprotein Δax by reference to the non-truncated glycoprotein G, one begins counting from the C-terminal end of the glycoprotein F.

As an example, a glycoprotein that lacks X amino acids in its cytoplasmic region by comparison to the glycoprotein F of sequence SEQ ID NO: Z consisting of n amino acids differs from said glycoprotein F in that it lacks amino acids n-x+1 to n of sequence SEQ ID NO: Z.

The localisation of the cytoplasmic region in the envelope glycoprotein F sequence can be easily determined by the skilled person.

The cytoplasmic region of the MeV glycoprotein F for example consists of the amino acids 518 to 550 of sequence SEQ ID NO: 12 (33 amino acids).

The cytoplasmic region of the NiV glycoprotein F for example consists of the amino acids 519 to 546 of sequence SEQ ID NO: 11 (28 amino acids).

For example, the protein derived from the envelope glycoprotein F may lack at least 10 amino acids, at least 15 amino acids, at least 20 amino acids, at least 25 or at least 30 amino acids in the cytoplasmic region.

For example, the protein derived from the measles virus envelope glycoprotein F may lack 30 amino acids in the cytoplasmic region by comparison to said measles virus envelope glycoprotein F. For example, said protein derived from the measles virus envelope glycoprotein F and lacking 30 amino acids in the cytoplasmic region comprises or consists of sequence SEQ ID NO: 15.

For example, the protein derived from the Nipah virus envelope glycoprotein F may lack 22 amino acids in the cytoplasmic region by comparison to said Nipah virus envelope glycoprotein F. For example, said protein derived from the Nipah virus envelope glycoprotein F and lacking 22 amino acids in the cytoplasmic region comprises or consists of sequence SEQ ID NO: 16.

Target Cells

The target cells are cells of interest, whose activity is to be modulated and/or that are to be transduced with at least one gene of interest.

The target cells express at their surface a specific cell surface receptor, thereby allowing to specifically target these cells and not the cells that do not express said cell surface receptor.

The expressions "target cells" and "target subset of cells" are herein synonymous and may be used interchangeably.

Target cells may be selected in the group consisting of hematopoietic cells, stroma cells, endothelial cells, liver cells, muscle cells (e.g. heart cells), cells of the nervous system and/or diseased cells.

Cells of the nervous system are for example neurons and/or glial cells.

By "hematopoietic cells", it is herein meant cells of the hematopoietic system.

Preferred target cells are hematopoietic cells.

Hematopoietic cells may be selected in the group consisting of T cells, B cells, monocytes, Th1 cells, Th2 cells, Treg cells, mast cells, dendritic cells (DCs), natural killer (NK) cells, natural killer T (NKT) cells, macrophages, hematopoietic stem cells, progenitor T and/or B cells, erythroblasts, platelets, neutrophils and their combinations.

More preferred target hematopoietic cells are T cells, more preferably CD8+ T cells or CD4+ T cells.

Diseased cells may be tumor cells, tumor stem cells, cells lacking a specific functional gene, overexpressing a specific gene and/or expressing a truncated or mutated form of a specific gene, infected cells and/or functionally impaired cells.

Cell-Specific Targeting Domain

The cell-specific targeting domain (also called "cell targeting domain") allows the specific binding of the pseudotyped retrovirus-like particle or retroviral vector according to the invention to a surface receptor selectively expressed by target cells.

Target cells may be as defined above in the section of the same name.

The cell targeting domain of the targeting fusion protein is preferably selected in the group consisting of a DARPin, a scFv, targeting peptide and their combinations.

The term "DARPin" refers to designed ankytin repeat proteins.

The term scFv refers to single-chain variable fragment of an antibody.

For example, the cell targeting domain is specific for CD3, CD8, CD4, a cancer cell marker, CD11b, CD19, CD62L, CD56, Glut-1(glucose transporter), CD19, CD22, CD20, CCR5 or CXCR4.

A preferred cell targeting domain is a DARPin specific for CD4 or a scFv specific for CD8.

Functional Domain

The functional domain allows modulating the activity of the target cells.

By "modulating the activity of a target cell", it is herein meant to activate or inhibit, induce a phenotype change (for example maturation and/or differentiation), induce proliferation, and/or induce apoptosis of said target cell. Modulating the activity of a target cell for example comprises enhancing or suppressing immunity, promoting cell type-specific immune response(s).

The functional domain of the modulating fusion protein is preferably a receptor ligand.

By "receptor ligand", it is herein meant a molecule, preferably a protein, preferably normally released by cells, and that alters the physiological state of cells expressing a cognate receptor at their cell surface. The receptor ligand is for example selected in the group consisting of a cytokine, growth factor, hormone, neuromediator, apoptosis ligand, a chemokine, glucose transporter and their combinations.

For example, the cytokine may be selected in the group consisting of interleukin (IL) TNF (Tumor Necrosis Factor) or interferon.

The interleukin may for example be IL-2, IL-3, IL-6, IL-7, ID 5, IL21, IL-17 or IL-12.

For example, the apoptosis ligand may be FAS Ligand, CD40 Ligand or TNFalpha.

For example, the chemokine may be CXCL4, CCL5 or CXCL10.

For example, the growth factor may be GM-SCF (Granulocyte-Macrophage Colony-Stimulating Factor), Stem cells factor (SCF), thrombopoietin (TPO) or Flt-3 Ligand.

For example, the hormone may be insulin, growth hormone or a hormone peptide, for example vasopressin. For example, the neuromediator may be a neuropeptide, for example selected among insulin, glucagon, calcitonin, neurotensin or bradykinin.

A preferred functional domain is a cytokine, preferably an interleukin, more preferably IL-7.

Cell Targeting and Modulating Fusion Proteins

The retrovirus-like particle and retroviral vector according to the invention comprises two types of fusion proteins: one cell targeting fusion protein and one modulating fusion protein.

The cell targeting fusion protein comprises (i) a protein derived from an envelope glycoprotein G of H of a virus of the Paramyxoviridae family or a transmembrane domain and (ii) at least one cell targeting domain.

The modulating fusion protein comprises (i) a protein derived from an envelope glycoprotein G or H of a virus of the Paramyxoviridae family or a transmembrane domain and (ii) at least one functional domain.

It will be clearly understood by the skilled person that, since the cell targeting fusion protein and the modulating fusion protein are two different types of fusion proteins, the cell targeting domain and the functional domain are different.

The transmembrane domain may be any naturally-occurring or non-naturally occurring transmembrane domain.

The transmembrane domain may be a transmembrane domain of a receptor, a transmembrane protein, preferably a viral transmembrane protein, a fragment of a transmembrane protein, a transmembrane peptide or a variant thereof, such as a genetically modified transmembrane domain of a receptor, a genetically modified transmembrane protein, a genetically modified fragment of a transmembrane protein or a genetically modified transmembrane peptide.

Examples of transmembrane domain are the transmembrane domain (TMD) of the platelet-derived growth factor receptor (PDGFR), the transmembrane domain of CD34 or the VSVG glycoprotein transmembrane domain.

The C-terminus of the protein derived from an envelope glycoprotein G or H of a virus of the Paramyxoviridae family is preferably fused, directly or indirectly (for example via a linker), to the N-terminus of the cell targeting or functional domain.

The C-terminus of the transmembrane domain is preferably fused, directly or indirectly (for example via a linker), to the N-terminus of the cell targeting or functional domain.

The protein derived from an envelope glycoprotein G or H of a virus of the Paramyxoviridae family, the glycoprotein derived from an envelope glycoprotein F, the cell targeting domain and the functional domain are as defined above.

When both present in the pseudotyped retrovirus-like particle or retroviral vector, the protein derived from an envelope glycoprotein G or H of a virus of the Paramyxoviridae family in the cell targeting fusion protein and those in the modulating fusion protein may be derived from the same virus of the Paramyxoviridae family or from different viruses of the Paramyxoviridae family.

When the protein derived from an envelope glycoprotein G or H of a virus of the Paramyxoviridae family in the cell targeting fusion protein and those in the modulating fusion protein are derived from different viruses of the Paramyxoviridae family, they preferably derive from a virus of the same genus, more preferably from a virus of the same species.

The protein derived from an envelope glycoprotein G or H of a virus of the Paramyxoviridae family in the cell targeting fusion protein and those in the modulating fusion protein are preferably identical. In a preferred embodiment, the cell targeting fusion protein thus differs from the modulating fusion protein by its targeting domain instead of a functional domain and, possibly, when present, of at least one linker and/or at least one tag.

The two proteins of the fusion protein may be linked together with a linker. Any suitable linker well-known by the skilled person may be used.

For example, the linker may be $(G_4S)_3$, $G_4S$, Factor Xa cutting site or helical linker (for example HL3, HL7, . . . ).

The fusion proteins may be tagged, for example to facilitate their purification and/or detection.

When present, the tag is preferably located at the C-terminus of the fusion protein, i.e. fused to the N-terminus of the cell targeting domain and/or of the functional domain. Any suitable tag well-known by the skilled person may be used.

For example, the tag may be a His-Tag, RGS-His tag, such as $RGSH_6$, HA tag or c-myc tag.

Specific Pseudotyped Retrovirus-Like Particle or Retroviral Vector

The present invention particularly relates to a pseudotyped retrovirus-like particle or retroviral vector comprising:
a) at least one cell targeting fusion protein comprising (i) a protein derived from an envelope glycoprotein G or H of a virus of the Paramyxoviridae family or a transmembrane domain and (ii) at least one cell targeting domain,
b) at least one modulating fusion protein comprising (i) a protein derived from an envelope glycoprotein G or H of a virus of the Paramyxoviridae family or a transmembrane domain and (ii) at least one functional domain, and
c) at least one glycoprotein derived from an envelope glycoprotein F of a virus of the Paramyxoviridae family,
wherein said cell targeting fusion protein and/or said modulating fusion protein comprises a protein derived from an envelope glycoprotein G or H of a virus of the Paramyxoviridae family.

The pseudotyped retrovirus-like particle or retroviral vector thus comprises at least one fusion protein comprising a protein derived from an envelope glycoprotein G or H of a virus of the Paramyxoviridae family, said fusion protein being a cell targeting fusion protein or a modulating fusion protein. In one embodiment, the pseudotyped retrovirus-like particle or retroviral vector comprises two fusion proteins comprising each a protein derived from an envelope glycoprotein G or H of a virus of the Paramyxoviridae family, wherein one fusion protein is a cell targeting fusion protein and the second fusion protein is a modulating fusion protein.

In one embodiment, the pseudotyped retrovirus-like particle or retroviral vector comprises:
a) at least one cell targeting fusion protein comprising (i) a protein derived from an envelope glycoprotein G or H of a virus of the Paramyxoviridae family and (ii) at least one cell targeting domain,
b) at least one modulating fusion protein comprising (i) a transmembrane domain and (ii) at least one functional domain, and
c) at least one glycoprotein derived from an envelope glycoprotein F of a virus of the Paramyxoviridae family.

In one embodiment, the pseudotyped retrovirus-like particle or retroviral vector comprises:
a) at least one cell targeting fusion protein comprising (i) a transmembrane domain and (ii) at least one cell targeting domain,
b) at least one modulating fusion protein comprising (i) a protein derived from an envelope glycoprotein G or H of a virus of the Paramyxoviridae family and (ii) at least one functional domain, and
c) at least one glycoprotein derived from an envelope glycoprotein F of a virus of the Paramyxoviridae family.

In one embodiment, the pseudotyped retrovirus-like particle or retroviral vector comprises:
a) at least one cell targeting fusion protein comprising (i) a protein derived from an envelope glycoprotein G or H of a virus of the Paramyxoviridae family and (ii) at least one cell targeting domain,
b) at least one modulating fusion protein comprising (i) a protein derived from an envelope glycoprotein G or H of a virus of the Paramyxoviridae family and (ii) at least one functional domain, and
c) at least one glycoprotein derived from an envelope glycoprotein F of a virus of the Paramyxoviridae family.

The protein derived from an envelope glycoprotein G of a virus of the Paramyxoviridae family in the cell targeting fusion protein, those in the modulating fusion protein and the glycoprotein derived from an envelope glycoprotein F may derived from the same virus of the Paramyxoviridae family or from different viruses of the Paramyxoviridae family.

When the protein derived from an envelope glycoprotein G of a virus of the Paramyxoviridae family in the cell targeting fusion protein, those in the modulating fusion protein and/or the glycoprotein derived from an envelope glycoprotein F are derived from different viruses of the Paramyxoviridae family, they preferably derive from a virus of the same genus, more preferably from a virus of the same species.

In one embodiment, the protein derived from an envelope glycoprotein G of a virus of the Paramyxoviridae family in the cell targeting fusion protein, those in the modulating fusion protein and the glycoprotein derived from an envelope glycoprotein F are derived from the same virus of the Paramyxoviridae family.

In another embodiment, the protein derived from an envelope glycoprotein G of a virus of the Paramyxoviridae family in the cell targeting fusion protein and the glycoprotein derived from an envelope glycoprotein F of a virus of the Paramyxoviridae family are derived from the same virus of the Paramyxoviridae family, whereas the modulating fusion protein comprises (i) a transmembrane domain, for example the transmembrane domain (TMD) of the platelet-derived growth factor receptor (PDGFR), and (ii) at least one functional domain.

In another embodiment, the protein derived from an envelope glycoprotein G of a virus of the Paramyxoviridae family in the modulating fusion protein and the glycoprotein derived from an envelope glycoprotein F of a virus of the Paramyxoviridae family are derived from the same virus of the Paramyxoviridae family, whereas the cell targeting fusion protein comprises (i) a transmembrane domain, for example the transmembrane domain (TMD) of the platelet-derived growth factor receptor (PDGFR), and (ii) at least one cell targeting domain.

The different components of the pseudotyped retrovirus-like particle or retroviral vector, in particular the cell targeting fusion protein, the modulating fusion protein, the glycoprotein derived from an envelope glycoprotein F of a virus of the Paramyxoviridae family and the transmembrane domain are as defined above.

A preferred pseudotyped retrovirus-like particle or retroviral vector comprises:
a) at least one cell targeting fusion protein comprising (i) a protein derived from an envelope glycoprotein G of a virus of the Paramyxoviridae family, said protein lacking at least one part of the cytoplasmic region of said envelope glycoprotein G and being at least partially unable to bind at least one natural receptor of said envelope glycoprotein G or a transmembrane domain and (ii) at least one cell targeting domain,
b) at least one modulating fusion protein comprising (i) a protein derived from an envelope glycoprotein G of a virus of the Paramyxoviridae family, said protein lacking at least one part of the cytoplasmic region of said envelope glycoprotein G and being at least partially unable to bind at least one natural receptor of said envelope glycoprotein G or a transmembrane domain and (ii) at least one functional domain, and
c) at least one glycoprotein derived from an envelope glycoprotein F of a virus of the Paramyxoviridae family and lacking at least one part of the cytoplasmic region of said envelope glycoprotein F,
wherein said cell targeting fusion protein and/or said modulating fusion protein comprises a protein derived from an envelope glycoprotein G or H of a virus of the Paramyxoviridae family.

Examples of pseudotyped retrovirus-like particle or retroviral vector are given below in Table 2.

TABLE 2

| | Cell targeting fusion protein | | Modulating fusion protein | | |
|---|---|---|---|---|---|
| Name | protein derived from envelope glycoprotein G or H | cell targeting domain | protein derived from envelope glycoprotein G or H | functional domain | Glycoprotein derived from an envelope glycoprotein F |
| MeV 4$^H$/IL7$^H$ | HcΔ15, HcΔ18 or HcΔ20 4 mutations Y481A, R533A, S548L, F549S | DARpin specific of human CD4 | HΔ15, HΔ18 or HΔ20 4 mutations Y481A, R533A, S548L, F549S | IL-7 | FΔ30 |
| | For example SEQ ID NO: 2 comprising HcΔ15 and a His Tag | | For example SEQ ID NO: 14 comprising HcΔ15 and a His Tag | | For example SEQ ID NO: 15 |
| NiV | GcΔ34 | scFv | GcΔ34 | IL-7 | FΔ22 |

TABLE 2-continued

| | Cell targeting fusion protein | | Modulating fusion protein | | |
|---|---|---|---|---|---|
| Name | protein derived from envelope glycoprotein G or H | cell targeting domain | protein derived from envelope glycoprotein G or H | functional domain | Glycoprotein derived from an envelope glycoprotein F |
| $8^G$/IL7$^G$ | 4 mutations: E501A, W504A, Q530A, E533A For example SEQ ID NO: 4 comprising a His Tag and a linker (G$_4$S)$_3$ | specific of human CD8 | 4 mutations: E501A, W504A, Q530A, E533A For example SEQ ID NO: 6 comprising a His Tag | | For example SEQ ID NO: 16 |

In a preferred embodiment, the pseudotyped retrovirus-like particle or retroviral vector is obtainable or obtained by the method of production described below in the section "Method for producing a pseudotyped retrovirus-like particle or retroviral vector " herein below.

Nucleic Acid and Vector

The present invention also relates to a nucleic acid encoding the cell targeting fusion protein and/or the modulating fusion protein used for pseudotyping the retrovirus-like particle or retroviral vector according to the invention.

The present invention thus particularly relates to a nucleic acid comprising a sequence encoding a cell targeting fusion protein and/or a sequence encoding a modulating fusion protein, wherein:

- said cell targeting fusion protein comprises (i) a protein derived from an envelope glycoprotein G of a virus of the Paramyxoviridae family, said protein preferably lacking at least one part of the cytoplasmic region of said envelope glycoprotein G and being preferably at least partially unable to bind at least one natural receptor of said envelope glycoprotein G or a transmembrane domain and (ii) at least one cell targeting domain,
- said modulating fusion protein comprises (i) a protein derived from an envelope glycoprotein G of a virus of the Paramyxoviridae family, said protein preferably lacking at least one part of the cytoplasmic region of said envelope glycoprotein G and being preferably at least partially unable to bind at least one natural receptor of said envelope glycoprotein G or a transmembrane domain and (ii) at least one functional domain.

When the nucleic acid comprises a sequence encoding a cell targeting fusion protein and a sequence encoding a modulating fusion protein, said cell targeting fusion protein and/or said modulating fusion protein comprise(s) a protein derived from an envelope glycoprotein G or H of a virus of the Paramyxoviridae family.

The nucleic acid preferably comprises or consists of:

(i) a sequence encoding a protein derived from an envelope glycoprotein of a virus of the Paramyxoviridae family, said protein preferably lacking at least one part of the cytoplasmic region of said envelope glycoprotein G and being preferably at least partially unable to bind at least one natural receptor of said envelope glycoprotein G, (ii) a sequence encoding one cell targeting domain or one functional domain, and (iii) optionally, a linker sequence between sequences (i) and (ii), (iv) optionally, a sequence encoding a tag, preferably at the 3' end of sequence (ii), wherein sequences (i) and (ii) are fused in frame.

The linker sequence encodes a linker as defined above, for example encodes $(G_4S)_3$.

The sequence (i) is located in 5' of the nucleic acid by comparison to the sequence (ii) located in 3' of the nucleic acid.

In one embodiment, the nucleic acid comprises or consists of a sequence at least 80%, 85%, 90%, 95%, 96%, 97%, 98% or 99% identical to a sequence selected in the group consisting of SEQ ID NO: 1, SEQ ID NO: 3, SEQ ID NO: 5, SEQ ID NO: 7 and SEQ ID NO: 13 and/or comprises or consists of a sequence encoding a sequence at least 80%, 85%, 90%, 95%, 96%, 97%, 98% or 99% identical to a sequence selected in the group consisting of sequences SEQ ID NO: 2, SEQ ID NO: 4, SEQ ID NO: 6, SEQ ID NO: 8 and SEQ ID NO: 14.

In a preferred embodiment, the nucleic acid comprises or consists of a sequence selected in the group consisting of SEQ ID NO: 1, SEQ ID NO: 3, SEQ ID NO: 5, SEQ ID NO: 7 and SEQ ID NO: 13 and/or comprises or consists of a sequence encoding a sequence selected in the group consisting of sequences SEQ ID NO: 2, SEQ ID NO: 4, SEQ ID NO: 6, SEQ ID NO: 8 and SEQ ID NO: 14.

A definition of the percentage of sequence identity is provided above.

A nucleic sequence "at least 80%, 85%, 90%, 95%, 96%, 97%, 98% or 99% identical" to a reference sequence may comprise mutations, such as deletions, insertions and/or substitutions compared to the reference sequence.

In case of substitutions, the substitution preferably corresponds to a silent substitution or a substitution leading to a conservative substitution in the translated amino acid sequence, by comparison to the reference sequence, for example as indicated in the Table 1 above.

In a preferred embodiment, the nucleic sequence at least 80%, 85%, 90%, 95%, 96%, 97%, 98% or 99% identical to a reference sequence only differs from the reference sequence by silent substitution(s) and/or substitution(s) leading to a conservative amino-acid substitution.

The present invention also relates to a nucleic acid encoding a glycoprotein derived from an envelope glycoprotein F of a virus of the Paramyxoviridae family and preferably lacking at least one part of the cytoplasmic region of said envelope glycoprotein F.

The glycoprotein derived from an envelope glycoprotein F of a virus of the Paramyxoviridae family is as defined above.

The nucleic acid is preferably an isolated nucleic acid.

By the expression "nucleic acid", it is herein meant the phosphate ester polymeric form of ribonucleosides (also called "RNA molecule"), deoxyribonucleosides (also called "DNA molecule") or any phosphoester analogs thereof, such as phosphorothioates and thioesters, in either single stranded form or a double-stranded form.

The term "isolated" in reference to a biological component (such as a nucleic acid, a vector or a protein) refers to a biological component that has been substantially separated or purified away from other biological components in the cell of the organism, or the organism itself, in which the component naturally occurs, such as other chromosomal and extra-chromosomal DNA and RNA, proteins, cells, and organelles. "Isolated nucleic acids" or "isolated vectors" include nucleic acid molecules purified by standard purification methods. These terms also encompass nucleic acids and vectors prepared by amplification and/or cloning, as well as chemically synthesized nucleic acids and vectors.

The nucleic acid according to the invention is preferably cloned into a vector.

The term "vector" has therefore a meaning different from a "retroviral vector".

By the term "vector", it is herein meant a nucleic acid vector.

A vector generally comprises an origin of replication, a multicloning site and a selectable marker.

A vector preferably comprises an expression cassette, i.e. a nucleic acid according to the invention placed under the control of at least one expression signal allowing its expression.

The expression signal is particularly selected among a promoter, a terminator, an enhancer and their combinations.

Suitable promoters, terminators and enhancers are well-known by the skilled person.

An example of vector is for example a plasmid.

By "plasmid", it is herein meant a double-stranded circular DNA. The plasmid may include a marker gene enabling to select the cells comprising said plasmid, an origin of replication to allow the cell to replicate the plasmid and/or a multiple cloning site allowing the insertion of a nucleic acid according to the invention.

The present invention thus also relates to a vector comprising a nucleic acid as defined above.

The vector is preferably an isolated vector.

The vector may comprise or consist of:
a first nucleic acid comprising or consisting of:
(i) a sequence encoding a) a protein derived from an envelope glycoprotein G or H of a virus of the Paramyxoviridae family, said protein preferably lacking at least one part of the cytoplasmic region of said envelope glycoprotein G or H and being preferably at least partially unable to bind at least one natural receptor of said envelope glycoprotein G or H or b) a transmembrane domain,
(ii) a sequence encoding one cell targeting domain,
(iii) optionally, a linker sequence between sequences (i) and (ii),
(iv) optionally a sequence encoding a tag, preferably at the 3' end of sequence (ii),
wherein sequences (i) and (ii) are fused in frame,
a second nucleic acid comprising or consisting of:
(i) a sequence encoding a) a protein derived from an envelope glycoprotein G or H of a virus of the Paramyxoviridae family, said protein preferably lacking at least one part of the cytoplasmic region of said envelope glycoprotein G or H and being preferably at least partially unable to bind at least one natural receptor of said envelope glycoprotein G or H or b) a transmembrane domain,
(ii) a sequence encoding one functional domain,
(iii) optionally, a linker sequence between sequences (i) and (ii),
(iv) optionally a sequence encoding a tag, preferably at the 3' end of sequence (ii),
wherein sequences (i) and (ii) are fused in frame,
wherein the first nucleic acid and/or the second nucleic acid comprises a sequence encoding a protein derived from an envelope glycoprotein G or H of a virus of the Paramyxoviridae family.

Said first nucleic acid thus encodes the cell targeting fusion protein and said second nucleic acid encodes the modulating fusion protein.

Gene of Interest

When a pseudotyped retroviral vector is used, at least one gene of interest may be present in the retrovirus-derived genome of said retroviral vector.

The gene of interest may encode a therapeutic protein, apoptotic protein, chimeric antigen receptor, cell surface receptor, antibody, antibody fragment, shRNA, antigen, cytokine, microRNA, CRISPR ((clustered, regularly interspaced, short palindromic repeat))/CAS element(s) (for example CAS9 and/or guide RNAs, in particular for specific gene disruption or correction), other nuclease system, such as Zink Finger Nucleases, S/MAR (Scaffold/Matrix Attachment Region)—episomes, ligand and/or receptor.

A S/MAR-episome is inserted in the cell nucleus by retroviral vectors that then replicate with the host cell DNA.

Examples of gene of interest include globin gene, hematopoietic growth factor gene (for example erythropoietin (EPO) gene), interleukin gene (especially Interleukin-1, Interleukin-2, Interleukin-3, Interleukin-6 or Interleukin-12 gene), colony-stimulating factor gene (such as granulocyte colony-stimulating factor gene, granulocyte/macrophage colony-stimulating factor gene or stem-cell colony-stimulating factor gene), the platelet-specific integrin allbβ gene, multidrug resistance gene, the gp91 or gp 47 genes, which are defective in patients with chronic granulomatous disease (CGD), antiviral gene rendering cells resistant to infections with pathogens (such as human immunodeficiency virus), gene coding for blood coagulation factors VIII or IX which are mutated in hemophilia's, gene encoding a ligand involved in T cell-mediated immune responses (such as T cell antigen receptors, chimeric antigen receptor (CARs), B cell antigen receptors (immunoglobulins, neutralizing antibodies against HIV, Hepatitis C, Hepatitis B and/or other infectious diseases), the interleukin receptor common y chain gene, TNF gene, gamma interferon gene, CTLA4 gene, genes expressed in tumor cells such as Melana, MAGE genes (such as MAGE-1, MAGE-3), P198 gene, P1A gene, gp100 gene.

Method for Producing a Pseudotyped Retrovirus-Like Particle or Retroviral Vector The present invention also relates to a method for producing a pseudotyped retrovirus-like particle or retroviral vector as defined above, wherein said method comprises co-transfecting a packaging cell line with:
(i) at least one nucleic acid encoding a cell targeting fusion protein,
(ii) at least one nucleic acid encoding a modulating fusion protein,
(iii) at least one nucleic acid encoding a glycoprotein derived from an envelope glycoprotein F of a virus of the Paramyxoviridae family and preferably lacking at least one part of the cytoplasmic region of said envelope glycoprotein F, (iv) at least one vector comprising a nucleic acid encoding core proteins from said retrovirus and (v) optionally, at least one vector comprising a packaging competent retroviral derived genome, thereby obtaining co-transfected cells.

Said cell targeting fusion protein and/or said modulating fusion protein comprises a protein derived from an envelope glycoprotein G or H of a virus of the Paramyxoviridae family.

The at least one vector comprising a packaging competent retroviral derived genome is required only for producing a retroviral vector.

Any suitable packaging cell line well known by the skilled person may be used.

By "packaging cell line", it is herein meant a cell line which is able to express the different components of the pseudotyped retrovirus-like particle or retroviral vector of the invention.

The nucleic acids and vectors encoding the different components of the pseudotyped retroviral-like particle or retroviral vector of the invention may be integrated in the genome of the packaging cell line, for example in the case of murine leukemia based vectors.

The packaging cell line is preferably compatible with the expression of lentiviral Gag and Pol genes.

For example, the packaging cell line may be selected in the group consisting of 293T cells, insect cells, TE 671 cells and HT1080 cells.

The term "transfection" means the introduction of at least one foreign nucleic acid or vector (for example DNA, cDNA or RNA) into a cell, so that the host cell will express the protein(s) encoded by said nucleic acid(s) or vector(s). The foreign nucleic acid(s) or vector(s) may include regulatory or control sequences, such as start, stop, promoter, signal, secretion or other sequences used by a cell's genetic machinery.

A vector comprising the psi sequence necessary for encapsidation is called a psi-positive vector, whereas a vector not comprising said psi sequence is called a psi-negative vector.

Only the vector comprising a packaging competent retroviral derived genome is a psi-positive vector. The other nucleic acids and vectors used for the co-transfection are psi-negative.

The nucleic acid encoding a cell targeting fusion protein, the nucleic acid encoding a modulating fusion protein and the nucleic acid encoding a glycoprotein derived from an envelope glycoprotein F of a virus of the Paramyxoviridae family are as defined above. They may be provided in the form of two or three separate vectors: for example, two separate vectors, such as the first one comprising or consisting of the nucleic acid encoding a cell targeting fusion protein and the nucleic acid encoding a modulating fusion protein and the second one comprising or consisting of nucleic acid encoding a glycoprotein derived from an envelope glycoprotein F of a virus of the Paramyxoviridae family; or three separate vectors, the first one comprising or consisting of the nucleic acid encoding a cell targeting fusion protein, the second one comprising or consisting of the nucleic acid encoding a modulating fusion protein and the third one comprising or consisting of nucleic acid encoding a glycoprotein derived from an envelope glycoprotein F of a virus of the Paramyxoviridae family. Alternatively, the nucleic acid encoding a cell targeting fusion protein, the nucleic acid encoding a modulating fusion protein and the nucleic acid encoding a glycoprotein derived from an envelope glycoprotein F of a virus of the Paramyxoviridae family may be provided in a single vector comprising or consisting of these three nucleic acids.

A vector comprising a nucleic acid encoding core proteins from said retrovirus is also used.

By "core proteins from a retrovirus", it is herein meant the proteins encoded by the gag and pol genes. The gag gene encodes a polyprotein which is further processed by the retroviral protease into structural proteins that comprise the core. The pol gene particularly encodes the retroviral protease, reverse-transcriptase and integrase.

A nucleic acid encoding core proteins from a retrovirus thus comprise the gag gene and the pol gene of said retrovirus.

At least one core protein from the retrovirus may be a modified, for example by comparison to the corresponding core protein from a wild-type retrovirus.

In one embodiment, at least one core protein from the retrovirus is modified by at least one amino acid mutation, such as an amino acid deletion, insertion or substitution.

In a preferred embodiment, said at least one modified core protein is a deficient integrase. An example of deficient integrase bears the D116A mutation.

The nucleic acid encoding core proteins may thus comprise at least one mutation in the pol gene and/or at least one mutation in the gag gene. Said at last one mutation may be a nucleotide deletion, insertion or substitution.

In one preferred embodiment, the nucleic acid encoding core proteins comprises at least one mutation in the pol gene, thereby encoding a deficient integrase.

A retroviral vector comprising a deficient integrase is called an integration-deficient retroviral vector. Such vector allows to transiently transfer an encapsidated RNA molecule encoding for a gene of interest.

A preferred integration-deficient retroviral vector is an IDLV (Integration-deficient lentiviral vector).

The origin of the gag and pol genes gives its name to the retrovirus-like particle or retroviral vector. For instance the expression "HIV-1-derived retrovirus-like particle or retroviral vector" usually indicates that the gag and pol genes are those of HIV-1 or are modified gag and pol genes from HIV-1.

A vector comprising a packaging competent retroviral derived genome may also be used for the co-transfection, in particular for the production of a retroviral vector.

By "vector comprising a packaging competent retrovirus derived genome", it is herein meant a vector that comprises the retroviral nucleic acid sequences known as "cis-acting" sequences. These include the Long Terminal Repeats (LTRs) or modified (LTRs), for example lacking at least one part of the U3 region, for the control of transcription and integration, the psi sequence necessary for encapsidation and the Primer Binding site (PBS) and polypurine track (PPT) sequences necessary for reverse transcription of the retroviral genome.

A retroviral vector produced using a vector comprising LTRs lacking at least one part of the U3 region is for example a Self-inactivating (SIN-LTR) vector.

In one embodiment, said vector comprising a packaging competent retrovirus-derived genome further comprises gene(s) of interest, including CRISPR/CAS element(s) and/or a S/MAR-episome.

When using the CRISPR/CAS system, the vector comprising a packaging competent retrovirus-derived genome typically comprises a gene encoding an endonuclease CAS (for example CAS9), a DNA sequence corresponding to the guide RNA (gRNA) specific to the gene of interest to be targeted and, optionally, a sequence for gene correction.

Said retrovirus-derived genome is preferably replication-defective, in the absence of any trans-complementing function. A replication-competent genome would further comprise the gag, pol, and env retroviral genes. In a replication-defective genome, the viral genes gag, pol and env are deleted. Assembly of the retrovirus-like particles or retroviral vectors of the invention is achieved by providing in trans another vector that encodes gag and pol, but that is defective for the "cis" sequences (such as the vector of (iv)), and at least another vector or nucleic acid that encodes the pseudotyped envelope glycoproteins (such as the nucleic acids of (i), (ii) and (iii) or vector(s) comprising said nucleic acids). Their expression allows the encapsidation of the gene of interest, excluding the genes necessary for the multiplication of the viral genome and for the formation of complete viral particles.

The method for producing a pseudotyped retrovirus-like particle or retroviral vector as defined above may further comprise a step of:

b) culturing the co-transfected cells for a time sufficient to allow expression of the proteins encoded by said nucleic acid(s) and vector(s); and c) allowing the encoded proteins to form retrovirus-like particles or retroviral vectors.

Modulating the Activity of and/or Transducing Specific Cells or Subtype of Cells Another object of the invention is the use, preferably in vitro or ex vivo use, of a pseudotyped retrovirus-like particle or retroviral vector as defined above to selectively modulate the activity of target cells and, optionally, selectively transduce target cells.

Still another object of the invention is a method, preferably in vitro or ex vivo method, for selectively modulating the activity of target cells and, optionally, selectively transducing target cells, wherein said method comprises contacting a pseudotyped retrovirus-like particle or retroviral vector as defined above with cells comprising said target cells.

The term "selectively" in the expression "selectively modulating the activity of target cells" means that essentially only said target cells have their activity modulated by the pseudotyped retrovirus-like particle or retroviral vector. For example, the cells whose activity is modulated comprise less than 10%, for example less than 5% or less than 1% of non-targeted cells.

The term "selectively" in the expression "selectively transducing target cells" herein means that essentially only the target cells are transduced. For example, the transduced cells comprise less than 10%, for example less than 5% or less than 1% of non-targeted cells are transduced.

The expression "modulating the activity of a target cell" is as defined above in the section "Functional domain".

As used herein, the term "transferring" or "transducing" relates to the capacity of the retrovirus-like particle or retroviral vector to deliver a biological material to the membrane or the cytoplasm of target cells, upon being bound to the target cells. After delivery, the biological material can be translocated to other compartment(s) of the cell.

As used herein, the expression "biological material" relates to one or more compounds liable to alter the structure and/or the function of a cell. Within the context of the present invention, it is preferred that the biological material is one or more nucleic acids comprising a gene of interest, which may be comprised within the genome of the retroviral vector, as explained above.

Conditions to perform the transduction of cells are well-known from the skilled person and typically include incubating the cells to be transduced, preferably cultured in flasks, plates or dishes coated for example with retronectin, and optionally pre-stimulated with cytokine cocktails, with the pseudotyped retroviral vector, preferably at an MOI (Multiplicity of Infection) between 0.5 and 100.

The target cells are particularly as defined above in the section of the same name.

The pseudotyped retrovirus-like particle or retroviral vector may be contacted with cells comprising the target cells in a culture medium.

The skilled person knows the medium culture appropriate for given cells.

The pseudotyped retrovirus-like particle or retroviral vector may thus be used in vitro or in vivo for changing a defined cell function, thereby providing new tools for basic research.

Pharmaceutical Composition

The present invention also relates to a pharmaceutical composition comprising at least one pseudotyped retrovirus-like particle or retroviral vector as defined above.

The amount of pseudotyped retrovirus-like particle or retroviral vector to be used in a pharmaceutical composition depends, for example, on the immunogenicity, the condition of the subject intended for administration (e.g. weight, age, sex, health, concurrent treatment, if any, and frequency of treatment), the mode of administration, the type of formulation and/or the number of the target cells.

The pharmaceutical composition preferably comprises at least one pseudotyped retrovirus-like particle or retroviral vector and at least one pharmaceutically acceptable carrier.

As used herein, the term "pharmaceutically acceptable carrier" is meant to encompass any carrier, which does not interfere with the effectiveness of the biological activity of the active ingredient and that is preferably not toxic to the host to which is administered.

Pharmaceutically acceptable carriers that may be used in a pharmaceutical composition of the invention are well-known by the skilled person. For example, they include ion exchangers, alumina, aluminium stearate, lecithin, self-emulsifying drug delivery systems (SEDDS), such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2-and 3-hydroxypropyl-β-cyclodextrins, or other solubilized derivatives may also be advantageously used to enhance delivery of compositions according to the invention.

The pharmaceutical composition may comprise from $10^6$ IU to $10^{12}$ IU of pseudotyped retroviral vector, preferably from $10^7$ IU to $10^9$ IU, more preferably from $10^7$ IU to $10^8$ IU.

The terms "IU" or "infection unit" herein mean the quantity of infectious vector particles determined by titration on a cell line and expressed as IU/ml.

The administration may be achieved in a single dose or several doses of the pharmaceutical composition according to the invention, said several doses being injected at the same time or separately over time.

In one embodiment, the pharmaceutical compositions are presented in unit dosage forms to facilitate accurate dosing. The term "unit dosage forms" refers to physically discrete units suitable as unitary dosages for human subjects and other mammals, each unit containing a pre-determined quantity of active material calculated to produce the desired therapeutic effect, in association with a suitable pharmaceutical excipient. Typical unit dosage forms include pre-filled, pre-measured ampoules or syringes of the liquid compositions. In such compositions, the pseudotyped retrovirus-like particle or retroviral vector is usually a minor component, with the remainder being various vehicles or carriers and processing aids helpful for forming the desired dosing form.

The invention further provides kits comprising a pharmaceutical composition comprising a pseudotyped retrovirus-like particle or retroviral vector as defined above and instructions regarding the mode of administration. These instructions may e.g. indicate the medical indication, the route of administration, the dosage and/or the group of patients to be treated.

Subject to be Treated

The subject to be treated may be a mammal, for example a human being or a non-human mammal.

A human being is also referred to as an "individual" or a "patient".

Said human being may be of any age, for example an infant, child, adolescent, adult, elderly people, and of any sex.

A non-human mammal is preferably a rodent (for example a mouse, rat or rabbit), a feline (for example a cat), a canine (for example a dog) or a primate (for example a chimpanzee).

The subject to be treated is preferably a human being.

Prevention and/or Treatment of a Disease

The present invention is particularly useful for the prevention and/or treatment of a disease that may be prevented and/or cured by selectively modulating the activity of specific cells or subset of cells and, optionally, by selectively transducing said specific cells or subset of cells.

Said disease preferably involves specific cells or subset of cells.

The subject to be treated may thus suffer from or may be likely to be affected by a disease that may be prevented and/or cured by selectively modulating the activity of specific cells or subset of cells and, optionally, by selectively transducing said specific cells or subset of cells.

Said disease may be selected in the group consisting of an immune disease (for example an auto-immune disease), cancer, genetic disease, allergic disease, inflammatory disease, infectious disease (in particular bacteria and/or virus infection), metabolic disease, neurodegenerative disease (for example neural dystrophy, Parkinson disease, Huntington disease, Alzheimer disease), muscular disease and their combinations.

As used herein, the expression "autoimmune disease" refers to a disease due to an overactive immune response of the body against substances and/or tissues normally present in the body. Accordingly, by specifically targeting immune cells involved in this overactive immune response, the pseudotyped retrovirus-like particle and retroviral vector of the invention are useful tools for the prevention and/or treatment of autoimmune disease.

Autoimmune diseases include in particular acute disseminated encephalomyelitis, acute hemorrhagic leukoencephalitis, Addison's disease, Agammaglobulinemia, Alopecia areata, amyotrophic lateral sclerosis, ankylosing spondylitis, antiphospholipid syndrome, antisynthetase syndrome, atopic allergy, autoimmune aplastic anemia, autoimmune cardiomyopathy, autoimmune enteropathy, autoimmune hemolytic anemia, autoimmune hepatitis, autoimmune inner ear disease, autoimmune lymphoproliferative syndrome, autoimmune peripheral neuropathy, autoimmune pancreatitis, autoimmune polyendocrine syndrome, autoimmune progesterone dermatitis, autoimmune thrombocytopenic purpura, autoimmune urticaria, autoimmune uveitis, Balo disease, Balo concentric sclerosis, Bechets syndrome, Berger's disease, Bickerstaff's encephalitis, Blau syndrome, bullous pemphigoid, Castleman's disease, celiac disease, chronic inflammatory demyelinating polyneuropathy, chronic recurrent multifocal osteomyelitis, Churg-Strauss syndrome, cicatricial pemphigoid, Cogan syndrome, cold agglutinin disease, complement component 2 deficiency, cranial arteritis, CREST syndrome, Crohn's disease, Cushing's syndrome, cutaneous leukocytoclastic angiitis, Dego's disease, Dercum's disease, dermatitis herpetiformis, dermatomyositis, diabetes mellitus type 1, diffuse cutaneous systemic sclerosis, Dressler's syndrome, discoid lupus erythematosus, eczema, enthesitis-related arthritis, eosinophilic fasciitis, eosinophilic gastroenteritis, epidermolysis bullosa acquisita, erythema nodosum, essential mixed cryoglobulinemia, Evan's syndrome, firodysplasia ossificans progressiva, fibrosing aveolitis, gastritis, gastrointestinal pemphigoid, giant cell arteritis, glomerulonephritis, goodpasture's syndrome, Grave's disease, Guillain-Barré syndrome (GBS), Hashimoto's encephalitis, Hashimoto's thyroiditis, hemolytic anaemia, Henoch-Schonlein purpura, herpes gestationis, hypogammaglobulinemia, idiopathic inflammatory demyelinating disease, idiopathic pulmonary fibrosis, idiopathic thrombocytopenic purpura, IgA nephropathy, inclusion body myositis, inflammatory demyelinating polyneuropathy, interstitial cystitis, juvenile idiopathic arthritis, juvenile rheumatoid arthritis, Kawasaki's disease, Lambert-Eaton myasthenic syndrome, leukocytoclastic vasculitis, lichen planus, lichen sclerosus, linear IgA disease (LAD), Lou Gehrig's disease, lupoid hepatitis, lupus erythematosus, Majeed syndrome, Meniere's disease, microscopic polyangiitis, Miller-Fisher syndrome, mixed connective tissue disease, morphea, Mucha-Habermann disease, multiple sclerosis, myasthenia gravis, myositis, neuropyelitis optica, neuromyotonia, ocular cicatricial pemphigoid, opsoclonus myoclonus syndrome, ord thyroiditis, palindromic rheumatism, paraneoplastic cerebellar degeneration, paroxysmal nocturnal hemoglobinuria (PNH), Parry Romberg syndrome, Parsonnage-Turner syndrome, pars planitis, pemphigus, pemphigus vulgaris, permicious anemia, perivenous encephalomyelitis, POEMS syndrome, polyarteritis nodosa, polymyalgia rheumatica, polymyositis, primary biliary cirrhosis, primary sclerosing cholangitis, progressive inflammatory neuropathy, psoriasis, psoriatic arthritis, pyoderma gangrenosum, pure red cell aplasia, Rasmussen's encephalitis, Raynaud phenomenon, relapsing polychondritis, Reiter's syndrome, restless leg syndrome, retroperitoneal fibrosis, rheumatoid arthritis, rheumatoid fever, sarcoidosis, Schmidt syndrome, Schnitzler syndrome, scleritis, scleroderma, Sjögren's syndrome, spondylarthropathy, Still's disease, stiff person syndrome, subacute bacterial endocarditis, Susac's syndrome, Sweet's syndrome, Sydenham chorea, sympathetic ophthalmia, Takayasu's arteritis, temporal arteritis, Tolosa-Hunt syndrome, transverse myelitis, ulcerative colitis, undifferentiated connective tissue disease, undifferentiated spondylarthropathy, vasculitis, vitiligo and Wegener's granulomatosis.

As used herein, the term "cancer" encompasses any type of cancer, such as glioblastoma, neuroblastoma, B cell lymphoma, T cell lymphoma, breast cancer, hepatocellular carcinoma, cancer arising from hematopoietic cells, including leukemia, in particular B-CLL (B-cell Chronic lymphocytic leukaemia), CML (Chronic Myelogenous Leukemia) or T cell based leukemia such as ATL (acute T cell leukemia), ALL (Acute Lymphoblastic Leukemia), AML (Acute Myeloid Leukemia) and/or melanoma.

Therapeutic Applications

The present invention also relates to a pseudotyped retrovirus-like particle or retroviral vector as defined above for use as a medicament, preferably in immune therapy gene therapy and/or vaccination.

Gene therapy is a therapy using gene(s) as a medicament, which may for example be obtained by delivering in a cell a gene of interest and/or correcting gene(s) of interest at the endogenous site. In gene therapy, a nucleic acid comprising the gene(s) of interest is delivered into the cells of a patient, the expression of the protein(s) encoded by gene(s) of interest and/or the correction of the gene(s) of interest thereby allowing preventing and/or treating a disease.

Said gene(s) of interest may be present in the RNA molecule comprised in the retroviral vector according to the invention.

The correction of gene(s) may be carried out by the CRISPR/CAS system.

Immune therapy, also called immunotherapy, is a therapy based on modulating the activity of the immune system (for example, stimulation or inhibition) to prevent and/or treat a disease.

In the context of the present invention, immunotherapy consists in modulating the activity of only specific targeted immune cells, by using the retrovirus-like particle or retroviral vector according to the invention, and optionally selectively transducing said target immune cells. For example, the retroviral vector may be used to activate B cells, such as make them differentiate in plasma cells, and optionally transduced them with a nucleic acid encoding an ectopic antibody against an infectious agent (for example against HIV, HCV or HBC).

Immune therapy also comprises T cell therapy. In T cell therapy, T cells might in addition to being modulated for their function be more permissive to gene transfer, for example for the T cell receptor (CAR) gene transfer.

Adoptive T cell therapy is a therapy wherein T cells are transfused to a subject in need therefore. In the context of the present invention, the activity of said T cells may have been modulating prior to the transfusion, by using the retrovirus-like particle or retroviral vector according to the invention.

In the context of the present invention, vaccination consists in displaying at the surface of the retrovirus-like particle or retroviral vector specific viral epitopes that will be targeted to and activate at the same time the Antigen presenting cells (for example macrophages) that will subsequently present the epitopes to the immune system (T and B cells).

The present invention also relates to a pseudotyped retrovirus-like particle or retroviral vector as defined above for use as a medicament, wherein said pseudotyped retrovirus-like particle or retroviral vector selectively modulates the activity of target cells and optionally selectively transduces target cells.

The present invention particularly relates to a pseudotyped retrovirus-like particle or retroviral vector for use as defined above, in the prevention and/or treatment of a disease as defined above in the section "Prevention and/or treatment of a disease".

Said disease is for example an immune disease (for example an auto-immune disease), cancer, genetic disease, allergic disease, inflammatory disease, infectious disease (in particular bacteria and/or virus infection), metabolic disease, neurological disease (such as neural dystrophy, Alzheimer disease, Parkinson disease, Huntington disease), muscular disease and their combinations.

In one embodiment, the pseudotyped retrovirus-like particle or retroviral vector is used for improving DC (Dendritic Cell) vaccine, for example, by co-displaying DC cell specific ligand (such as CD11b) and GM-SCF (Granulocyte-Macrophage Colony-Stimulating Factor) on the surface of the vector, for protein or gene transfer.

In an advantageous embodiment, T cell activation is coupled with T cell specific gene transfer, which significantly enhanced the gene transfer efficiency in resting T cells, for example in T cell-based gene therapy. Efficient in vivo gene transfer into T cell subset is a revolution in the gene and cell therapy field, since it allows omitting ex vivo culture and transduction processes which induce high costs for the clinical application. Moreover, leaving the cells into their normal micro-environment in vivo allows them to conserve their phenotype and to persist long-term into a patient (eg. tumor specific CD8 cytotoxic cells).

In another embodiment, the invention may be used to enhance selective gene delivery into resting B lymphocytes, for example in B cell-based gene therapy, such as immunotherapy that allows the B cells to produce neutralizing antibodies against infectious agent(s) or allows B cell secretion of recombinant proteins that are tolerated by the immune system since B cell can act as tolerogenic cells.

Moreover, displaying one or more cytokines on the surface of the pseudotyped retrovirus-like particle or retroviral vector may induce the T cell subset differentiating into phenotypes like TSCM or TCM, which might persist long term in vivo.

In another embodiment, the invention may be used for in vivo expansion of (autologous) anti-cancer natural killer cells, for cancer therapy.

In one embodiment, the pseudotyped retrovirus-like particle or retroviral vector is used to induce apoptosis of a defined cell subset by co-displaying an apoptosis ligand and a tumor or immune cell specific targeting domain.

The pseudotyped retrovirus-like particle or retroviral vector may be provided in the form of a pharmaceutical composition.

The pharmaceutical composition is preferably as defined above in the section of the same name.

The present invention also concerns a method for treating a subject in need thereof comprising administering a therapeutically effective amount of a pseudotyped retrovirus-like particle or retroviral vector as defined above, preferably in the frame of an immune therapy, gene therapy and/or vaccination.

The present invention also relates to a method for treating a subject in need thereof comprising administering a therapeutically effective amount of a pseudotyped retrovirus-like particle or retroviral vector as defined above, wherein said pseudotyped retrovirus-like particle or retroviral vector selectively modulates the activity of target cells and optionally selectively transduces target cells.

The present invention also concerns a method for preventing and/or treating a disease, comprising administering to a subject in need thereof a therapeutically effective amount of a pseudotyped retrovirus-like particle or retroviral vector as defined above, wherein said disease is preferably as defined above.

Any suitable method of administration known from one skilled in the art may be used. In particular, the pseudotyped retrovirus-like particle or retroviral vector according to the invention may be administered by the oral route, the parenteral route (preferably by intravenous injection), the medullar route, in particular the intra-femur (such as in the bone marrow cavity) or humerus medullar route injection and/or local intra-tumour injection.

When the parenteral route is selected, the pseudotyped retrovirus-like particle or retroviral vector may be in the form of injectable solution or suspension, for example conditioned in an ampoule or flask.

The pseudotyped retrovirus-like particle or retroviral vector is preferably used or administered in a therapeutically effective amount.

A "therapeutically effective amount" refers to a quantity of pseudotyped retrovirus-like particle or retroviral vector that confers a therapeutic effect on the treated subject. The therapeutic effect may be objective (i.e., measurable by some test or marker) or subjective (i.e. subject gives an indication of or feels an effect). As known from the skilled person, effective doses will vary depending on route of administration, the size and/or weight of the subject, as well as the possibility of co-usage with other agents.

The term "comprising" as used herein encompasses the term "consisting of".

The present invention will be further illustrated in view of the following examples and figures.

All references cited herein, including journal articles or abstracts, published or unpublished patent application, issued patents or any other references, are entirely incorporated by reference herein, including all data, tables, figures and text presented in the cited references.

BRIEF DESCRIPTION OF THE SEQUENCES

SEQ ID NO: 1 corresponds to a nucleic acid sequence encoding a truncated and mutated (Y481A, R533A, S548L, F549S) MV H protein (HcDelta18) fused to Designed Ankyrin Repeat Protein (DARPin)-29.2 specific for human CD4.

SEQ ID NO: 2 corresponds to the amino acid sequence encoded by sequence SEQ ID NO: 1.

SEQ ID NO: 3 corresponds to a nucleic acid sequence encoding a truncated and mutated (E501A, W504, Q530A, E533A) NiV G protein (GcΔ34) fused to a single chain antibody directed to human CD8 (scFvC8-Vh1) linked with an additional $(G_4S)_3$ linker.

SEQ ID NO: 4 corresponds to the amino acid sequence encoded by sequence SEQ ID NO: 3.

SEQ ID NO: 5 corresponds to a nucleic acid sequence encoding a truncated and mutated (E501A, W504, Q530A, E533A) NiV G protein (GcΔ34) fused to IL-7.

SEQ ID NO: 6 corresponds to the amino acid sequence encoded by sequence SEQ ID NO: 5.

SEQ ID NO: 7 corresponds to a nucleic acid sequence encoding a truncated and mutated (E501A, W504, Q530A, E533A) NiV G protein (GcΔ34) fused to a designed ankaryin repeat protein (DARPin) directed against human EpCAM.

SEQ ID NO: 8 corresponds to the amino acid sequence encoded by sequence SEQ ID NO: 7.

SEQ ID NO: 9 corresponds to the full length amino acid sequence of the Nipah virus envelope glycoprotein G.

SEQ ID NO: 10 corresponds to the full length amino acid sequence of the measles virus envelope glycoprotein H.

SEQ ID NO: 11 corresponds to the full length amino acid sequence of the Nipah virus envelope glycoprotein F.

SEQ ID NO: 12 corresponds to the full length amino acid sequence of the measles virus envelope glycoprotein F.

SEQ ID NO: 13 corresponds to a nucleic acid sequence encoding a truncated and mutated MeV H protein (HcΔ15) fused to IL-7.

SEQ ID NO: 14 corresponds to the amino acid sequence encoded by sequence SEQ ID NO: 13.

SEQ ID NO: 15 corresponds to the amino acid sequence of the measles virus F protein truncated by 30 amino acids in the cytoplasmic tail (FcΔ30).

SEQ ID NO: 16 corresponds to the amino acid sequence of the Nipah virus F protein truncated by 22 amino acids in the cytoplasmic tail (FcΔ22).

BRIEF DESCRIPTION OF THE FIGURES

FIG. 10: Neutralization of NiV glycoprotein pseudotyped LVs. CHO-EpCAM or CHO-Ephrin-B2 cells were transduced with NiVmutEpCAM-LV (circle), MVEpCAM-LV (square), NiVwt-LV (triangle), or VSVG-LV (diamond) at an MOI of 0.4 after incubation with serial dilutions of pooled human serum (IVIG) for 2 h at 37° C. After 72 h, GFP+ cells were determined by flow cytometry and the number of GFP+ cells relative to untreated control is shown (n=3).

Figure 1:
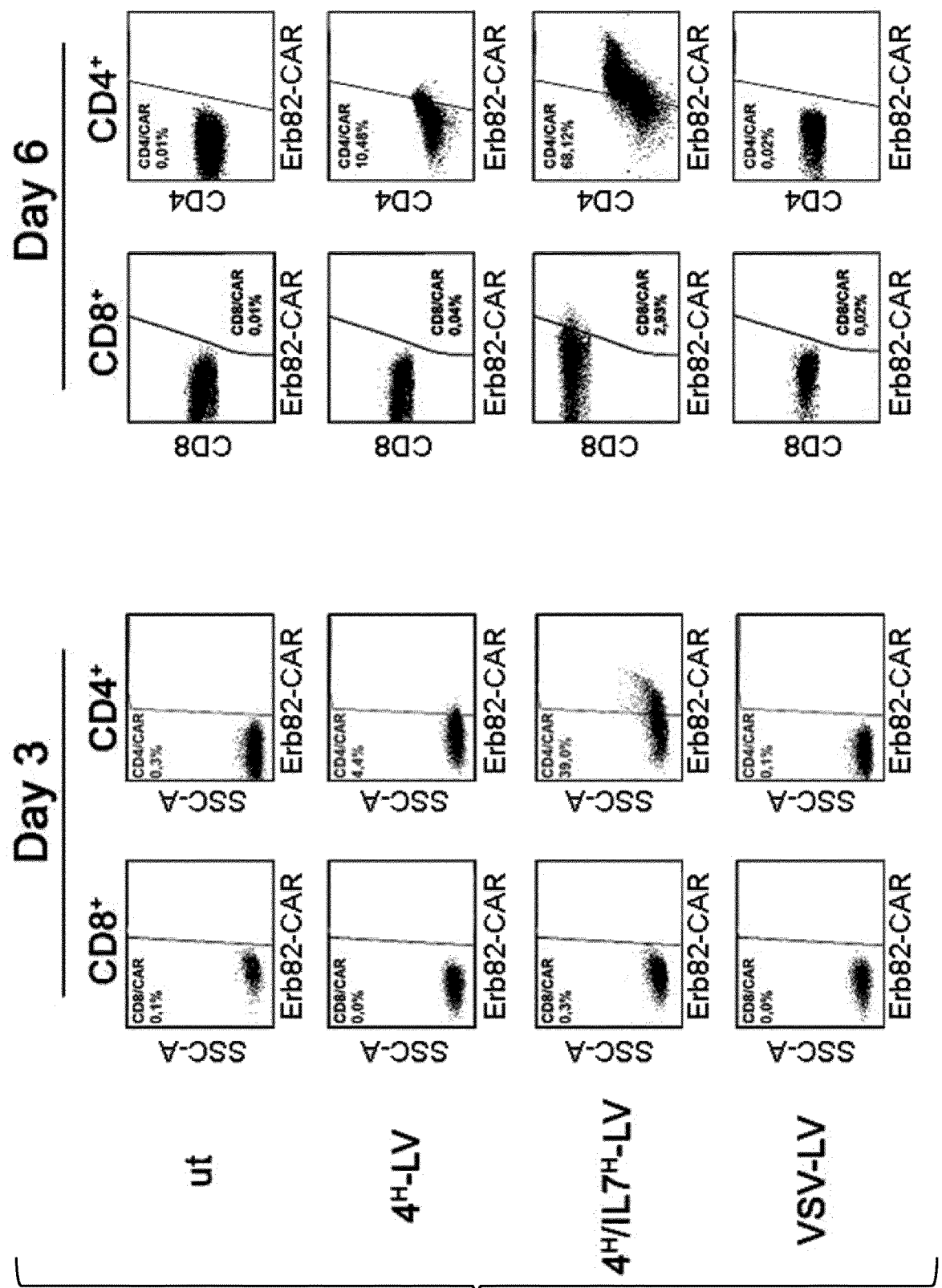
FIG. 1: Efficient and stable ErbB2-CAR gene transfer into resting CD4$^+$ T cells by $4^H$/IL7$^H$-LV. To assess if $4^H$/IL7$^H$-LV can efficiently transfer therapeutic genes (ErbB2 specific CAR, ErbB2-CAR) into resting T cells, freshly isolated CD3$^+$ T cells were transduced with $4^H$-LV or $4^H$/IL7$^H$-LV. Cells transduced with VSV-LV or left untransduced (ut) were used as negative controls. Three days later, half of the transduced cells were analyzed by FACS to determine the percentage of ErbB2-CAR$^+$ cells in the CD4- or CD8-gated cells. To confirm stable ErbB2-CAR expression, the other half of the transduced cells was further cultivated in the presence of anti-CD3/anti-CD28/IL-2 stimulus, after a washing step, for additional three days. Then, the percentages of CD4$^+$/ErbB2$^+$ cells and CD8$^+$/ErbB2$^+$ cells were determined by FACS.

NOD/SCID gc−/− mouse were injected with cord blood T cells and 2 months upon engraftment (20% T cell reconstitution), 100 microliters of $4^H$/IL$7^H$-LV (1E6 IU) or $4^H$/IL$7^H$-LV were injected by IV. Two weeks after injection of the vectors, the mice were sacrificed and the splenocytes were evaluated for % of CD71+CD4+ T cells (activation marker).

EXAMPLES

Material and methods
Generation of the Constructs

The plasmid pHL3-Ac1 coding for truncated and mutated MV Hc$\Delta$18mut protein and for a (G$_4$S)$_3$ linker (L3) between H and the His-tagged DARPin Ac1 was generated by inserting the PCR amplified coding sequence of the EpCAM specific DARPin Ac1 (Stefan et al. 2011) from pQE30ss_Ac1_corr into the backbone of plasmid pHL3-HRS3opt2#2(Friedel et al. 2015) via Sfil/NotI.

All plasmids encoding Nipah virus G protein variants were derived from plasmid pCAGGS-NiV-codonop-Gn. The coding sequence for the Ac1 targeting domain was fused to the C-terminus of the G protein reading frame by PCR amplification of each fragment and simultaneously introducing a common Agel restriction site, which was used for ligation resulting in plasmid pCAGGS-NiV-G-DARPin-Ac1. All other targeting domains were exchanged via Agel/NotI. Truncations of the G protein cytoplasmic tail were introduced by PCR amplification of the G protein reading frame and insertion of the PCR fragments into pCAGGS-NiV-G-DARPin-Ac1 resulting in plasmids pCAGGS-NiV-Gc$\Delta$33-DARPin-Ac1 and pCAGGS-NiV-Gc$\Delta$34-DARPin-Ac1.The His-tagged G and Gc$\Delta$34 proteins were generated by PCR amplification from pCAGGS-NiV-codonop-Gn. The fragments were cloned via PacI/NotI restriction into the plasmid backbone of pCAGGS-NiV-G-DARPin-Ac1 resulting in pCAGGS-NiV-G-His and pCAGGS-NiV-GcΔ34-His, respectively. Mutations interfering with natural receptor recognition were introduced into the NiV-GcΔ34-DARPin-Ac1 protein coding sequence by site-directed mutagenesis. Each mutation was generated by amplification of two fragments carrying the designated mutation with homologous regions at the mutation site. These fragments were fused and amplified by a flanking primer pair. Resulting fragments were cloned into pCAGGS-NiV-GcΔ34-DARPin-Ac1 via RsrII/AgeI, generating the plasmids pCAGGS-NiV-GcΔ34EpCAMmut.

For the generation of the NiV-F variants, the coding sequences for FcΔ22 and FcΔ25 were amplified from pCAGGS-NiV-F and cloned via PacI/SacI restriction into the plasmid backbone of pCAGGS-NiV-codonop-Gn resulting in the plasmids pCAGGS-NiV-FcΔ22 and pCAGGS-NiV-FcΔ25. AU1 tagged NiV-F variants used for Western blot analysis of vector particles were generated by amplifying the NiV-F variants from pCAGGS-NiV-F and simultaneously adding the AU1 tag N-terminally. The resulting PCR fragments were cloned via PacI/SacI restriction digest into the backbone of pCAGGS-NiV-codonop-Gn, resulting in the plasmids pCAGGS-AU1-NiV-F, pCAGGS-AU1-NiV-FcΔ22, and pCAGGS-AU1-NiV-FcΔ25.

Vector Production

Vector particles were generated by transient transfection of HEK-293T cells using polyethylenimine (PEI). Twenty-four hours before transfection, $2.5 \times 10^7$ cells were seeded into a T175 flask. On the day of transfection, the cell culture medium was replaced by 10 ml DMEM with 15% FCS and 3 mM L-glutamine. The DNA mix was prepared by mixing 35 μg of total DNA with 2.3 ml of DMEM without additives.

For example, following optimization of G to F ratios, 0.9 μg of plasmid encoding for GcΔ34DARPin/scFv variants was mixed with 4.49 μg plasmid encoding for F variants. 14.4 μg of HIV-1 packaging plasmid pCMVΔR8.9 and 15.1 μg of transfer-LV plasmids were used. The transfection reagent mix was prepared by mixing 140 μl of 18 mM PEI solution in H2O with 2.2 ml DMEM without additives. This solution was mixed with the DNA mix, vortexed, incubated for 20 minutes at room temperature and added to the HEK-293T cells, resulting in DMEM with 10% FCS, 2 mM L-glutatmine in total. 24 h later, the medium was exchanged with DMEM with 10% FCS, 2 mM L-glutamine in order to remove remaining PEI/DNA complexes. At day two post transfection, the cell supernatant containing the lentiviral vectors was filtered through a 0.45 μm filter. If needed, vector particles were purified by centrifugation at 450×g for 24 h over a 20% sucrose cushion. The pellet was resuspended in phosphate-buffered saline (PBS). For transduction, $8 \times 10^3$ of CHO-EpCAM and SK-OV-3 cells or $2 \times 10^4$ Molt4.8 and Raji cells were seeded into a single well of a 96-well-plate and transduced on the next day. When needed, medium of cells was replaced with medium containing different concentrations of Bafilomycin A1 (Santa Cruz Biotechnology, Inc, Dallas, USA) and cells were pre-incubated 30 min at 37° C. before vector was added. For titration, at least four serial dilutions of vector particles were used. After 72 h, the percentage of green fluorescentprotein (GFP)-positive cells was determined by flow cytometry. Transducing units/ml (t.u./ml) was calculated by selecting the dilutions showing linear correlation betweendilution factor and number of GFP-positive cells (number of transduced cells/volume of vector in μl/0.001).

Figure 7:
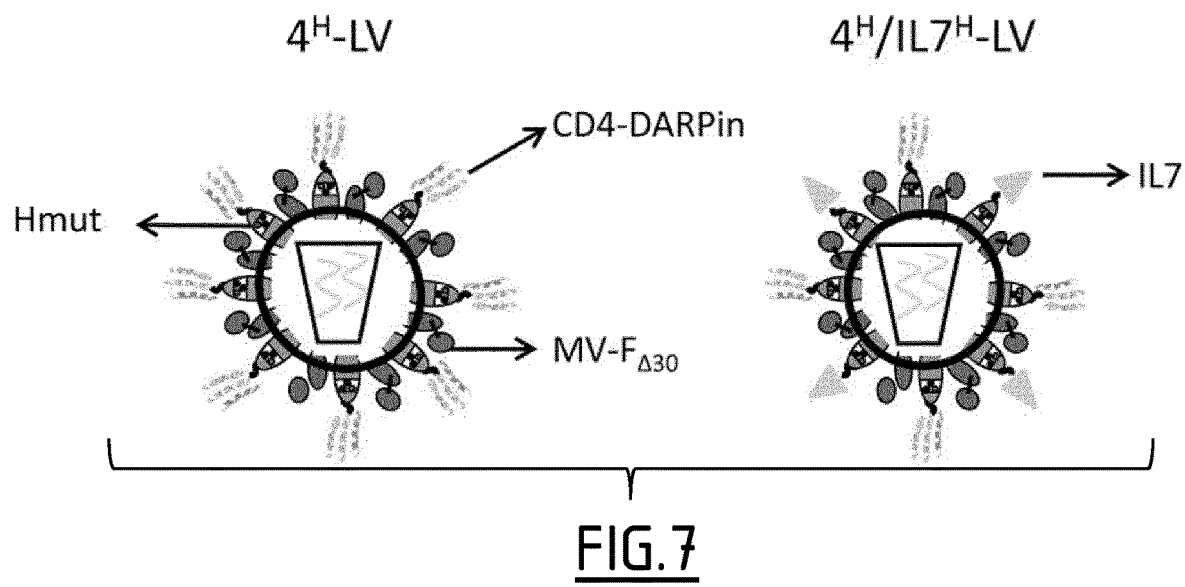
FIG. 7: Schematic representation of pseudotyped lentiviral vectors (LV). $4^H$-LV is a CD4-targeted LV based on MeV glycoprotein pseudotypes. $4^H$/IL$7^H$-LV is a IL7-displaying CD4-targeted LV based on MV glycoprotein pseudotypes. The envelope glycoprotein H (MV-H) is truncated at its cytoplasmic tail, for example by 15, 18, or 20 amino acids and at least two out of four point mutations (Y481A, R533A, S548L, and F549S) are introduced to blind its natural receptor recognition of SLAM and CD46, thereby resulting in the envelope glycoprotein Hmut. Afterwards, a targeting domain (for example CD4-DARPin) and/or a cytokine (for example IL7) are fused to the mutant H (Hmut), with or without a linker. The MV envelope glycoprotein F is truncated at its cytoplasmic tail by 30 amino acids (MV-F$_{\Delta 30}$).
Figure 8:
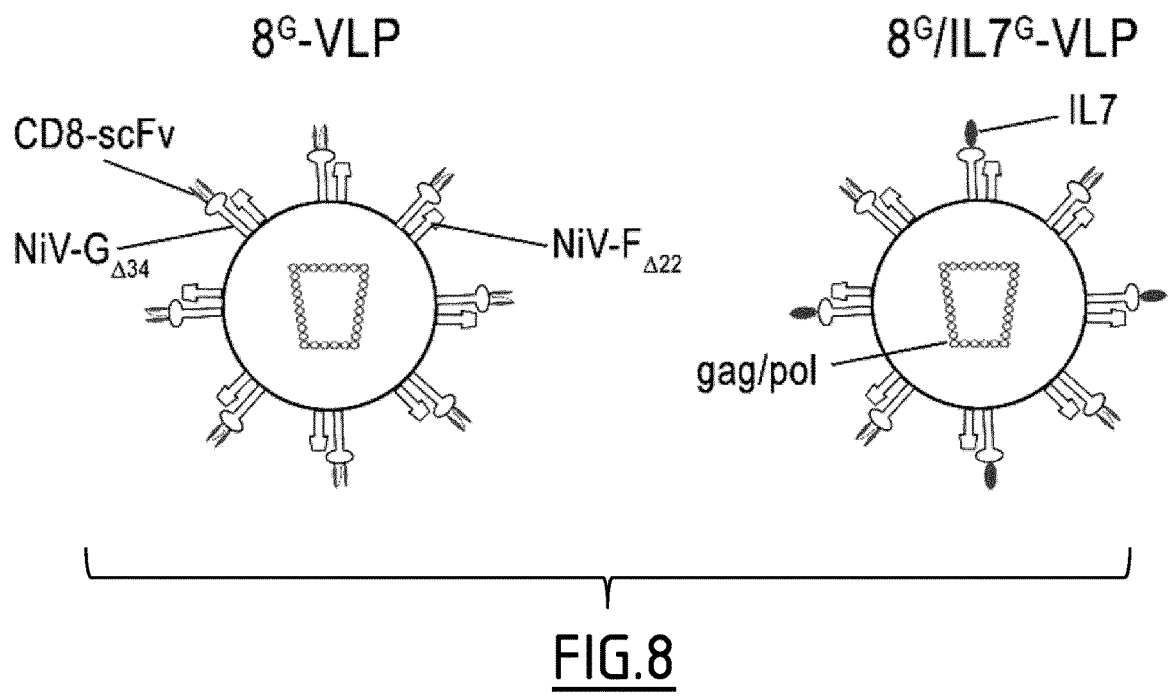
FIG. 8: Schematic representation of pseudotyped virus-like particles (VLP). $8^G$-VLP is a CD8-targeted VLP based on NiV glycoprotein pseudotypes. $8^G$/IL$7^G$-VLP is a IL7-displaying CD8-targeted VLP based on NiV glycoprotein pseudotypes. The NiV-G envelope glycoprotein is truncated at its cytoplasmic tail by 34 amino acids ($\Delta$34) and four point mutations (E501A, W504A, Q530A, and E533A) are introduced to blind its natural receptor recognition of Ephrin-B2/B3, thereby resulting in the envelope glycoprotein NiV-G$_{\Delta 34}$. Afterwards, a targeting domain (CD8-scFv) and/or a cytokine (IL7) are fused to the mutant G protein (NiV-G$_{\Delta 34}$) with or without a linker. The NiV envelope glycoprotein F is truncated at its cytoplasmic tail by 22 amino acids (NiV-F$_{\Delta 22}$).

Schematic presentations of the pseudotyped retrovirus-like particle or retroviral vector according to the invention are depicted in FIGS. 7 and 8.

Example 1

Selective Activation of CD4+ T Cells

In order to activate $CD4^+$ but not $CD8^+$ lymphocytes, VLPs were generated that display a CD4-specific DARPin as targeting ligand and IL-7 as activation domain on the MV H protein along with the fusion protein (F) resulting in the $4^H/IL7^H$-VLP (comprising proteins of sequence SEQ ID NO: 2, 14 and 15). To generate the particles, a transfection protocol was established. Briefly, 0.45 μg of pCG-Hmut-CD4-DARPin (Zhou et al., J Immunol, 2015), 0.45 μg of pCG-HΔ15-IL7 (provided by Els Verhoeyen), 4.7 μg of pCG-FcΔ30 (Funke et al., Molecular therapy, 2008), 14.4 μg of HIV-1 packaging plasmid pCMVΔR8.9 (Funke et al., Molecular therapy, 2008), and 15.1 μg of pCG-1 were used for transfection of HEK293T cells in one T175 flask. After harvesting, the vector particles were further concentrated via ultracentrifugation. Titers of ~$10^7$ to/ml were obtained for LVs and titers of ~1.5 ug p24/ml were obtained for VLPs.

Figure 3:
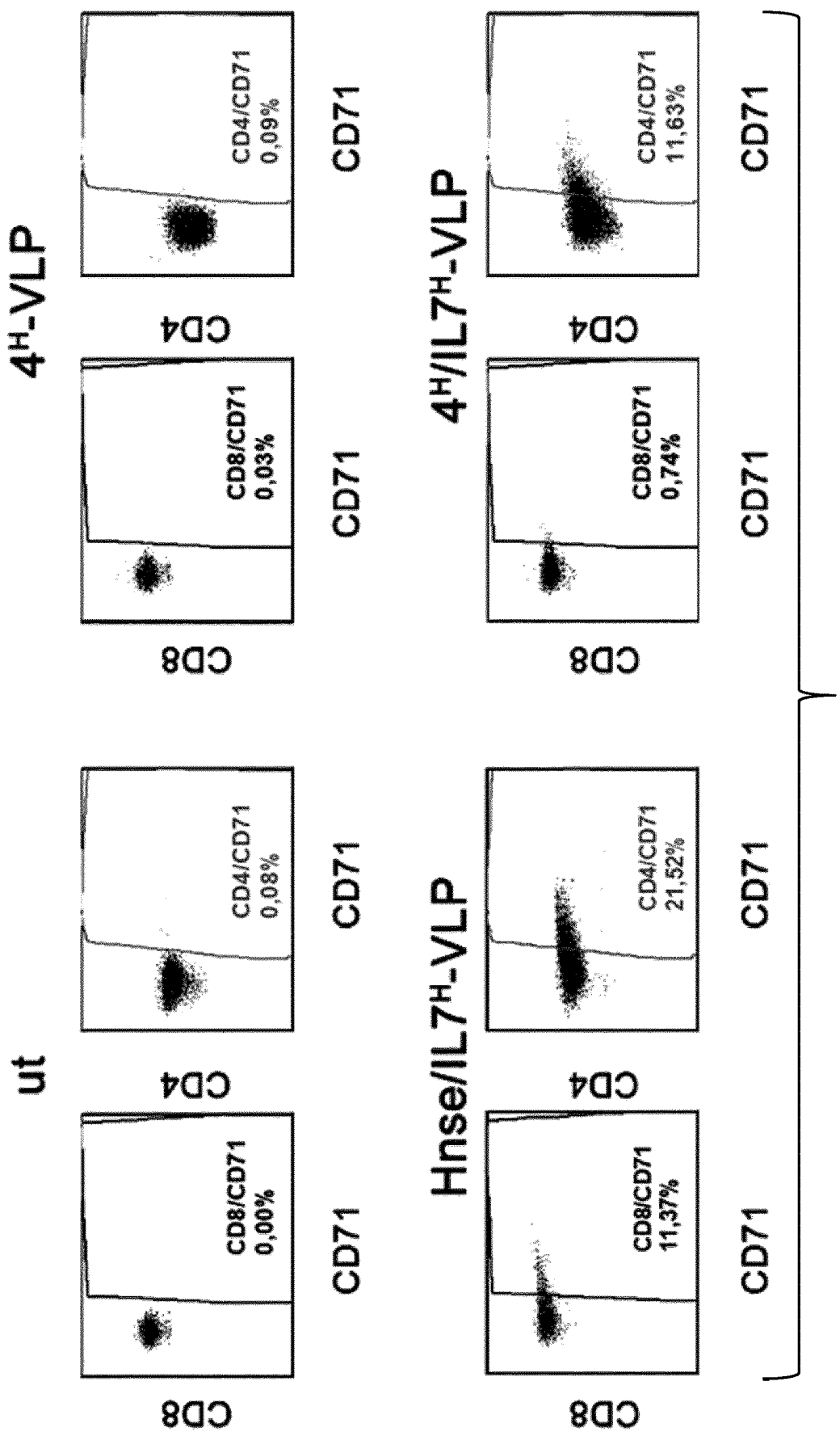
FIG. 3: Selective activation of CD4$^+$ T cells by $4^H$/IL7$^H$-VLP. Freshly isolated CD3$^+$ T cells were left untransduced (ut) or transduced with different types of VLPs pseudotyped with CD4-DARPin-Hmut ($4^H$-VLP), CD4-DARPin/IL7-Hmut ($4^H$/IL7$^H$-VLP) or IL7-Hnse (Hnse/IL7$^H$-VLP). Three days later the cells were stained by CD8, CD4, and CD71 antibodies. The CD71 expression in the CD4- or CD8-gated T cells is shown.
Figure 4:
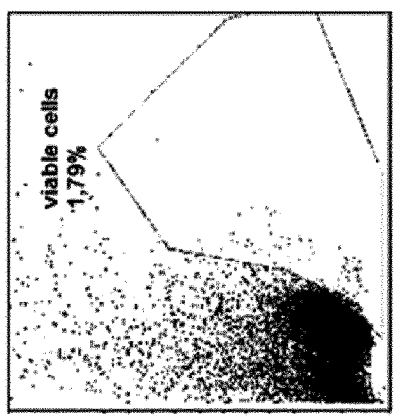
FIG. 4: Functionally displayed IL7 on the targeted-VLPs promote T cell survival. The forward/side scatter profiles of adult resting CD3$^+$ T cells that were incubated for 6 days with virus-like particles (VLP) pseudotyped with CD4-targeted MV-H ($4^H$-VLP), CD8-targeted MV-H ($8^H$-VLP), IL7-displaying CD4-targeted MV-H ($4^H$/IL7$^H$-VLP), or IL7-displaying CD8-targeted MV-H ($8^H$/IL$7^H$-VLP). Cells cultivated in the medium alone (untransduced, ut) or in the presence of 15 ng/ml IL7 were used as controls. The percentage of viable cells is indicated in each dot blot.
Figure 4:
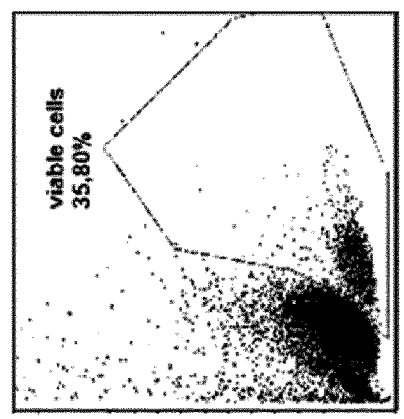
Figure 4:
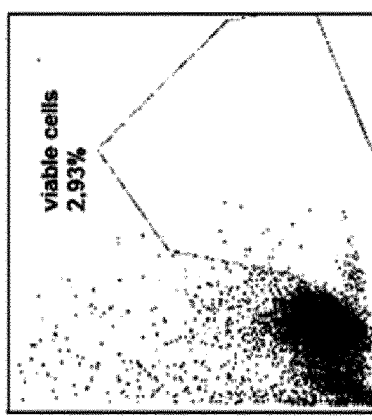
Figure 4:
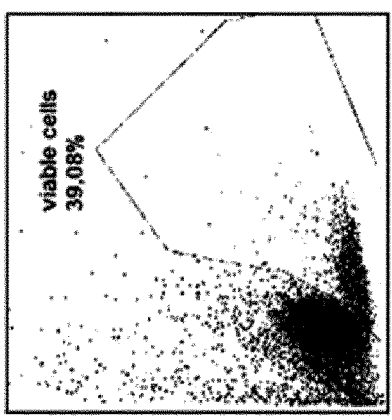
Figure 4:
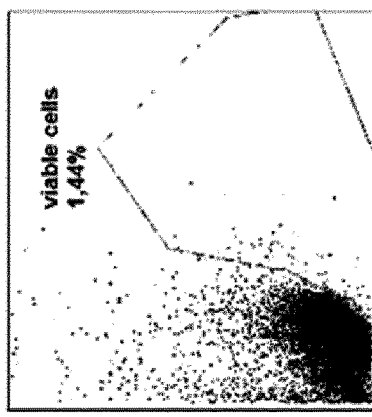
Figure 4:
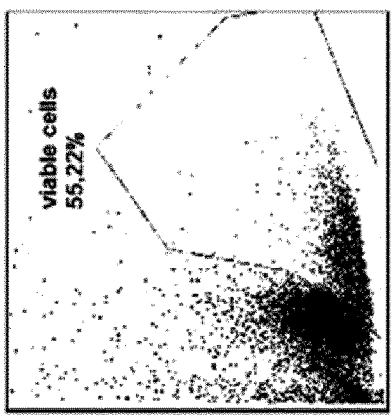

The function of $4^H/IL7^H$-VLP was demonstrated on freshly isolated resting T cells. Briefly, $CD3^+$ T cells were isolated by negative selection using Pan T cell isolation kit (Miltenyi Biotech) from adult peripheral blood. Subsequently, the cells were incubated with $4^H/IL7^H$-VLP in the absence of any stimulation. Three days later, the $CD4^+$ T cells but not the $CD4^-$ T cells in the cell culture were activated, as confirmed by FACS analysis for the CD71 activation maker (FIG. 3). Non-targeted particles displaying IL-7 activated both, $CD4^+$ T cell and $CD4^-$ T cells. IL-7 is known to be a T cell survival cytokine. Therefore, it was demonstrated that all IL7-displaying VLPs were as effective as recombinant human IL-7 at preventing the death of primary T cells, while most of the resting T cells placed in culture were dead after six days in the presence of conventional IL7-deficient VLP particles (FIG. 4).

Figure 5:
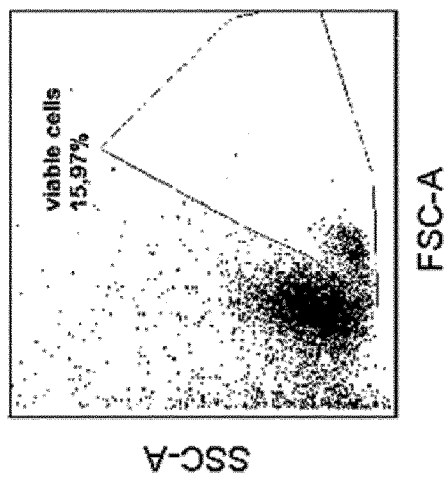
FIG. 5: Functionally displayed IL7 on the CD4-targeted LVs promote T cell survival. The forward/side scatter profiles of adult resting CD3$^+$ T cells that were incubated for 6 days with lentiviral vectors (LV) pseudotyped with VSVG (VSV-LV), MV-Hmut (Hnse-LV), CD4-targeted MV-H ($4^H$-LV), or IL7-displaying CD4-targeted MV-H ($4^H$/IL$7^H$-LV). Cells cultivated in the medium alone (untransduced, ut) or in the presence of 15 ng/ml IL7 were used as controls. The percentage of viable cells is indicated in each dot blot.
Figure 5:
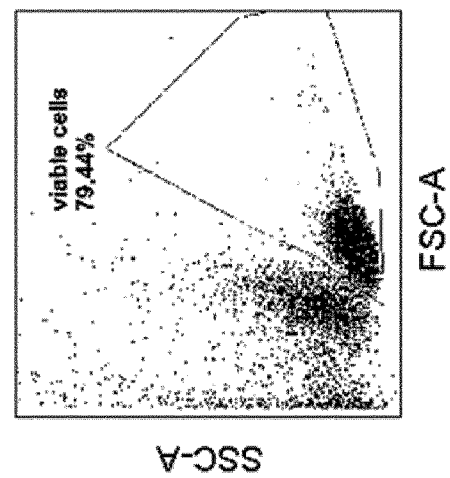
Figure 5:
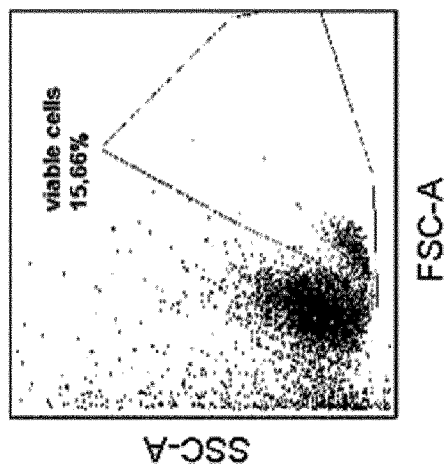
Figure 5:
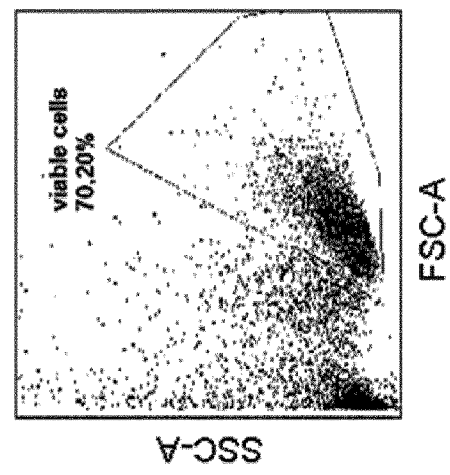
Figure 5:
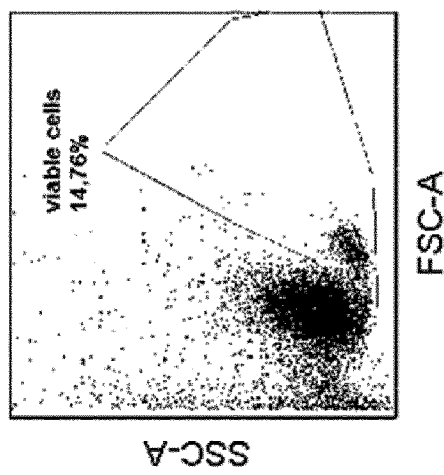
Figure 5:
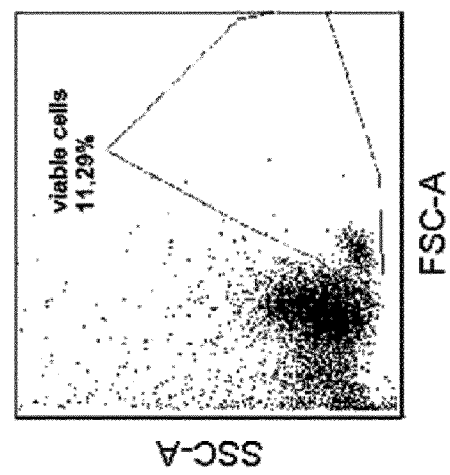
Figure 6:
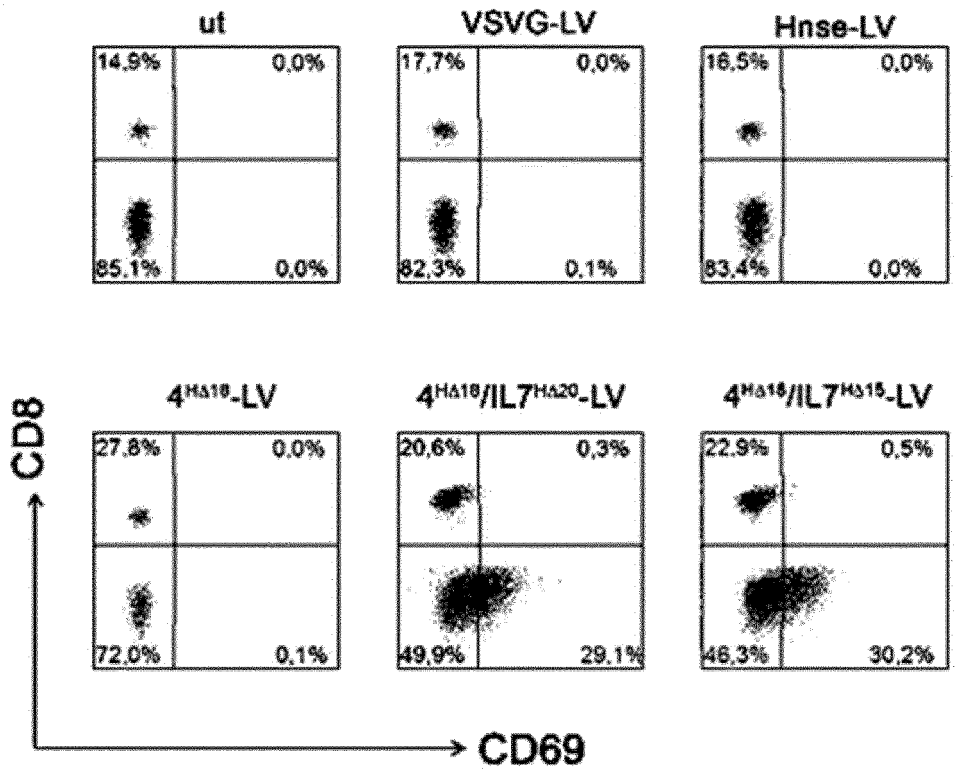
FIG. 6: Selective activation of CD4$^+$ T cells by $4^H$/IL$7^H$-LV. Freshly isolated CD3$^+$ T cells were left untransduced (ut) or transduced with different types of LVs pseudotyped with CD4-DARPin-Hmut ($4^{H\Delta 18}$-LV), Hnse (Hnse-LV), or VSVG (VSVG-LV). Here IL7 was displayed on two different versions of Hmut, either with 20 amino acids C-truncated (H$\Delta$20) or with 15 amino acids C-truncated (H≠15). Accordingly, two types of $4^H$/IL$7^H$-LV were produced and transduced the resting T cells. Three days later the cells were stained by CD3, CD8, CD69, and CD71 antibodies. The activation markers CD69 and CD71 expression in CD8$^+$ and CD8$^-$ (CD4$^+$) cells is shown.
Figure 6:
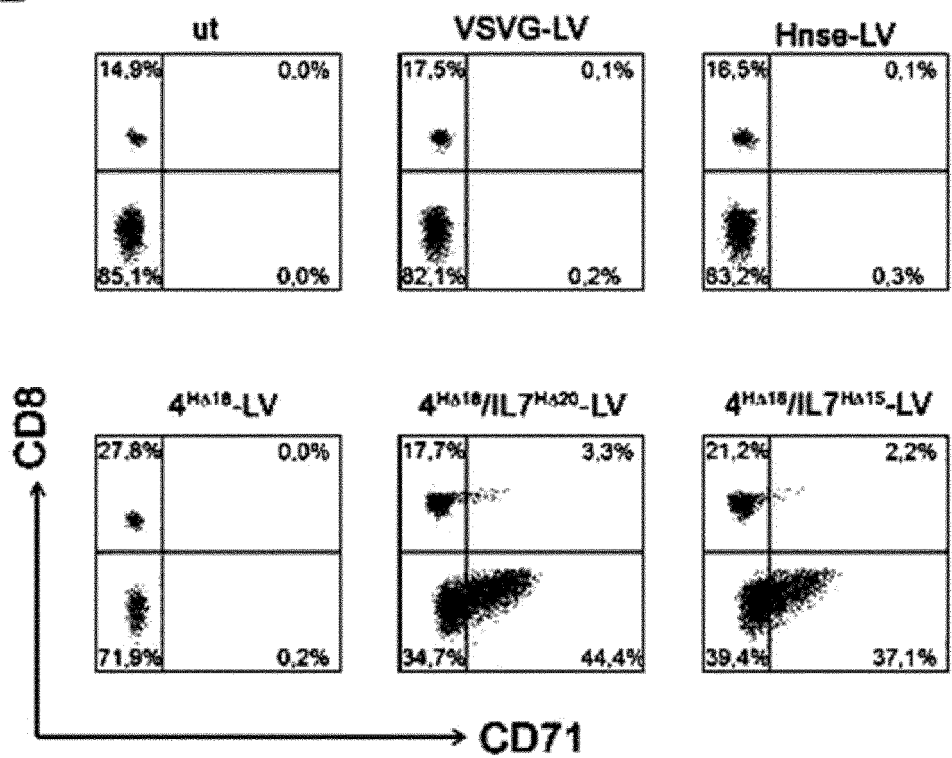

The capacity of promoting T cell survival and selectively activating $CD4^+$ T cells was also acquired by IL7-displaying CD4-targeted LVs ($4^H/IL7^H$-LV). Viral particles were produced as described above, except that pCG-1 was substituted by the transfer plasmid encoding GFP. In addition, in order to test the flexibility of the system and if the function of particles could be enhanced by using other version of Hmut, two different plasmids encoding Hmut-IL7 were used for vector production. pCG-HΔ15-IL7 is with 15 aa cytoplasmic truncation of Hmut-IL7 (for $4^H/IL7^{HΔ5}$-LV production) and pCG-HΔ20-IL7 is with 20 aa cytoplasmic truncation of Hmut-IL7 (for $4^H/IL7^{HΔ20}$-LV production). Without specific indication, IL7-displaying VLP and LV were produced with pCG-HΔ15-IL7. Similar to what was achieved by $4^H/IL7^H$-VLP, when freshly isolated human $CD3^+$ T cells were incubated with the indicated LVs in the absence of stimulation for 6 days, $4^H/IL7^H$-LV significantly promoted T cell survival compared to the parental $4^H$-LV and non-targeted Hnse-LV (FIG. 5). As expected, the highest percentage of viable cells was observed in rhIL-7 treated positive group and the least viable cells were in the VSV-LV transduce or untransduced (ut) groups (FIG. 5). Moreover, $4^H/IL7^H$-LV was as potent as $4^H/IL7^H$-VLP in selectively stimulating its target cell population in the mixed cell culture. As shown in FIG. 6, $4^H/IL7^H$-LV selectively upregulate activation maker CD69 and CD71 expression $CD4^+$ cells but not $CD4^-$ cells. There were no differences between $4^H$/IL7$^{H\Delta15}$-LV and $4^H$/IL7$^{H\Delta20}$-LV in CD4$^+$ T cell stimulation. Therefore, functional IL7-displaying targeted LVs are successfully generated.

Example 2

Delivery of Tumor-Specific Chimeric Antigen Receptors into Resting T Cells

Figure 9:
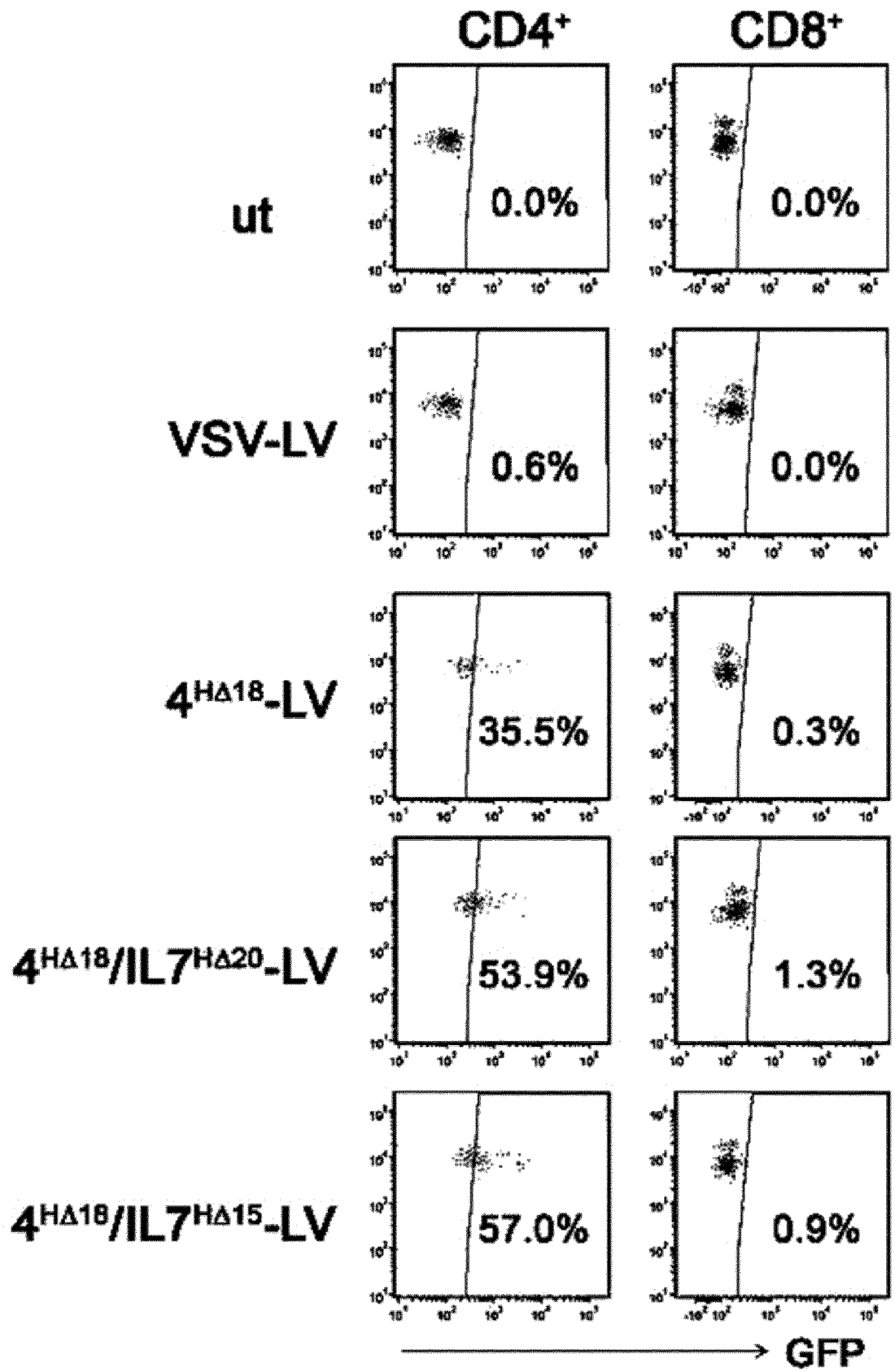
FIG. 9: Efficient and selective transduction of resting CD4$^+$ T cells by $4^H$/IL$7^H$-LV. Freshly isolated CD3$^+$ T cells were left untransduced (ut) or transduced with different types of LVs pseudotyped with CD4-DARPin-Hmut ($4^{H\Delta 18}$-LV), Hnse (Hnse-LV), or VSVG (VSVG-LV). Here IL7 was displayed on two different versions of Hmut, either with 20 amino acids C-truncated (H$\Delta$20) or with 15 amino acids C-truncated (H$\Delta$15). Accordingly, two types of $4^H$/IL$7^H$-LV ($4^{H\Delta 18}$/IL$7^{H\Delta 15}$-LV and $4^{H\Delta 18}$/IL$7^{H\Delta 20}$-LV) were produced and transduced the resting T cells. Three days later the cells were stained by CD3, CD8, and CD4 antibodies. The GFP expression in CD4- or CD8-gated T cells is shown.

Since IL7-displaying vectors triggered the resting T cells activation, it is expected that these cells are permissive for lentiviral transduction. In order to prove it, two versions of $4^H$/IL7$^H$-LV delivering GFP transgene were generated. As shown in FIG. 9, both $4^H$/IL7$^{H\Delta15}$-LV and $4^H$/IL7$^{H\Delta20}$-LV can efficiently and selectively transduce resting CD4$^+$ T cells in the cell mixture.

Chimeric antigen receptors (CARs) are a powerful tool for cancer therapy. So far, T cell subsets must be purified and activated for genetic delivery of CARs. Here, it is demonstrated that CARs can be delivered selectively into resting CD4$^+$ cells. The particles were generated as described in example 1 except that pCG-1 was substituted by the CAR encoding transfer plasmid. When resting T cells were transduced with $4^H$/IL7$^H$-LV delivering ErbB2-specific chimeric antigen receptors (ErbB2-CAR), ErbB2-CAR expression was only observed in the CD4$^+$ T cell population. Compared to the IL7-deficienct CD4-targeted LV ($4^H$-LV), the $4^H$/IL7$^H$-LV was more efficient in delivering the CAR gene while retaining the selectivity for the CD4$^+$ T cells (FIG. 1).

Example 3

Figure 2:
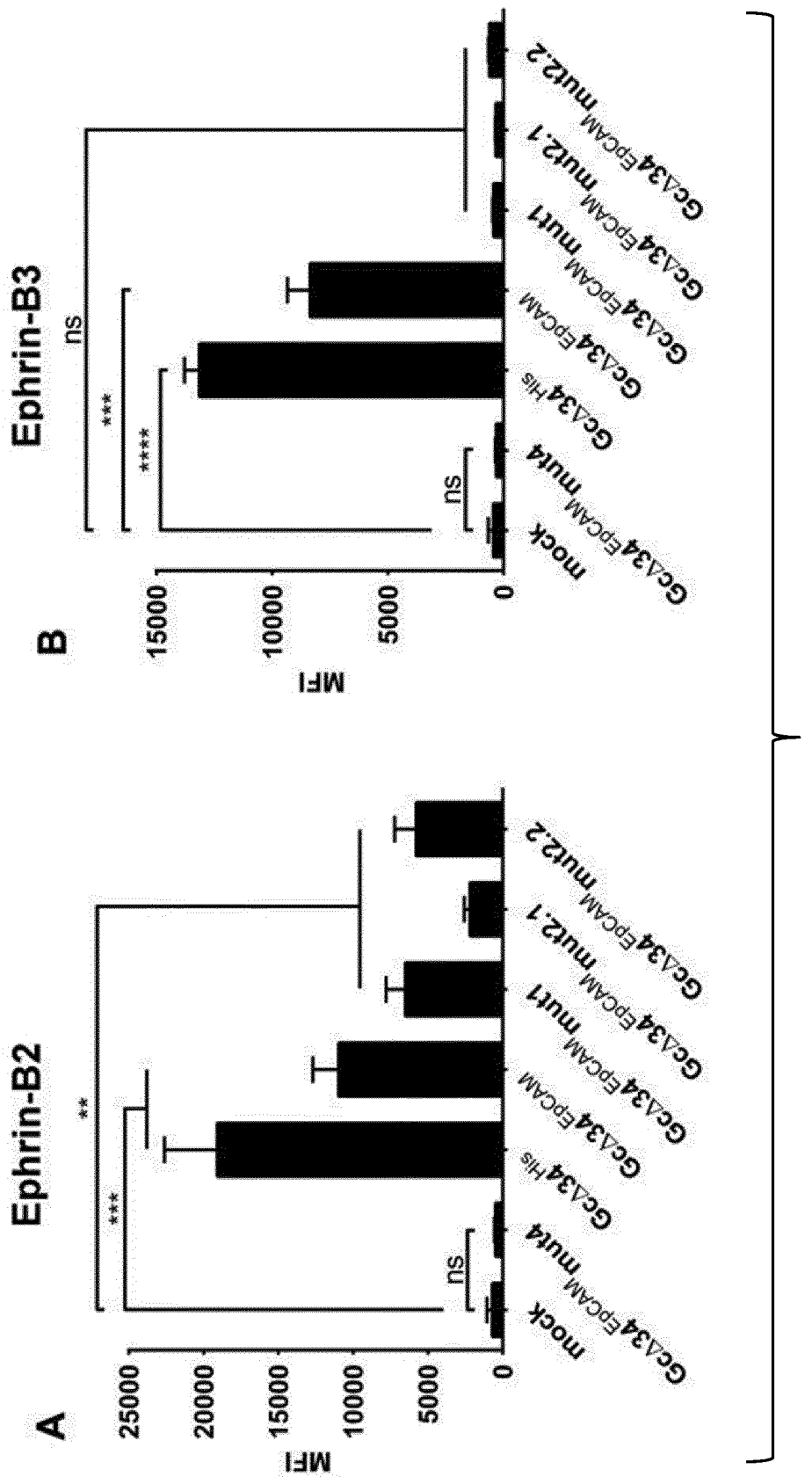
FIG. 2: Mutation of the NiV envelope glycoprotein G to ablate natural receptor recognition. Binding of Ephrin-B2 (A) and B3 (B) to NiV-G mutants is shown. 293T cells were transfected either mock, plasmids encoding for GcΔ34$^{His}$, or with different GcΔ34$^{EpCAM}$ mutants: unmutated (GcΔ34$^{EpCAM}$), E533A (GcΔ34$^{EpCAM}$mut1), Q530A+E533A (GcΔ34$^{EpCAM}$mut2.1), E501A+W504A (GcΔ34$^{EpCAM}$mut2.2) or E501A+W504A+Q530A+E533A (GcΔ34$^{EpCAM}$mut4) and incubated with 1 µg/ml recombinant Fc-EphrinB2 or B3. The amounts of binding of the receptor by the different mutants are shown as MFI values. Statistics are relating to unmutated GΔ34-DARPin-Ac1 (n=3; mean±standard deviations (SD) are shown; *, P<0, 1, P<0,01;*, P<0,001 by unpaired t test).

The MV Glycoproteins can be Replaced by those of NiV to Selectively Activate and Transduce Resting Human CD8+T Cells In order to efficiently pseudotype VLPs or LVs with NiV glycoproteins, the NiV-G was truncated at its cytoplasmic tail by 34 amino acids (GcΔ34) and the NiV-F was truncated at its cytoplasmic tail by 22 amino acids (FΔ22). Next, the natural receptor recognition of GcΔ34 for Ephrin-B2/B3 was destroyed by introducing four point mutations (E501A, W504A, Q530A, E533A) into GcΔ34. LVs pseudotyped with this engineered G protein completely lost binding to the natural Ephrin-B2 and -B3 NiV receptors (FIG. 2) and did not enter into cells expressing these receptors.

Figure 10:
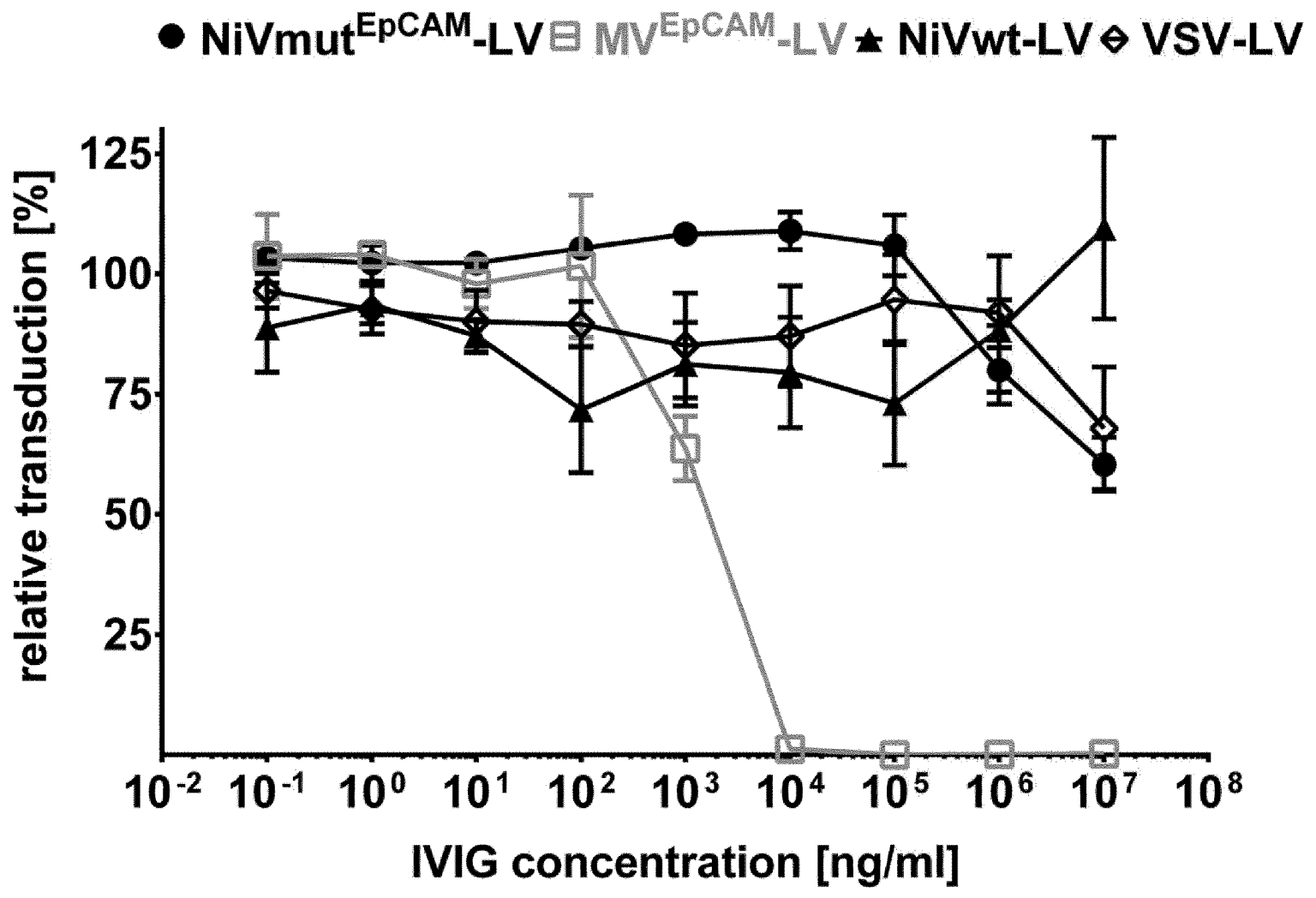

Moreover, NiV-pseudotyped LVs have some attractive features, like high production yield and resistance to intravenous immunoglobulins. Since there is no vaccination against NiV and the few outbreaks are limited to a few cases in Malaysia, Bangladesh and India (SEARO|WHO South-East Asia Region), there should be no neutralizing antibodies present in humans. To demonstrate this, intravenous immunoglobulin (IVIG; Intratect®) covered the widest range of human serum donors, was incubated with NiVwt-LV, NiVmut$^{EpCAM}$-LV, MV$^{EpCAM}$-LV and VSV-LV at increasing concentrations prior to the transduction of target cells. GFP expression was then determined by flow cytometry three days post transduction. As expected, transduction mediated by VSVG-LV and NiVwt-LV was unaffected by the treatment with IVIG. MV$^{EpCAM}$-LV, on the other hand, showed a dose-dependent decrease in transduction rates with a complete neutralization at 100 µg/ml of IVIG. In contrast, NiVmut$^{EpCAM}$-LV was resistant against IVIG at all concentrations used and must thus be at least 10000-fold less sensitive against human immunoglobulin than the corresponding MV-based vector (FIG. 10). These results show that receptor-targeted vectors based on NiV glycoproteins will not be neutralized when injected into humans.

Therefore, due to the above features of the NiV-G, the NiV-pseudotypes were further used to generate cytokine-displaying CD8-targeted particles. Here, a CD8 specific scFv derived from OKT8 was displayed on the NiV-GΔ34mut4 to generate envelope plasmid pCG-Gmut-CD8scFv and human IL7 was displayed on the NiV-GΔ34mut4 to generate envelope plasmid pCG-Gmut-IL7. In order to produce $8^G$/IL7$^G$-LV, 0.45 µg of pCG-Gmut-CD8scFv, 0.45 µg of pCG-Gmut-IL7, 4.7 µg of pCG-FcΔ22, 14.4 µg of HIV-1 packaging plasmid pCMVΔR8.9, and 15.1 µg of transfer-LV plasmids were used for transfection of HEK293T cells in one T175 flask. Titers of ~10$^7$ to/ml were obtained for LVs and titers of ~1.5 ug p24/ml were obtained for VLPs.

Figure 11:
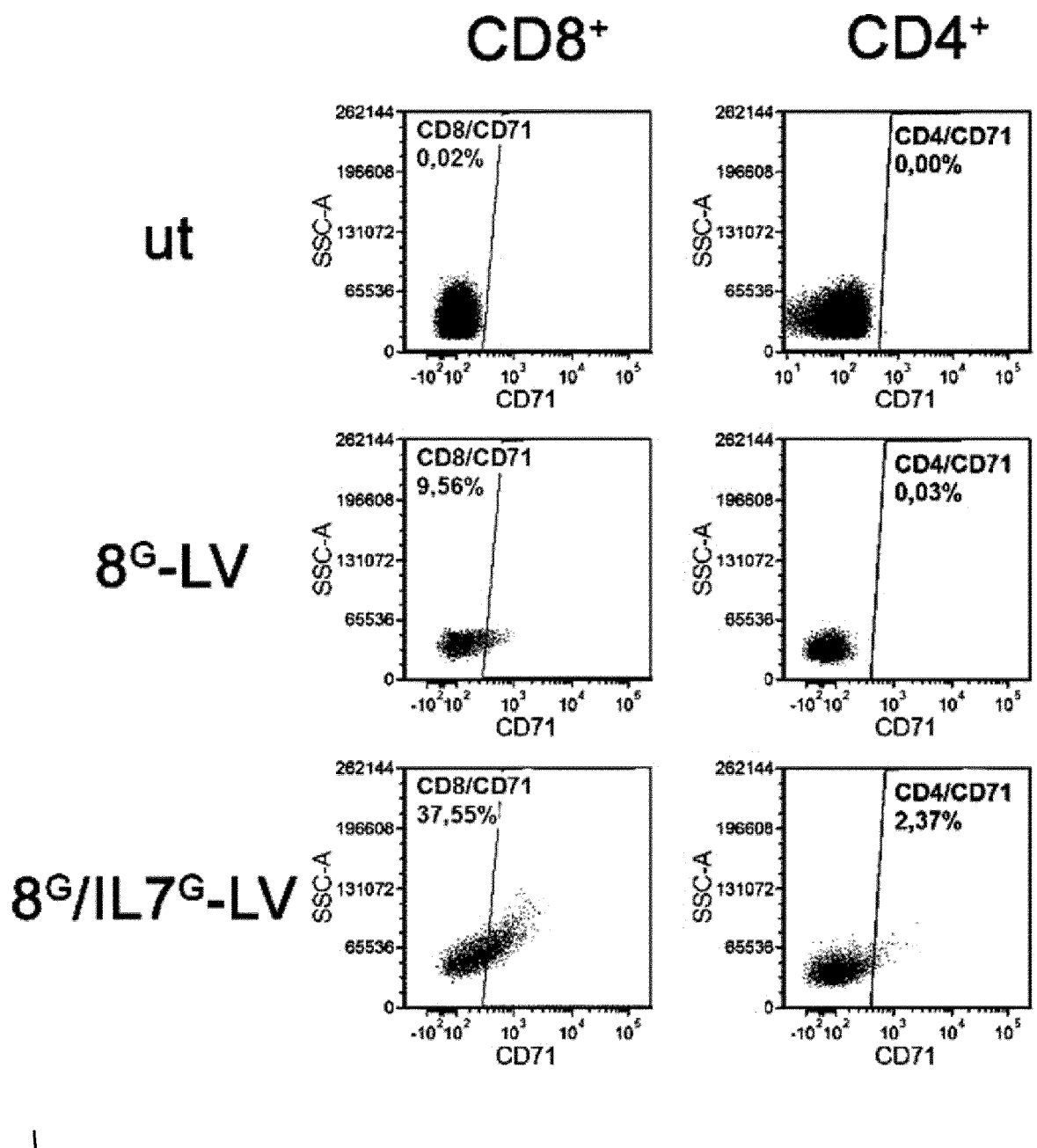
FIG. 11: Selective activation of CD8$^+$ T cells by $8^G$/IL$7^G$-LV. Freshly isolated CD3$^+$ T cells were left untransduced (ut) or transduced with different types of LVs pseudotyped with CD8-scFv-Gmut ($8^G$-LV) or CD8-scFv-Gmut/IL7-Gmut ($8^G$/IL$7^G$-LV). Three days later the cells were stained by CD8, CD4, and CD71 antibodies. The CD71 expression in the CD4- or CD8-gated T cells is shown.
Figure 12:
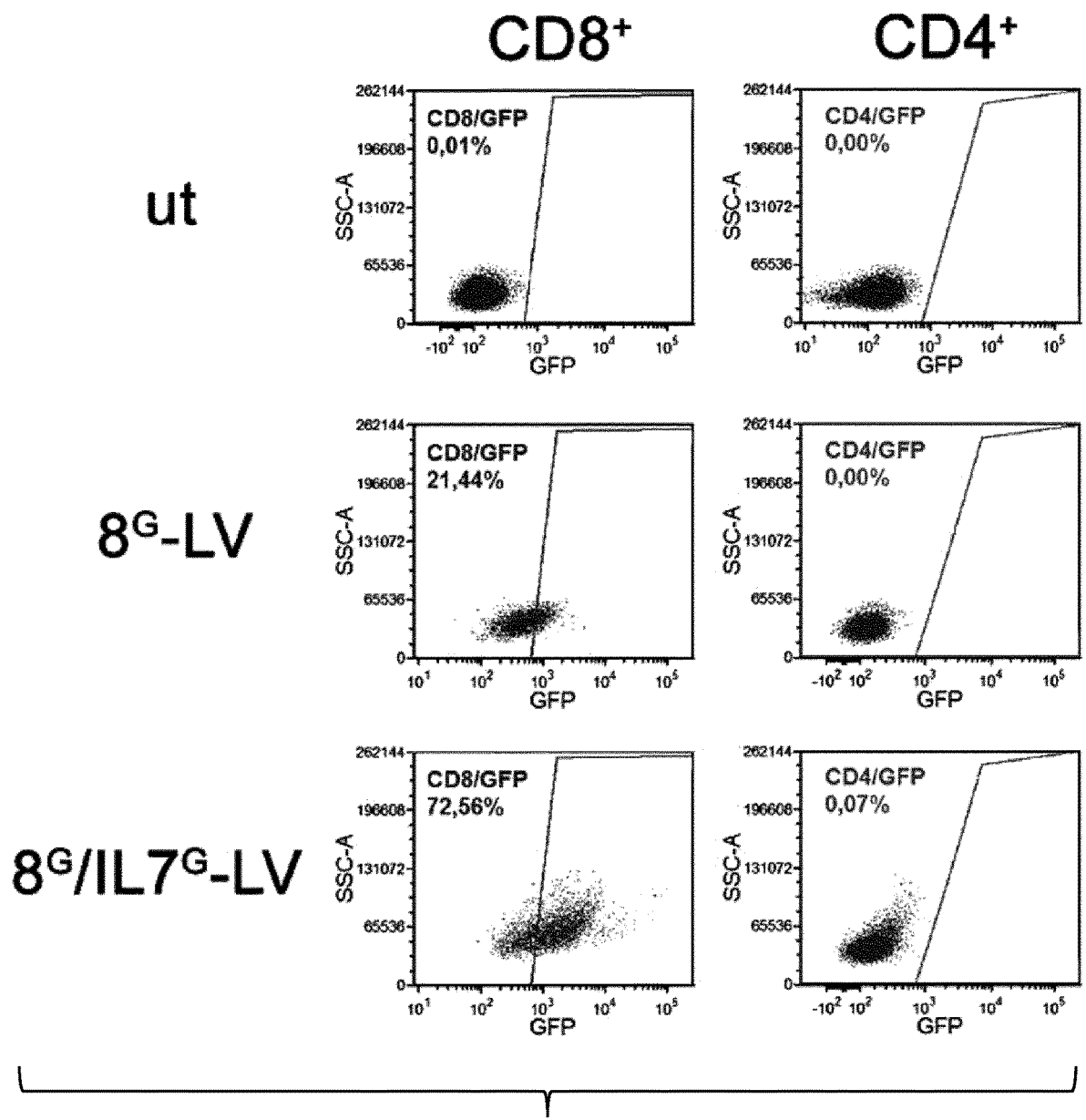
FIG. 12: Efficient and selective transduction of resting CD8$^+$ T cells by $8^G$/IL$7^G$-LV. Freshly isolated CD3$^+$ T cells were left untransduced (ut) or transduced with different types of LVs pseudotyped with CD8-scFv-Gmut ($8^G$-LV) or CD8-scFv-Gmut /IL7-Gmut ($8^G$/IL$7^G$-LV). Three days later the cells were stained by CD3, CD8, and CD4 antibodies. The GFP expression in CD4- or CD8-gated T cells is shown.
Figure 13:
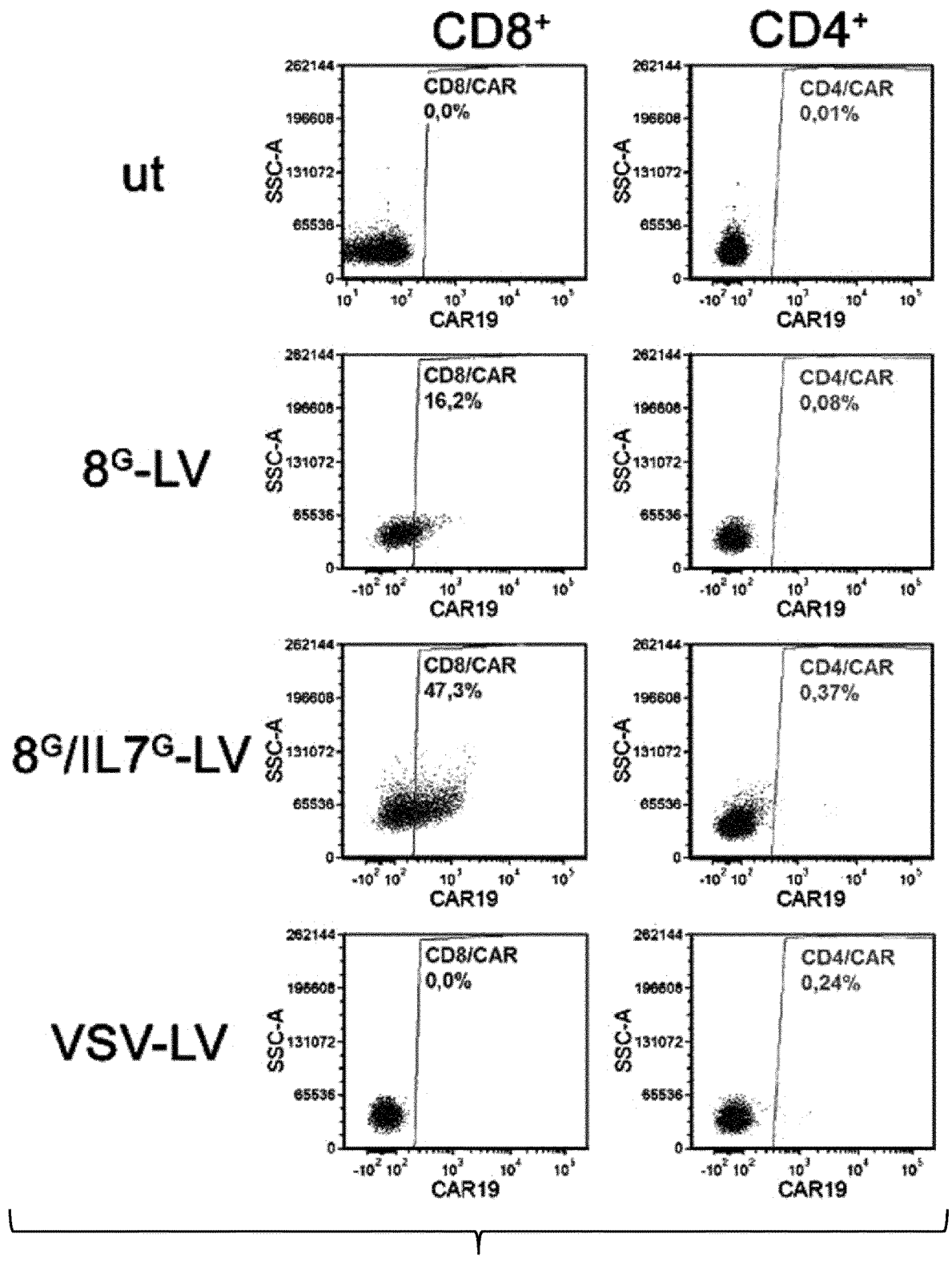
FIG. 13: Efficient CAR19 gene transfer into resting CD8$^+$ T cells by $8^G$/IL$7^G$-LV. Freshly isolated CD3$^+$ T cells were left untransduced (ut) or transduced with different types of LVs pseudotyped with CD8-scFv-Gmut ($8^G$-LV), CD8-scFv-Gmut /IL7-Gmut ($8^G$/IL$7^G$-LV) or VSVG (VSV-LV). The therapeutic gene encoding a CD19-specfic CAR (CAR19) was delivered by the LVs. Three days after transduction, the CAR19 expression was detected by anti-cmyc antibody. The percentage of CAR19 expressing cells in CD4$^+$ or CD8$^+$ T cells is shown.
Figure 14:
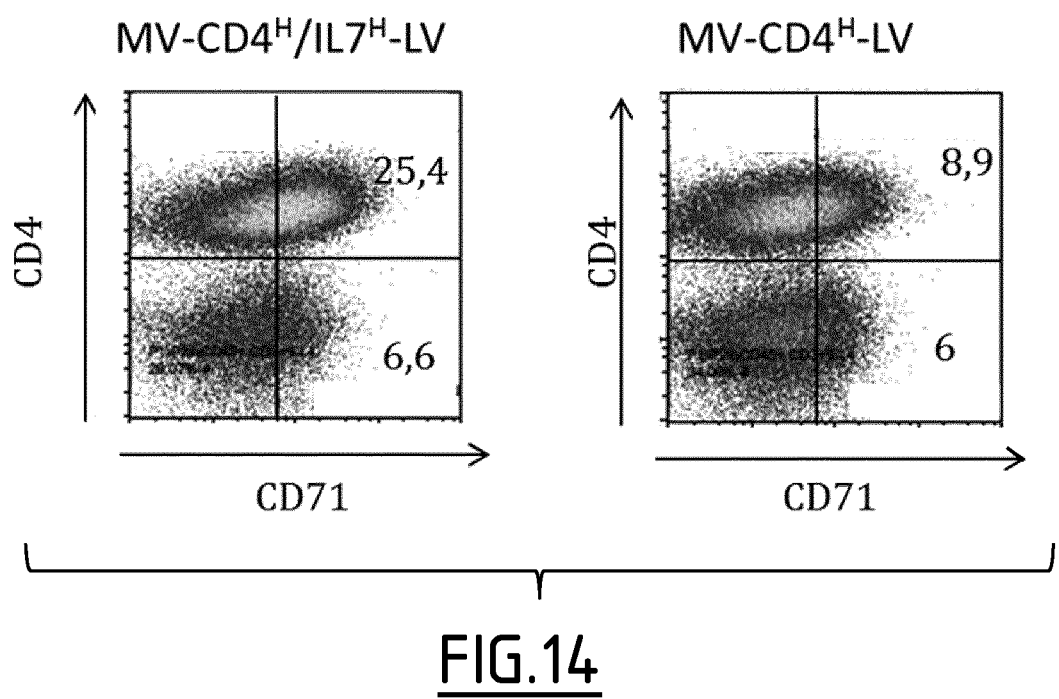
FIG. 14: $4^H$/IL$7^H$-LVs allow targeted in vivo activation of CD4+ T cells in humanized mice.

Similar to what was achieved by $4^H$/IL7$^H$-LV, $8^G$/IL7$^G$-LV (comprising proteins of sequence SEQ ID NO: 4, 6 and 16) was able to selectively stimulate and transduce CD8$^+$ T cells in the peripheral blood mixture. As shown in FIG. 11, when freshly isolated human CD3$^+$ T cells were incubated with $8^G$/IL7$^G$-LV for 3 days, not only the CD8$^+$ T cell subsets in the culture upregulated the CD71 expression but also only this cell population efficiently expressed the reporter transgene GFP (FIG. 12) or therapeutic transgene CAR19 (FIG. 13). In addition, compared to the parental IL7-deficient CD8-targeted LV ($8^G$-LV), the $8^G$/IL7$^G$-LV was more efficient in activating the target cells and delivering transgenes without compromise on specificity for transduction of the CD8$^+$ T cells.

Example 4

Identification of an Optimal Ratio of CD8-Targeting NiV-G to IL7-Displaying NiV-G In order to hit more target cells, improve the titer and enhance the specificity of the particles for selective activation and transduction of a distinct cell population, while maximally reduce the off-target effect, the transfection protocol is further optimized for vector production and carefully determine the amounts of NiV-G$^{targeting\ domain}$ (or MV-H$^{targeting\ domain}$) and NiV-G$^{functional\ domain}$ (MV-H$^{functional\ domain}$) encoding plasmids maintained in the packaging cells.

For the production of $G^8$/G$^{IL7}$-LV, as described in Example 3, total amounts of 0.9 µg of pCG-Gmut plasmids together with 4.7 µg of pCG-FcΔ22, 14.4 µg of HIV-1 packaging plasmid pCMVΔR8.9, and 15.1 µg of pSEW were used for transfection of HEK293T cells in one T175 flask. Meanwhile, pCG-Gmut-CD8scFv and pCG-Gmut-IL7 plasmids are mixed at different ratios at 20:1, 10:1, 5:1, 1:1, or 1:5. The respective cell supernatants containing $8^G$/IL7$^G$-LVs are used for transduction of CD8$^+$ Molt or A301 cells and, 48 h after transduction, the percentage of GFP cells are measured by FACS to calculate the titers. In addition, $8^G$/IL7$^G$ -LVs are used for transduction of freshly isolated CD3$^+$ T cells and then the CD71 and GFP expression in CD8$^+$ and CD8$^-$ cells are determined. The best ratio is identified as giving the highest titer, highest expression of CD71 and GFP in target population and lowest expression in non-target population.

Example 5

Characterization of the Transduced Resting T Cells by IL7-Displaying Targeted VLPs and LVs T cell compartments are highly heterogeneous and T cell subsets are phenotypically and functionally distinct. As far as T cell therapy for cancer is concerned, less differentiated cells are usually correlated with better antitumor effect in vivo. Therefore, it's of importance to identify the T cell subsets that activated or modified by the vector particles according to the invention. Take $8^G/IL7^G$-LV-CAR for example, the phenotypes of the transduced resting T cells should be characterized in comparison to transduced pre-stimulated T cells (with most widely used protocol of CD3/CD28 stimulation). Briefly, 3 days after transduction of resting or pre-stimulated CD3$^+$ T cells, the expression of multiple T cell markers is monitored, including CD11a, CD11b, CD25, CD27, CD28, CD45RA, CD45RO, CD62L, CD69, CD71, CD95, CD127, and CCR7. These molecules are chosen as they have been used in the past to differentiate CD45RA+CD45RO$^-$CD62L$^{high}$CD95$^-$CD27$^{high}$CCR7$^{high}$ naïve (T$_N$), CD45RA$^+$CD45RO$^-$CD62L$^{high}$CD95$^+$ CD27$^{high}$CCR7$^{high}$ stem cell memory (T$_{SCM}$), CD45RA$^-$ CD45RO$^{high}$CD62L+CD95$^+$CD27$^+$central memory (T$_{CM}$), CD45RA$^{-/+}$CD45RO$^{high}$CD62L$^-$CD95+CD27$^{-/+}$CCR7$^-$ effector memory (T$_{EM}$), and CD45RA$^{-/+}$CD45RO$^+$CD62L$^-$ CD95$^{high}$CD27$^-$CD28$^-$CCR7$^-$ effector (T$_E$) T cells. The phenotypes of CAR$^+$ T cells are analyzed by flow cytometry.

In addition, pre-sorted CD4+ T cell subsets (T$_{SCM}$, T$_{CM}$, T$_{EM}$, and T$_E$) are incubated with $4^H/IL7^H$-VLP for example, to demonstrate the advantages of current invention for T cell activation over the conversional TCR stimulation. Briefly, 3 days after incubation with $4^H/IL7^H$-VLP or stimulation by CD3/28 antibodies, above indicated T cell subsets are analyzed for phenotype skewness and activation levels. It is expected that IL7-displaying T cell targeted vector particles activate and transduce less differentiated T cells.

Example 6

Enhance the Function of Ex Vivo Produced CART Cells and Simplify the CART Cell Production Procedure Adoptive T cell immunotherapy has been demonstrated to be an effective regime in clinic for treatment of various types of diseases. However, its broader application has been limited by several issues. On one hand, the production of CAR-engineered or TCR-engineered T cells is very expansive and labor-intensive due to the in vitro stimulation, long-term expansion, and cell isolation and purification. On the other hand, the effector T cells that have been expanded in vitro often persist poorly in vivo, and fail to exhibit a sustained antitumor effect. The current invention provides the potential solutions for these challenges by combining the cell stimulation and gene transfer in a single step and enabling resting T cell transduction. Using this invention, the T cell production process can be significantly simplified therefore reducing the cost of T cell manufacture. Moreover, compared to the conventionally produced cells, CAR/TCR-engineered T cells produced by current invention can be more potent in vivo, due to the potential of efficiently engineering less differentiated cells as demonstrated in Example 5.

To demonstrate these features, freshly isolated human PBMC or CD8$^+$ T cells are transduced with for example $8^G/IL7^G$-LV-CAR or VSV-LV-CAR as control. Meanwhile, conventional CAR T cells are prepared in parallel according to the most widely uses protocol. Briefly, isolated human PBMC or CD8$^+$ T cells from the same donor are simulated with CD3/CD28 antibodies and IL2. Then cells are transduced with $8^G/IL7^G$-LV-CAR or VSV-LV-CAR followed by 10 days expansion in the presence of IL2. 2-3 days after vector transduction of resting T cells or 12 days after transduction of stimulated T cells, these cells are co-cultivated with target tumor cells in vitro or infused in the tumor bearing humanized mouse. Afterwards, in vitro tumor cells lysis and in vivo tumor remission, animal survival, tumor-reactive T cell persistence and proliferation are assessed.

Example 7

Selective Activation and Transduction by IL7-Displaying Targeted Particles in In Vivo like Conditions In a next step, the feasibility of using the viral particles to target and functionally modify the distinct cells in in vivo settings is investigated. Thus, transduction of fresh human peripheral blood with the viral particles is performed, for example with $G^8/G^{IL7}$-LV. This allows evaluation of targeted activation and gene transfer in CD8$^+$ T cell population in the presence of an active human complement system, an obstacle encountered by viral particles in vivo.

Briefly, fresh peripheral blood is incubated with $8^G/IL7^G$-LV-GFP or other control vectors (VSV-LV, $8^H/IL7^H$ -LV, $8^G$-LV, or VSV/IL7$^G$-LV) for 6-8 h. Afterwards, total PBMC are isolated from the blood and further cultured in the T cell culture medium without adding any stimulatory reagents. After 3-4 days, CD8$^+$ and CD8$^-$ cells in the culture are evaluated for CD71 and GFP expression. To confirm the stable gene transfer, a small fraction of cells are transferred into the culture medium supplemented with CD3/CD28 antibodies and IL2 for additional 3 days before the percentages of GFP cells are analyzed.

Example 8

IL7-Displaying Targeted Particles Selectively Activate and Transduce Circulating Resting T Cells in Humanized Mouse Models In order to demonstrate the particles according to the invention are able to be locally or systemically applied in vivo to allow the cell type specific activation or modification, they are applied in mice engrafted with human CD34$^+$ hematopoietic stem cells (HSC) from healthy donors. In this mouse model, multilineage human hematopoietic cells can be generated and these cells are tolerated by the mouse host.

Here, the application of $G^8/G^{IL7}$-pseudotpyed particles for human CD8$^+$ T cell activation and modification is taken for example. Briefly, after having confirmed that the human immune system was successfully established by detecting around 10% of human CD3$^+$ T cells, $G^8/G^{IL7}$-pseudotpyed particles are applied systemically via intravenous injection (iv) or locally via intrasplenic or intrathymic injection. $G^8/G^{IL7}$-VLP is injected to assess the feasibility of selective activation of human CD8$^+$ T cells in vivo. In this experiment setting, the activation level/duration and CD8$^+$ T cells proliferation are analyzed at the different time points after VLP injection. $G^8/G^{IL7}$-LV-GFP is injected to assess the function of in vivo gene delivery. In this experiment setting, the GFP expression, the phenotypes of transduced cells, and their proliferation and persistence are analyzed at the different time points after LV injection. $G^8/G^{IL7}$-LV-CAR is injected to assess the feasibility of therapeutic gene delivery and the in vivo generation of CAR T cells. In this experiment setting, the CAR expression, the phenotypes of transduced cells, the proliferation and persistence of transduced cells in the presence/absence of target tumor cells/antigens, the elimination of local/systemic tumor are analyzed at the different time points after LV injection.

Example 9

Selective Activation of Rhesus Macaque CD4+ T Cells

T cells of non-human primate (NHP) are phenotypically similar to human T cells, making it the best animal model for human immunity and immunotherapies. As far as T cell therapy is concerned, the NHP model could be more reliable in predicting the effect, dosage, application routes, and safety of potential medicaments. Therefore, a tool to specifically modify or inducing a functional change in a distinct cell type in NHP is highly desirable.

Here, the $4^H/IL7^H$-SIV vector and its application for rhesus macaque are described in detail as an example. First, a rhesus macaque CD4-specific DARPin57.2 ($CD4^{D572}$) is used as targeting domain displayed on the Hmut protein (H-$CD4^{D572}$) and the rhesus macaque reactive IL7 is used as functional domain displayed on the Hmut (H-rmIL7). Then the above two H proteins, for example with the ratios determined in Example 4, are used to pseudotype simian immunodeficiency virus mac 251 (SIVmac251)-derived LV. After determining the vector yield and titers by P27 ELISA/Nano-sight and transduction of CD4+ simian cells, freshly isolated simian CD3+ T cells are transduced with $4^H/IL7^H$-SIV delivering GFP or CARs. Then, the activation makers and transgene expression in $CD4^+$ vs $CD4^-$ T cells was determined as described above. Next, the possibility of in vivo application is assessed in NHP models. For this purpose, a single dose of vectors is injected slowly into two axillary lymph nodes of each of the enrolled animals (eg. rhesus macaque). One week post-injection, blood samples are collected and one of the two injected lymph nodes is removed by surgery and dissociated into single cell suspensions. The detailed analysis is performed to analyse the phenotypes, specific activation, transgene expression levels and/or function (when therapeutic transgene is delivered) of in vivo transduced T cells. Moreover, the second lymph node receives a second dose of the same vector and the enrolled animals are monitored for at six months to assess the proliferation, persistence, and/or function (when therapeutic transgene is delivered) of in vivo transduced T cells.

Example 10

Selectively Active and Expand Antigen-Specific T Cells in Immunocompetent Mouse Model The potential of targeting cytokine to function at the disease site while avoiding the systemic toxicity can be well evaluated in an immunocompetent mouse melanoma tumor model. IL12 displaying murine CD8-targeted VLP ($m8^G$/mIL$12^G$-VLP) is taken as an example. Previous studies have shown that IL12 application can enhance the transferred tumor-reactive T cells tolerance and antitumor efficacy, but it is very toxic systemically. To overcome this drawback, in our study, $m8^G$/mIL$12^G$-VLP is used to control the function of IL12 to take place at the tumor sites. Wide type 057/Bl6 mouse is transplanted with B16/OVA melanoma cells, after the establishment of tumor, the mouse is treated by irradiation and transferred with T cells isolated from C57/Bl6 OT-I transgenic mouse. After OT-I T cell transplantation, the mice are treated with $m8^G$/mIL$12^G$-VLP, or with murine IL12, or with PBS as controls via i.v. injection. The tumor volume, in vivo persistence and function of OT-I T cells, and mouse survival are analyzed.

Example 11

In Vivo Targeted Targeted Activation of Human CD4+ T Cells.

In order to evaluate the in vivo performance of the MV-$4^H$/IL$7^H$-LVs for activating human $CD4^+$ T cells, NOD/SCID gc−/− (NSG) mice were engrafted with $CD3^+$ cord blood T cells. Human T cell reconstitution was weekly determined in the blood. When 20% of hT cells was detected (% $hCD3^+$ cells/total $hCD45^+$+$mCD45^+$ cells), the mice were injected IV with 1E6 IU MV-$4^H$/IL$7^H$-LVs or MV-$4^H$-LVs. Two weeks post-injection of the vectors, the mice were sacrificed and the splenocytes and peripheral blood mononuclear cells were isolated. Remarkably, it was found a stronger specific IL-7 activation revealed by a CD71 late activation marker of the human CD4+ T cells in case of the MV-$4^H$/IL$7^H$-LVs (25% CD4+ CD71+ cells) as compared to MV-$4^H$-LVs (8% CD4+ CD71+ cells) (FIG. 14). Moreover, the CD4-T cells, which represent the CD8+ T cells, show identical expression of CD71 for both targeting vectors. The latter emphasizes that the IL-7 survival signaling was only activating the targeted CD4+ T cells and not the CD8+ cells. In conclusion, next to the in vitro specific activation of the target cells achieved with MV-$4^H$/IL$7^H$-LVs, the specific activation of CD4+ T cells by MV-$4^H$/IL$7^H$-LVs was confirmed in vivo in human blood system mouse model.

The invention claimed is:

1. A pseudotyped lentiviral vector comprising:
   a) at least one cell targeting fusion protein comprising (i) an envelope glycoprotein G of a Nipah virus that lacks amino acids 2-34 of SEQ ID NO: 9 (GcΔ34) and comprises the point mutations E501A, W504A, Q530A, and E533A by comparison to the sequence of SEQ ID NO:9 and (ii) at least one cell targeting domain,
   b) at least one envelope glycoprotein F of a Nipah virus that lacks amino acids 525-546 of SEQ ID NO:11 (FΔ22), and
   c) a nucleic acid encoding a chimeric antigen receptor.

2. A pseudotyped lentiviral vector comprising:
   a) at least one cell targeting fusion protein comprising an envelope glycoprotein G of a Nipah virus that lacks amino acids 2-34 of SEQ ID NO: 9 (GcΔ34) and comprises the point mutations E501A, W504A, Q530A, and E533A by comparison to the sequence of SEQ ID NO:9, and
   b) at least one glycoprotein that is an envelope glycoprotein F of a Nipah virus that lacks amino acids 525-546 of SEQ ID NO:11 (FcΔ22).

3. The pseudotyped lentiviral vector of claim 2, wherein the at least one cell targeting fusion protein further comprises at least one cell targeting domain.

4. The pseudotyped lentiviral vector of claim 1, wherein the at least one cell targeting domain is specific for CD3, CD8, or CD4.

5. The pseudotyped lentiviral vector of claim 1, wherein the at least one cell targeting domain is specific for CD8 or CD4.

6. The pseudotyped lentiviral vector of claim 1, wherein the at least one cell targeting domain is a Darpin or an scFv.

7. The pseudotyped lentiviral vector of claim 3, wherein the at least one cell targeting domain is a Darpin or an scFv.

8. The pseudotyped lentiviral vector of claim 1, wherein the at least one cell targeting domain is an scFv specific for CD8.

9. The pseudotyped lentiviral vector of claim 1, wherein the encoded chimeric antigen receptor is specific for CD19.

10. A pseudotyped lentiviral vector comprising:
    a) a cell targeting fusion protein comprising (i) a truncated glycoprotein G of a Nipah virus that lacks amino acids 2-34 of SEQ ID NO:9 (GcΔ34) comprises the point mutations E501A, W504A, Q530A, and E533A by comparison to the sequence of SEQ ID NO:9, and (ii) an scFv that is specific for CD8,
    b) a truncated glycoprotein F of a Nipah virus that lacks amino acids 525-546 of SEQ ID NO: 11 (FcΔ22), and
    c) a nucleic acid encoding a chimeric antigen receptor that is specific for CD19.

* * * * *

SEQUENCE LISTING

```
<160> NUMBER OF SEQ ID NOS: 16

<210> SEQ ID NO 1
<211> LENGTH: 2217
<212> TYPE: DNA
<213> ORGANISM: Artificial Sequence
<220> FEATURE:
<223> OTHER INFORMATION: Truncated and mutated (Y481A, R533A, S548L,
      F549S) MV H protein (HcDelta18) fused to Designed Ankyrin Repeat
      Protein (DARPin)-29.2 specific for human CD4
<220> FEATURE:
<221> NAME/KEY: CDS
<222> LOCATION: (1)..(2217)

<400> SEQUENCE: 1 atg gga agt agg ata gtc att aac aga gaa cat ctt atg att gat aga      48
```

```
                Met Gly Ser Arg Ile Val Ile Asn Arg Glu His Leu Met Ile Asp Arg
                1               5                   10                  15 cct tat gtt ttg ctg gct gtt ctg ttt gtc atg ttt ctg agc ttg atc       96
Pro Tyr Val Leu Leu Ala Val Leu Phe Val Met Phe Leu Ser Leu Ile
                20                  25                  30 ggg ttg cta gcc att gca gga att cga ctt cat cgg gca gcc atc tac      144
Gly Leu Leu Ala Ile Ala Gly Ile Arg Leu His Arg Ala Ala Ile Tyr
            35                  40                  45 acc gca gag atc cat aaa agc ctc agc acc aat cta gat gta act aac      192
Thr Ala Glu Ile His Lys Ser Leu Ser Thr Asn Leu Asp Val Thr Asn
        50                  55                  60 tca atc gag cat cag gtc aag gac gtg ctg aca cca ctc ttc aaa atc      240
Ser Ile Glu His Gln Val Lys Asp Val Leu Thr Pro Leu Phe Lys Ile
65                  70                  75                  80 atc ggt gat gaa gtg ggc ctg agg aca cct cag aga ttc act gac cta      288
Ile Gly Asp Glu Val Gly Leu Arg Thr Pro Gln Arg Phe Thr Asp Leu
                85                  90                  95 gtg aaa ttc atc tct gac aag att aaa ttc ctt aat ccg gat agg gag      336
Val Lys Phe Ile Ser Asp Lys Ile Lys Phe Leu Asn Pro Asp Arg Glu
            100                 105                 110 tac gac ttc aga gat ctc act tgg tgt atc aac ccg cca gag aga atc      384
Tyr Asp Phe Arg Asp Leu Thr Trp Cys Ile Asn Pro Pro Glu Arg Ile
        115                 120                 125 aaa ttg gat tat gat caa tac tgt gca gat gtg gct gct gaa gag ctc      432
Lys Leu Asp Tyr Asp Gln Tyr Cys Ala Asp Val Ala Ala Glu Glu Leu
    130                 135                 140 atg aat gca ttg gtg aac tca act cta ctg gag acc aga aca acc aat      480
Met Asn Ala Leu Val Asn Ser Thr Leu Leu Glu Thr Arg Thr Thr Asn
145                 150                 155                 160 cag ttc cta gct gtc tca aag gga aac tgc tca ggg ccc act aca atc      528
Gln Phe Leu Ala Val Ser Lys Gly Asn Cys Ser Gly Pro Thr Thr Ile
                165                 170                 175 aga ggt caa ttc tca aac atg tcg ctg tcc ctg tta gac ttg tat tta      576
Arg Gly Gln Phe Ser Asn Met Ser Leu Ser Leu Leu Asp Leu Tyr Leu
            180                 185                 190 ggt cga ggt tac aat gtg tca tct ata gtc act atg aca tcc cag gga      624
Gly Arg Gly Tyr Asn Val Ser Ser Ile Val Thr Met Thr Ser Gln Gly
        195                 200                 205 atg tat ggg gga act tac cta gtg gaa aag cct aat ctg agc agc aaa      672
Met Tyr Gly Gly Thr Tyr Leu Val Glu Lys Pro Asn Leu Ser Ser Lys
    210                 215                 220 agg tca gag ttg tca caa ctg agc atg tac cga gtg ttt gaa gta ggt      720
Arg Ser Glu Leu Ser Gln Leu Ser Met Tyr Arg Val Phe Glu Val Gly
225                 230                 235                 240 gtt atc aga aat ccg ggt ttg ggg gct ccg gtg ttc cat atg aca aac      768
Val Ile Arg Asn Pro Gly Leu Gly Ala Pro Val Phe His Met Thr Asn
                245                 250                 255 tat ctt gag caa cca gtc agt aat gat ctc agc aac tgt atg gtg gct      816
Tyr Leu Glu Gln Pro Val Ser Asn Asp Leu Ser Asn Cys Met Val Ala
            260                 265                 270 ttg ggg gag ctc aaa ctc gca gcc ctt tgt cac ggg gaa gat tct atc      864
Leu Gly Glu Leu Lys Leu Ala Ala Leu Cys His Gly Glu Asp Ser Ile
        275                 280                 285 aca att ccc tat cag gga tca ggg aaa ggt gtc agc ttc cag ctc gtc      912
Thr Ile Pro Tyr Gln Gly Ser Gly Lys Gly Val Ser Phe Gln Leu Val
    290                 295                 300 aag cta ggt gtc tgg aaa tcc cca acc gac atg caa tcc tgg gtc ccc      960
Lys Leu Gly Val Trp Lys Ser Pro Thr Asp Met Gln Ser Trp Val Pro
305                 310                 315                 320
```

-continued

| | | |
|---|---|---|
| tta tca acg gat gat cca gtg ata gac agg ctt tac ctc tca tct cac<br>Leu Ser Thr Asp Asp Pro Val Ile Asp Arg Leu Tyr Leu Ser Ser His<br>325                          330                            335 | 1008 |
| aga ggt gtt atc gct gac aac caa gca aaa tgg gct gtc ccg aca aca<br>Arg Gly Val Ile Ala Asp Asn Gln Ala Lys Trp Ala Val Pro Thr Thr<br>340                          345                            350 | 1056 |
| cga aca gat gac aag ttg cga atg gag aca tgc ttc caa cag gcg tgt<br>Arg Thr Asp Asp Lys Leu Arg Met Glu Thr Cys Phe Gln Gln Ala Cys<br>355                          360                          365 | 1104 |
| aag ggt aaa atc caa gca ctc tgc gag aat ccc gag tgg gca cca ttg<br>Lys Gly Lys Ile Gln Ala Leu Cys Glu Asn Pro Glu Trp Ala Pro Leu<br>370                          375                          380 | 1152 |
| aag gat aac agg att cct tca tac ggg gtc ttg tct gtt gat ctg agt<br>Lys Asp Asn Arg Ile Pro Ser Tyr Gly Val Leu Ser Val Asp Leu Ser<br>385                          390                          395                          400 | 1200 |
| ctg aca gtt gag ctt aaa atc aaa att gct tcg gga ttc ggg cca ttg<br>Leu Thr Val Glu Leu Lys Ile Lys Ile Ala Ser Gly Phe Gly Pro Leu<br>                          405                          410                          415 | 1248 |
| atc aca cac ggt tca ggg atg gac cta tac aaa tcc aac cac aac aat<br>Ile Thr His Gly Ser Gly Met Asp Leu Tyr Lys Ser Asn His Asn Asn<br>                          420                          425                          430 | 1296 |
| gtg tat tgg ctg act atc ccg cca atg aag aac cta gcc tta ggt gta<br>Val Tyr Trp Leu Thr Ile Pro Pro Met Lys Asn Leu Ala Leu Gly Val<br>                          435                          440                          445 | 1344 |
| atc aac aca ttg gag tgg ata ccg aga ttc aag gtt agt ccc gca ctc<br>Ile Asn Thr Leu Glu Trp Ile Pro Arg Phe Lys Val Ser Pro Ala Leu<br>450                          455                          460 | 1392 |
| ttc act gtc cca att aag gaa gca ggc gga gac tgc cat gcc cca aca<br>Phe Thr Val Pro Ile Lys Glu Ala Gly Gly Asp Cys His Ala Pro Thr<br>465                          470                          475                          480 | 1440 |
| tac cta cct gcg gag gtg gat ggt gat gtc aaa ctc agt tcc aat ctg<br>Tyr Leu Pro Ala Glu Val Asp Gly Asp Val Lys Leu Ser Ser Asn Leu<br>                          485                          490                          495 | 1488 |
| gtg att cta cct ggt caa gat ctc caa tat gtt ttg gca acc tac gat<br>Val Ile Leu Pro Gly Gln Asp Leu Gln Tyr Val Leu Ala Thr Tyr Asp<br>500                          505                          510 | 1536 |
| act tcc gcg gtt gaa cat gct gtg gtt tat tac gtt tac agc cca agc<br>Thr Ser Ala Val Glu His Ala Val Val Tyr Tyr Val Tyr Ser Pro Ser<br>515                          520                          525 | 1584 |
| cgc cta tcg tct tac ttt tat cct ttt agg ttg cct ata aag ggg gtc<br>Arg Leu Ser Ser Tyr Phe Tyr Pro Phe Arg Leu Pro Ile Lys Gly Val<br>                          530                          535                          540 | 1632 |
| ccc atc gaa tta caa gtg gaa tgc ttc aca tgg gac caa aaa ctc tgg<br>Pro Ile Glu Leu Gln Val Glu Cys Phe Thr Trp Asp Gln Lys Leu Trp<br>545                          550                          555                          560 | 1680 |
| tgc cgt cac ttc tgt gtg ctt gcg gac tca gaa tct ggt gga cat atc<br>Cys Arg His Phe Cys Val Leu Ala Asp Ser Glu Ser Gly Gly His Ile<br>                          565                          570                          575 | 1728 |
| act cac tct ggg atg gtg ggc atg gga gtc agc tgc aca gtc acc cgg<br>Thr His Ser Gly Met Val Gly Met Gly Val Ser Cys Thr Val Thr Arg<br>                          580                          585                          590 | 1776 |
| gaa gat gga acc aat gcg gcc cag ccg gcc gac ctg ggt aag aaa ctg<br>Glu Asp Gly Thr Asn Ala Ala Gln Pro Ala Asp Leu Gly Lys Lys Leu<br>                          595                          600                          605 | 1824 |
| ctg gaa gct gct cgt gct ggt cag gac gac gaa gtt cgt atc ctg atg<br>Leu Glu Ala Ala Arg Ala Gly Gln Asp Asp Glu Val Arg Ile Leu Met<br>610                          615                          620 | 1872 |
| gct aac ggt gct gac gtt aac gct act gac act ctt ggt cgt act ccg<br>Ala Asn Gly Ala Asp Val Asn Ala Thr Asp Thr Leu Gly Arg Thr Pro<br>625                          630                          635                          640 | 1920 |

```
cta cac ctg gct gct cag aat ggt cac ctg gaa atc gtt gaa gtt ctg      1968
Leu His Leu Ala Ala Gln Asn Gly His Leu Glu Ile Val Glu Val Leu
              645                 650                 655 ctg aag cac agt gct gac gtt aac gct att gaa gag gtt ggt atg act      2016
Leu Lys His Ser Ala Asp Val Asn Ala Ile Glu Glu Val Gly Met Thr
              660                 665                 670 ccg ctg cac ctg gct gtt gtt gct ggt cac ctg gaa atc gtt gaa gtt      2064
Pro Leu His Leu Ala Val Val Ala Gly His Leu Glu Ile Val Glu Val
              675                 680                 685 ctg ctg aag aac ggt gct gac gtt aac gct cag gac aaa ttc ggt aag      2112
Leu Leu Lys Asn Gly Ala Asp Val Asn Ala Gln Asp Lys Phe Gly Lys
              690                 695                 700 acc gct ttc gac atc tcc atc gac tac ggt aac gag gac ctg gct gaa      2160
Thr Ala Phe Asp Ile Ser Ile Asp Tyr Gly Asn Glu Asp Leu Ala Glu
705                 710                 715                 720 atc ctg caa aag ctt aat gcg gcc gca aga ggt tct cat cac cat cac      2208
Ile Leu Gln Lys Leu Asn Ala Ala Ala Arg Gly Ser His His His His
              725                 730                 735 cat cac taa                                                          2217
His His
```

```
<210> SEQ ID NO 2
<211> LENGTH: 738
<212> TYPE: PRT
<213> ORGANISM: Artificial Sequence
<220> FEATURE:
<223> OTHER INFORMATION: Synthetic Construct

<400> SEQUENCE: 2

Met Gly Ser Arg Ile Val Ile Asn Arg Glu His Leu Met Ile Asp Arg
1               5                   10                  15

Pro Tyr Val Leu Leu Ala Val Leu Phe Val Met Phe Leu Ser Leu Ile
            20                  25                  30

Gly Leu Leu Ala Ile Ala Gly Ile Arg Leu His Arg Ala Ala Ile Tyr
        35                  40                  45

Thr Ala Glu Ile His Lys Ser Leu Ser Thr Asn Leu Asp Val Thr Asn
    50                  55                  60

Ser Ile Glu His Gln Val Lys Asp Val Leu Thr Pro Leu Phe Lys Ile
65                  70                  75                  80

Ile Gly Asp Glu Val Gly Leu Arg Thr Pro Gln Arg Phe Thr Asp Leu
                85                  90                  95

Val Lys Phe Ile Ser Asp Lys Ile Lys Phe Leu Asn Pro Asp Arg Glu
            100                 105                 110

Tyr Asp Phe Arg Asp Leu Thr Trp Cys Ile Asn Pro Pro Glu Arg Ile
        115                 120                 125

Lys Leu Asp Tyr Asp Gln Tyr Cys Ala Asp Val Ala Ala Glu Glu Leu
    130                 135                 140

Met Asn Ala Leu Val Asn Ser Thr Leu Leu Glu Thr Arg Thr Thr Asn
145                 150                 155                 160

Gln Phe Leu Ala Val Ser Lys Gly Asn Cys Ser Gly Pro Thr Thr Ile
                165                 170                 175

Arg Gly Gln Phe Ser Asn Met Ser Leu Ser Leu Leu Asp Leu Tyr Leu
            180                 185                 190

Gly Arg Gly Tyr Asn Val Ser Ser Ile Val Thr Met Thr Ser Gln Gly
        195                 200                 205

Met Tyr Gly Gly Thr Tyr Leu Val Glu Lys Pro Asn Leu Ser Ser Lys
    210                 215                 220
```

```
Arg Ser Glu Leu Ser Gln Leu Ser Met Tyr Arg Val Phe Glu Val Gly
225                 230                 235                 240

Val Ile Arg Asn Pro Gly Leu Gly Ala Pro Val Phe His Met Thr Asn
            245                 250                 255

Tyr Leu Glu Gln Pro Val Ser Asn Asp Leu Ser Asn Cys Met Val Ala
        260                 265                 270

Leu Gly Glu Leu Lys Leu Ala Ala Leu Cys His Gly Glu Asp Ser Ile
    275                 280                 285

Thr Ile Pro Tyr Gln Gly Ser Gly Lys Gly Val Ser Phe Gln Leu Val
290                 295                 300

Lys Leu Gly Val Trp Lys Ser Pro Thr Asp Met Gln Ser Trp Val Pro
305                 310                 315                 320

Leu Ser Thr Asp Pro Val Ile Asp Arg Leu Tyr Leu Ser Ser His
            325                 330                 335

Arg Gly Val Ile Ala Asp Asn Gln Ala Lys Trp Ala Val Pro Thr Thr
            340                 345                 350

Arg Thr Asp Asp Lys Leu Arg Met Glu Thr Cys Phe Gln Gln Ala Cys
        355                 360                 365

Lys Gly Lys Ile Gln Ala Leu Cys Glu Asn Pro Glu Trp Ala Pro Leu
370                 375                 380

Lys Asp Asn Arg Ile Pro Ser Tyr Gly Val Leu Ser Val Asp Leu Ser
385                 390                 395                 400

Leu Thr Val Glu Leu Lys Ile Lys Ile Ala Ser Gly Phe Gly Pro Leu
            405                 410                 415

Ile Thr His Gly Ser Gly Met Asp Leu Tyr Lys Ser Asn His Asn Asn
            420                 425                 430

Val Tyr Trp Leu Thr Ile Pro Pro Met Lys Asn Leu Ala Leu Gly Val
        435                 440                 445

Ile Asn Thr Leu Glu Trp Ile Pro Arg Phe Lys Val Ser Pro Ala Leu
450                 455                 460

Phe Thr Val Pro Ile Lys Glu Ala Gly Gly Asp Cys His Ala Pro Thr
465                 470                 475                 480

Tyr Leu Pro Ala Glu Val Asp Gly Asp Val Lys Leu Ser Ser Asn Leu
            485                 490                 495

Val Ile Leu Pro Gly Gln Asp Leu Gln Tyr Val Leu Ala Thr Tyr Asp
            500                 505                 510

Thr Ser Ala Val Glu His Ala Val Tyr Tyr Val Tyr Ser Pro Ser
        515                 520                 525

Arg Leu Ser Ser Tyr Phe Tyr Pro Phe Arg Leu Pro Ile Lys Gly Val
        530                 535                 540

Pro Ile Glu Leu Gln Val Glu Cys Phe Thr Trp Asp Gln Lys Leu Trp
545                 550                 555                 560

Cys Arg His Phe Cys Val Leu Ala Asp Ser Glu Ser Gly Gly His Ile
            565                 570                 575

Thr His Ser Gly Met Val Gly Met Gly Val Ser Cys Thr Val Thr Arg
        580                 585                 590

Glu Asp Gly Thr Asn Ala Ala Gln Pro Ala Asp Leu Gly Lys Lys Leu
        595                 600                 605

Leu Glu Ala Ala Arg Ala Gly Gln Asp Asp Glu Val Arg Ile Leu Met
    610                 615                 620

Ala Asn Gly Ala Asp Val Asn Ala Thr Asp Thr Leu Gly Arg Thr Pro
625                 630                 635                 640
```

-continued

```
Leu His Leu Ala Ala Gln Asn Gly His Leu Glu Ile Val Glu Val Leu
                645                 650                 655

Leu Lys His Ser Ala Asp Val Asn Ala Ile Glu Glu Val Gly Met Thr
        660                 665                 670

Pro Leu His Leu Ala Val Val Ala Gly His Leu Glu Ile Val Glu Val
    675                 680                 685

Leu Leu Lys Asn Gly Ala Asp Val Asn Ala Gln Asp Lys Phe Gly Lys
690                 695                 700

Thr Ala Phe Asp Ile Ser Ile Asp Tyr Gly Asn Glu Asp Leu Ala Glu
705                 710                 715                 720

Ile Leu Gln Lys Leu Asn Ala Ala Arg Gly Ser His His His His
                725                 730                 735

His His
```

<210> SEQ ID NO 3
<211> LENGTH: 2529
<212> TYPE: DNA
<213> ORGANISM: Artificial Sequence
<220> FEATURE:
<223> OTHER INFORMATION: Truncated and mutated (E501A, W504A, Q530A, E533A) NiV G protein (GcDelta34) fused to a single chain antibody directed to human CD8 (scFvC8-Vh1) linked with an additional (G4S)3 linker
<220> FEATURE:
<221> NAME/KEY: CDS
<222> LOCATION: (1)..(2529)

<400> SEQUENCE: 3

```
atg aag aag atc aac gag ggc ctg ctg gac agc aag atc ctg agc gcc        48
Met Lys Lys Ile Asn Glu Gly Leu Leu Asp Ser Lys Ile Leu Ser Ala
1               5                   10                  15 ttc aac acc gtg atc gcc ctg ctg ggc agc atc gtg atc att gtg atg        96
Phe Asn Thr Val Ile Ala Leu Leu Gly Ser Ile Val Ile Ile Val Met
                20                  25                  30 aac atc atg atc atc cag aac tac acc aga agc acc gac aac cag gcc       144
Asn Ile Met Ile Ile Gln Asn Tyr Thr Arg Ser Thr Asp Asn Gln Ala
            35                  40                  45 gtg atc aag gac gct ctc cag ggg atc cag cag cag atc aag ggc ctg       192
Val Ile Lys Asp Ala Leu Gln Gly Ile Gln Gln Gln Ile Lys Gly Leu
        50                  55                  60 gcc gac aag atc ggc acc gag atc ggc ccc aag gtg tcc ctg atc gac       240
Ala Asp Lys Ile Gly Thr Glu Ile Gly Pro Lys Val Ser Leu Ile Asp
65                  70                  75                  80 acc agc agc acc atc acc atc ccc gcc aac atc ggc ctg ctg ggg tcc       288
Thr Ser Ser Thr Ile Thr Ile Pro Ala Asn Ile Gly Leu Leu Gly Ser
                85                  90                  95 aag atc agc cag agc acc gcc agc atc aac gag aac gtg aac gag aag       336
Lys Ile Ser Gln Ser Thr Ala Ser Ile Asn Glu Asn Val Asn Glu Lys
                100                 105                 110 tgc aag ttc acc ctg ccc ccc ctg aag atc cac gag tgc aac atc agc       384
Cys Lys Phe Thr Leu Pro Pro Leu Lys Ile His Glu Cys Asn Ile Ser
            115                 120                 125 tgc ccc aac ccc ctg ccc ttc cgg gag tac cgg ccc cag acc gag ggc       432
Cys Pro Asn Pro Leu Pro Phe Arg Glu Tyr Arg Pro Gln Thr Glu Gly
        130                 135                 140 gtg agc aac ctg gtc ggc ctg ccc aac aac atc tgc ctg cag aaa acc       480
Val Ser Asn Leu Val Gly Leu Pro Asn Asn Ile Cys Leu Gln Lys Thr
145                 150                 155                 160 agc aac cag atc ctg aag ccc aag ctc att tcc tac acc ctg ccc gtg       528
Ser Asn Gln Ile Leu Lys Pro Lys Leu Ile Ser Tyr Thr Leu Pro Val
                165                 170                 175
```

```
gtg ggc cag agc ggc acc tgc atc acc gac ccc ctg ctg gcc atg gac      576
Val Gly Gln Ser Gly Thr Cys Ile Thr Asp Pro Leu Leu Ala Met Asp
            180                 185                 190 gag ggc tac ttc gcc tac agc cac ctg gaa cgg atc ggc agc tgc agc      624
Glu Gly Tyr Phe Ala Tyr Ser His Leu Glu Arg Ile Gly Ser Cys Ser
            195                 200                 205 agg ggc gtg tcc aag cag cgg atc atc ggc gtg ggc gag gtg ctg gac      672
Arg Gly Val Ser Lys Gln Arg Ile Ile Gly Val Gly Glu Val Leu Asp
    210                 215                 220 cgg ggc gac gag gtg ccc agc ctg ttc atg acc aac gtg tgg acc ccc      720
Arg Gly Asp Glu Val Pro Ser Leu Phe Met Thr Asn Val Trp Thr Pro
225                 230                 235                 240 ccc aac ccc aac acc gtg tac cac tgc agc gcc gtg tac aac aac gag      768
Pro Asn Pro Asn Thr Val Tyr His Cys Ser Ala Val Tyr Asn Asn Glu
                245                 250                 255 ttc tac tac gtg ctg tgc gcc gtg agc acc gtg ggc gac ccc atc ctg      816
Phe Tyr Tyr Val Leu Cys Ala Val Ser Thr Val Gly Asp Pro Ile Leu
            260                 265                 270 aac agc acc tac tgg tcc ggc agc ctg atg atg acc cgg ctg gcc gtg      864
Asn Ser Thr Tyr Trp Ser Gly Ser Leu Met Met Thr Arg Leu Ala Val
            275                 280                 285 aag cct aag agc aat ggc ggc gga tac aac cag cac cag ctg gcc ctg      912
Lys Pro Lys Ser Asn Gly Gly Gly Tyr Asn Gln His Gln Leu Ala Leu
    290                 295                 300 cgg agc atc gag aag ggc aga tac gac aaa gtg atg ccc tac ggc ccc      960
Arg Ser Ile Glu Lys Gly Arg Tyr Asp Lys Val Met Pro Tyr Gly Pro
305                 310                 315                 320 agc ggc atc aag cag ggc gac aca ctg tac ttc ccc gcc gtg ggc ttc     1008
Ser Gly Ile Lys Gln Gly Asp Thr Leu Tyr Phe Pro Ala Val Gly Phe
                325                 330                 335 ctg gtc cgg acc gag ttc aag tac aac gac agc aac tgc ccc atc acc     1056
Leu Val Arg Thr Glu Phe Lys Tyr Asn Asp Ser Asn Cys Pro Ile Thr
            340                 345                 350 aag tgc cag tac agc aag ccc gag aac tgc aga ctg agc atg ggc atc     1104
Lys Cys Gln Tyr Ser Lys Pro Glu Asn Cys Arg Leu Ser Met Gly Ile
            355                 360                 365 cgg ccc aac agc cac tac atc ctg cgg agc ggc ctg ctg aag tac aac     1152
Arg Pro Asn Ser His Tyr Ile Leu Arg Ser Gly Leu Leu Lys Tyr Asn
    370                 375                 380 ctg agc gac ggc gag aac ccc aaa gtc gtc ttt att gag atc agc gac     1200
Leu Ser Asp Gly Glu Asn Pro Lys Val Val Phe Ile Glu Ile Ser Asp
385                 390                 395                 400 cag cgg ctg tcc atc ggc agc ccc agc aag atc tac gac agc ctg ggc     1248
Gln Arg Leu Ser Ile Gly Ser Pro Ser Lys Ile Tyr Asp Ser Leu Gly
                405                 410                 415 cag ccc gtg ttc tac cag gcc agc ttc agc tgg gac acc atg atc aag     1296
Gln Pro Val Phe Tyr Gln Ala Ser Phe Ser Trp Asp Thr Met Ile Lys
            420                 425                 430 ttc ggc gac gtg ctg acc gtg aac ccc ctg gtg gtg aac tgg cgg aac     1344
Phe Gly Asp Val Leu Thr Val Asn Pro Leu Val Val Asn Trp Arg Asn
            435                 440                 445 aat acc gtg atc agc aga ccc ggc cag agc cag tgc ccc cgg ttc aac     1392
Asn Thr Val Ile Ser Arg Pro Gly Gln Ser Gln Cys Pro Arg Phe Asn
    450                 455                 460 acc tgc ccc gcg atc tgc gcg gag ggc gtg tac aac gac gcc ttc ctg     1440
Thr Cys Pro Ala Ile Cys Ala Glu Gly Val Tyr Asn Asp Ala Phe Leu
465                 470                 475                 480 atc gac cgg atc aac tgg atc tct gcc ggc gtg ttc ctg gac tcc aac     1488
Ile Asp Arg Ile Asn Trp Ile Ser Ala Gly Val Phe Leu Asp Ser Asn
```

-continued

|   |   |   |   |   |   |   |   |   |   |   |   |   |   |   |   |      |
|---|---|---|---|---|---|---|---|---|---|---|---|---|---|---|---|------|
|   |   |   |   | 485 |   |   |   |   | 490 |   |   |   |   | 495 |   |      |
| gcg | acc | gcc | gcg | aat | ccc | gtg | ttc | acc | gtg | ttt | aag | gac | aac | gag | atc | 1536 |
| Ala | Thr | Ala | Ala | Asn | Pro | Val | Phe | Thr | Val | Phe | Lys | Asp | Asn | Glu | Ile |      |
|     |     |     | 500 |     |     |     |     | 505 |     |     |     |     | 510 |     |     |      |
| ctg | tac | cgg | gcc | cag | ctg | gcc | agc | gag | gac | acc | aac | gcc | cag | aaa | acc | 1584 |
| Leu | Tyr | Arg | Ala | Gln | Leu | Ala | Ser | Glu | Asp | Thr | Asn | Ala | Gln | Lys | Thr |      |
|     |     | 515 |     |     |     |     | 520 |     |     |     |     | 525 |     |     |     |      |
| atc | acc | aac | tgc | ttt | ctg | ctg | aag | aac | aag | atc | tgg | tgc | atc | agc | ctg | 1632 |
| Ile | Thr | Asn | Cys | Phe | Leu | Leu | Lys | Asn | Lys | Ile | Trp | Cys | Ile | Ser | Leu |      |
|     | 530 |     |     |     |     | 535 |     |     |     |     | 540 |     |     |     |     |      |
| gtg | gag | atc | tac | gat | acc | ggc | gac | aac | gtg | atc | agg | ccc | aag | ctg | ttc | 1680 |
| Val | Glu | Ile | Tyr | Asp | Thr | Gly | Asp | Asn | Val | Ile | Arg | Pro | Lys | Leu | Phe |      |
| 545 |     |     |     |     | 550 |     |     |     |     | 555 |     |     |     |     | 560 |      |
| gcc | gtg | aag | atc | ccc | gag | cag | tgc | acc | ggt | gga | ggt | ggc | tct | ggt | gga | 1728 |
| Ala | Val | Lys | Ile | Pro | Glu | Gln | Cys | Thr | Gly | Gly | Gly | Gly | Ser | Gly | Gly |      |
|     |     |     |     | 565 |     |     |     |     | 570 |     |     |     |     | 575 |     |      |
| gga | ggc | tct | gga | ggt | ggt | gga | tca | gcg | gcc | cag | ccg | gcc | cag | gtg | cag | 1776 |
| Gly | Gly | Ser | Gly | Gly | Gly | Gly | Ser | Ala | Ala | Gln | Pro | Ala | Gln | Val | Gln |      |
|     |     |     | 580 |     |     |     |     | 585 |     |     |     |     | 590 |     |     |      |
| ctg | gtg | cag | agc | gga | gcc | gag | gat | aag | aaa | cct | ggc | gct | agc | gtg | aag | 1824 |
| Leu | Val | Gln | Ser | Gly | Ala | Glu | Asp | Lys | Lys | Pro | Gly | Ala | Ser | Val | Lys |      |
|     |     | 595 |     |     |     |     | 600 |     |     |     |     | 605 |     |     |     |      |
| gtg | tcc | tgc | aag | gcc | agc | ggc | ttc | aac | atc | aag | gac | acc | tac | atc | cac | 1872 |
| Val | Ser | Cys | Lys | Ala | Ser | Gly | Phe | Asn | Ile | Lys | Asp | Thr | Tyr | Ile | His |      |
|     | 610 |     |     |     |     | 615 |     |     |     |     | 620 |     |     |     |     |      |
| tgg | gtg | cgc | cag | gct | cca | gga | cag | ggc | ctg | gaa | tgg | atg | ggc | cgg | atc | 1920 |
| Trp | Val | Arg | Gln | Ala | Pro | Gly | Gln | Gly | Leu | Glu | Trp | Met | Gly | Arg | Ile |      |
| 625 |     |     |     |     | 630 |     |     |     |     | 635 |     |     |     |     | 640 |      |
| gac | ccc | gcc | aac | gac | aac | acc | ctg | tac | gcc | agc | aag | ttc | cag | ggc | aga | 1968 |
| Asp | Pro | Ala | Asn | Asp | Asn | Thr | Leu | Tyr | Ala | Ser | Lys | Phe | Gln | Gly | Arg |      |
|     |     |     |     | 645 |     |     |     |     | 650 |     |     |     |     | 655 |     |      |
| gtg | acc | atc | acc | gcc | gac | acc | agc | agc | aac | acc | gcc | tac | atg | gaa | ctg | 2016 |
| Val | Thr | Ile | Thr | Ala | Asp | Thr | Ser | Ser | Asn | Thr | Ala | Tyr | Met | Glu | Leu |      |
|     |     |     | 660 |     |     |     |     | 665 |     |     |     |     | 670 |     |     |      |
| agc | agc | ctg | aga | agc | gag | gac | acc | gcc | gtg | tac | tac | tgt | ggc | aga | ggc | 2064 |
| Ser | Ser | Leu | Arg | Ser | Glu | Asp | Thr | Ala | Val | Tyr | Tyr | Cys | Gly | Arg | Gly |      |
|     |     | 675 |     |     |     |     | 680 |     |     |     |     | 685 |     |     |     |      |
| tac | ggc | tac | tac | gtg | ttc | gac | cac | tgg | ggc | cag | ggc | acc | acc | gtg | aca | 2112 |
| Tyr | Gly | Tyr | Tyr | Val | Phe | Asp | His | Trp | Gly | Gln | Gly | Thr | Thr | Val | Thr |      |
|     | 690 |     |     |     |     | 695 |     |     |     |     | 700 |     |     |     |     |      |
| gtg | tct | agc | ggc | gga | ggc | gga | agt | gga | ggc | gga | gga | agc | gga | ggc | ggc | 2160 |
| Val | Ser | Ser | Gly | Gly | Gly | Gly | Ser | Gly | Gly | Gly | Gly | Ser | Gly | Gly | Gly |      |
| 705 |     |     |     |     | 710 |     |     |     |     | 715 |     |     |     |     | 720 |      |
| gga | tcc | gac | atc | gtg | atg | acc | cag | agc | cct | agc | agc | ctg | tct | gcc | agc | 2208 |
| Gly | Ser | Asp | Ile | Val | Met | Thr | Gln | Ser | Pro | Ser | Ser | Leu | Ser | Ala | Ser |      |
|     |     |     |     | 725 |     |     |     |     | 730 |     |     |     |     | 735 |     |      |
| gtg | ggc | gac | cgc | gtg | acc | att | acc | tgc | cgg | acc | agc | cgg | tcc | atc | agc | 2256 |
| Val | Gly | Asp | Arg | Val | Thr | Ile | Thr | Cys | Arg | Thr | Ser | Arg | Ser | Ile | Ser |      |
|     |     |     | 740 |     |     |     |     | 745 |     |     |     |     | 750 |     |     |      |
| cag | tac | ctg | gcc | tgg | tat | cag | gaa | aag | ccc | ggc | aag | gcc | ccc | aag | ctg | 2304 |
| Gln | Tyr | Leu | Ala | Trp | Tyr | Gln | Glu | Lys | Pro | Gly | Lys | Ala | Pro | Lys | Leu |      |
|     |     | 755 |     |     |     |     | 760 |     |     |     |     | 765 |     |     |     |      |
| ctg | atc | tac | agc | ggc | agc | acc | ctg | cag | agc | ggc | gtg | cca | agc | aga | ttc | 2352 |
| Leu | Ile | Tyr | Ser | Gly | Ser | Thr | Leu | Gln | Ser | Gly | Val | Pro | Ser | Arg | Phe |      |
|     | 770 |     |     |     |     | 775 |     |     |     |     | 780 |     |     |     |     |      |
| agc | ggc | agc | ggc | tcc | ggc | acc | gac | ttc | acc | ctg | acc | atc | agc | agc | ctg | 2400 |
| Ser | Gly | Ser | Gly | Ser | Gly | Thr | Asp | Phe | Thr | Leu | Thr | Ile | Ser | Ser | Leu |      |
| 785 |     |     |     |     | 790 |     |     |     |     | 795 |     |     |     |     | 800 |      |
| cag | ccc | gag | gac | ttc | gcc | acc | tac | tac | tgc | cag | cag | cac | aac | gag | aac | 2448 |

```
                Gln Pro Glu Asp Phe Ala Thr Tyr Tyr Cys Gln Gln His Asn Glu Asn
                                805                 810                 815 ccc ctg acc ttc ggg cag gga aca aag gtg gag atc aag aga gcg gcc                 2496
Pro Leu Thr Phe Gly Gln Gly Thr Lys Val Glu Ile Lys Arg Ala Ala
            820                 825                 830 gca aga ggt tct cat cac cat cac cat cac taa                                     2529
Ala Arg Gly Ser His His His His His His
        835                 840

<210> SEQ ID NO 4
<211> LENGTH: 842
<212> TYPE: PRT
<213> ORGANISM: Artificial Sequence
<220> FEATURE:
<223> OTHER INFORMATION: Synthetic Construct

<400> SEQUENCE: 4

Met Lys Lys Ile Asn Glu Gly Leu Leu Asp Ser Lys Ile Leu Ser Ala
1               5                   10                  15

Phe Asn Thr Val Ile Ala Leu Leu Gly Ser Ile Val Ile Ile Val Met
                20                  25                  30

Asn Ile Met Ile Ile Gln Asn Tyr Thr Arg Ser Thr Asp Asn Gln Ala
            35                  40                  45

Val Ile Lys Asp Ala Leu Gln Gly Ile Gln Gln Ile Lys Gly Leu
        50                  55                  60

Ala Asp Lys Ile Gly Thr Glu Ile Gly Pro Lys Val Ser Leu Ile Asp
65                  70                  75                  80

Thr Ser Ser Thr Ile Thr Ile Pro Ala Asn Ile Gly Leu Leu Gly Ser
                85                  90                  95

Lys Ile Ser Gln Ser Thr Ala Ser Ile Asn Glu Asn Val Asn Glu Lys
            100                 105                 110

Cys Lys Phe Thr Leu Pro Pro Leu Lys Ile His Glu Cys Asn Ile Ser
        115                 120                 125

Cys Pro Asn Pro Leu Pro Phe Arg Glu Tyr Arg Pro Gln Thr Glu Gly
    130                 135                 140

Val Ser Asn Leu Val Gly Leu Pro Asn Asn Ile Cys Leu Gln Lys Thr
145                 150                 155                 160

Ser Asn Gln Ile Leu Lys Pro Lys Leu Ile Ser Tyr Thr Leu Pro Val
                165                 170                 175

Val Gly Gln Ser Gly Thr Cys Ile Thr Asp Pro Leu Leu Ala Met Asp
            180                 185                 190

Glu Gly Tyr Phe Ala Tyr Ser His Leu Glu Arg Ile Gly Ser Cys Ser
        195                 200                 205

Arg Gly Val Ser Lys Gln Arg Ile Ile Gly Val Gly Glu Val Leu Asp
    210                 215                 220

Arg Gly Asp Glu Val Pro Ser Leu Phe Met Thr Asn Val Trp Thr Pro
225                 230                 235                 240

Pro Asn Pro Asn Thr Val Tyr His Cys Ser Ala Val Tyr Asn Asn Glu
                245                 250                 255

Phe Tyr Tyr Val Leu Cys Ala Val Ser Thr Val Gly Asp Pro Ile Leu
            260                 265                 270

Asn Ser Thr Tyr Trp Ser Gly Ser Leu Met Met Thr Arg Leu Ala Val
        275                 280                 285

Lys Pro Lys Ser Asn Gly Gly Tyr Asn Gln His Gln Leu Ala Leu
    290                 295                 300

Arg Ser Ile Glu Lys Gly Arg Tyr Asp Lys Val Met Pro Tyr Gly Pro
```

```
            305                 310                 315                 320
Ser Gly Ile Lys Gln Gly Asp Thr Leu Tyr Phe Pro Ala Val Gly Phe
                    325                 330                 335

Leu Val Arg Thr Glu Phe Lys Tyr Asn Asp Ser Asn Cys Pro Ile Thr
                    340                 345                 350

Lys Cys Gln Tyr Ser Lys Pro Glu Asn Cys Arg Leu Ser Met Gly Ile
                    355                 360                 365

Arg Pro Asn Ser His Tyr Ile Leu Arg Ser Gly Leu Leu Lys Tyr Asn
            370                 375                 380

Leu Ser Asp Gly Glu Asn Pro Lys Val Val Phe Ile Glu Ile Ser Asp
385                 390                 395                 400

Gln Arg Leu Ser Ile Gly Ser Pro Ser Lys Ile Tyr Asp Ser Leu Gly
                    405                 410                 415

Gln Pro Val Phe Tyr Gln Ala Ser Phe Ser Trp Asp Thr Met Ile Lys
                    420                 425                 430

Phe Gly Asp Val Leu Thr Val Asn Pro Leu Val Val Asn Trp Arg Asn
            435                 440                 445

Asn Thr Val Ile Ser Arg Pro Gly Gln Ser Gln Cys Pro Arg Phe Asn
            450                 455                 460

Thr Cys Pro Ala Ile Cys Ala Glu Gly Val Tyr Asn Asp Ala Phe Leu
465                 470                 475                 480

Ile Asp Arg Ile Asn Trp Ile Ser Ala Gly Val Phe Leu Asp Ser Asn
                    485                 490                 495

Ala Thr Ala Ala Asn Pro Val Phe Thr Val Phe Lys Asp Asn Glu Ile
                    500                 505                 510

Leu Tyr Arg Ala Gln Leu Ala Ser Glu Asp Thr Asn Ala Gln Lys Thr
            515                 520                 525

Ile Thr Asn Cys Phe Leu Leu Lys Asn Lys Ile Trp Cys Ile Ser Leu
            530                 535                 540

Val Glu Ile Tyr Asp Thr Gly Asp Asn Val Ile Arg Pro Lys Leu Phe
545                 550                 555                 560

Ala Val Lys Ile Pro Glu Gln Cys Thr Gly Gly Gly Ser Gly Gly
                    565                 570                 575

Gly Gly Ser Gly Gly Gly Ser Ala Ala Gln Pro Ala Gln Val Gln
                    580                 585                 590

Leu Val Gln Ser Gly Ala Glu Asp Lys Lys Pro Gly Ala Ser Val Lys
            595                 600                 605

Val Ser Cys Lys Ala Ser Gly Phe Asn Ile Lys Asp Thr Tyr Ile His
            610                 615                 620

Trp Val Arg Gln Ala Pro Gly Gln Gly Leu Glu Trp Met Gly Arg Ile
625                 630                 635                 640

Asp Pro Ala Asn Asp Asn Thr Leu Tyr Ala Ser Lys Phe Gln Gly Arg
                    645                 650                 655

Val Thr Ile Thr Ala Asp Thr Ser Ser Asn Thr Ala Tyr Met Glu Leu
                    660                 665                 670

Ser Ser Leu Arg Ser Glu Asp Thr Ala Val Tyr Tyr Cys Gly Arg Gly
            675                 680                 685

Tyr Gly Tyr Tyr Val Phe Asp His Trp Gly Gln Gly Thr Thr Val Thr
            690                 695                 700

Val Ser Ser Gly Gly Gly Gly Ser Gly Gly Gly Gly Ser Gly Gly Gly
705                 710                 715                 720

Gly Ser Asp Ile Val Met Thr Gln Ser Pro Ser Ser Leu Ser Ala Ser
                    725                 730                 735
```

```
Val Gly Asp Arg Val Thr Ile Thr Cys Arg Thr Ser Arg Ser Ile Ser
            740                 745                 750

Gln Tyr Leu Ala Trp Tyr Gln Glu Lys Pro Gly Lys Ala Pro Lys Leu
        755                 760                 765

Leu Ile Tyr Ser Gly Ser Thr Leu Gln Ser Gly Val Pro Ser Arg Phe
    770                 775                 780

Ser Gly Ser Gly Ser Gly Thr Asp Phe Thr Leu Thr Ile Ser Ser Leu
785                 790                 795                 800

Gln Pro Glu Asp Phe Ala Thr Tyr Tyr Cys Gln Gln His Asn Glu Asn
                805                 810                 815

Pro Leu Thr Phe Gly Gln Gly Thr Lys Val Glu Ile Lys Arg Ala Ala
            820                 825                 830

Ala Arg Gly Ser His His His His His His
        835                 840

<210> SEQ ID NO 5
<211> LENGTH: 2211
<212> TYPE: DNA
<213> ORGANISM: Artificial Sequence
<220> FEATURE:
<223> OTHER INFORMATION: Truncated and mutated (E501A, W504A, Q530A,
      E533A) NiV G protein (GcDelta34) fused to IL-7
<220> FEATURE:
<221> NAME/KEY: CDS
<222> LOCATION: (1)..(2211)

<400> SEQUENCE: 5 atg aag aag atc aac gag ggc ctg ctg gac agc aag atc ctg agc gcc      48
Met Lys Lys Ile Asn Glu Gly Leu Leu Asp Ser Lys Ile Leu Ser Ala
1               5                   10                  15 ttc aac acc gtg atc gcc ctg ctg ggc agc atc gtg atc att gtg atg      96
Phe Asn Thr Val Ile Ala Leu Leu Gly Ser Ile Val Ile Ile Val Met
                20                  25                  30 aac atc atg atc atc cag aac tac acc aga agc acc gac aac cag gcc     144
Asn Ile Met Ile Ile Gln Asn Tyr Thr Arg Ser Thr Asp Asn Gln Ala
            35                  40                  45 gtg atc aag gac gct ctc cag ggg atc cag cag cag atc aag ggc ctg     192
Val Ile Lys Asp Ala Leu Gln Gly Ile Gln Gln Gln Ile Lys Gly Leu
        50                  55                  60 gcc gac aag atc ggc acc gag atc ggc ccc aag gtg tcc ctg atc gac     240
Ala Asp Lys Ile Gly Thr Glu Ile Gly Pro Lys Val Ser Leu Ile Asp
65                  70                  75                  80 acc agc agc acc atc acc atc ccc gcc aac atc ggc ctg ctg ggg tcc     288
Thr Ser Ser Thr Ile Thr Ile Pro Ala Asn Ile Gly Leu Leu Gly Ser
                85                  90                  95 aag atc agc cag agc acc gcc agc atc aac gag aac gtg aac gag aag     336
Lys Ile Ser Gln Ser Thr Ala Ser Ile Asn Glu Asn Val Asn Glu Lys
            100                 105                 110 tgc aag ttc acc ctg ccc ccc ctg aag atc cac gag tgc aac atc agc     384
Cys Lys Phe Thr Leu Pro Pro Leu Lys Ile His Glu Cys Asn Ile Ser
        115                 120                 125 tgc ccc aac ccc ctg ccc ttc cgg gag tac cgg ccc cag acc gag ggc     432
Cys Pro Asn Pro Leu Pro Phe Arg Glu Tyr Arg Pro Gln Thr Glu Gly
    130                 135                 140 gtg agc aac ctg gtc ggc ctg ccc aac aac atc tgc ctg cag aaa acc     480
Val Ser Asn Leu Val Gly Leu Pro Asn Asn Ile Cys Leu Gln Lys Thr
145                 150                 155                 160 agc aac cag atc ctg aag ccc aag ctc att tcc tac acc ctg ccc gtg     528
Ser Asn Gln Ile Leu Lys Pro Lys Leu Ile Ser Tyr Thr Leu Pro Val
                165                 170                 175
```

-continued

| | | | | | | | | | | | | | | | | |
|---|---|---|---|---|---|---|---|---|---|---|---|---|---|---|---|---|
| gtg | ggc | cag | agc | ggc | acc | tgc | atc | acc | gac | ccc | ctg | ctg | gcc | atg | gac | 576 |
| Val | Gly | Gln | Ser | Gly | Thr | Cys | Ile | Thr | Asp | Pro | Leu | Leu | Ala | Met | Asp | |
| | | | 180 | | | | 185 | | | | 190 | | | | | |
| gag | ggc | tac | ttc | gcc | tac | agc | cac | ctg | gaa | cgg | atc | ggc | agc | tgc | agc | 624 |
| Glu | Gly | Tyr | Phe | Ala | Tyr | Ser | His | Leu | Glu | Arg | Ile | Gly | Ser | Cys | Ser | |
| | | 195 | | | | | 200 | | | | | 205 | | | | |
| agg | ggc | gtg | tcc | aag | cag | cgg | atc | atc | ggc | gtg | ggc | gag | gtg | ctg | gac | 672 |
| Arg | Gly | Val | Ser | Lys | Gln | Arg | Ile | Ile | Gly | Val | Gly | Glu | Val | Leu | Asp | |
| | 210 | | | | | 215 | | | | | 220 | | | | | |
| cgg | ggc | gac | gag | gtg | ccc | agc | ctg | ttc | atg | acc | aac | gtg | tgg | acc | ccc | 720 |
| Arg | Gly | Asp | Glu | Val | Pro | Ser | Leu | Phe | Met | Thr | Asn | Val | Trp | Thr | Pro | |
| 225 | | | | | 230 | | | | | 235 | | | | | 240 | |
| ccc | aac | ccc | aac | acc | gtg | tac | cac | tgc | agc | gcc | gtg | tac | aac | aac | gag | 768 |
| Pro | Asn | Pro | Asn | Thr | Val | Tyr | His | Cys | Ser | Ala | Val | Tyr | Asn | Asn | Glu | |
| | | | | 245 | | | | | 250 | | | | | 255 | | |
| ttc | tac | tac | gtg | ctg | tgc | gcc | gtg | agc | acc | gtg | ggc | gac | ccc | atc | ctg | 816 |
| Phe | Tyr | Tyr | Val | Leu | Cys | Ala | Val | Ser | Thr | Val | Gly | Asp | Pro | Ile | Leu | |
| | | | 260 | | | | | 265 | | | | | 270 | | | |
| aac | agc | acc | tac | tgg | tcc | ggc | agc | ctg | atg | atg | acc | cgg | ctg | gcc | gtg | 864 |
| Asn | Ser | Thr | Tyr | Trp | Ser | Gly | Ser | Leu | Met | Met | Thr | Arg | Leu | Ala | Val | |
| | | 275 | | | | | 280 | | | | | 285 | | | | |
| aag | cct | aag | agc | aat | ggc | ggc | gga | tac | aac | cag | cac | cag | ctg | gcc | ctg | 912 |
| Lys | Pro | Lys | Ser | Asn | Gly | Gly | Gly | Tyr | Asn | Gln | His | Gln | Leu | Ala | Leu | |
| | 290 | | | | | 295 | | | | | 300 | | | | | |
| cgg | agc | atc | gag | aag | ggc | aga | tac | gac | aaa | gtg | atg | ccc | tac | ggc | ccc | 960 |
| Arg | Ser | Ile | Glu | Lys | Gly | Arg | Tyr | Asp | Lys | Val | Met | Pro | Tyr | Gly | Pro | |
| 305 | | | | | 310 | | | | | 315 | | | | | 320 | |
| agc | ggc | atc | aag | cag | ggc | gac | aca | ctg | tac | ttc | ccc | gcc | gtg | ggc | ttc | 1008 |
| Ser | Gly | Ile | Lys | Gln | Gly | Asp | Thr | Leu | Tyr | Phe | Pro | Ala | Val | Gly | Phe | |
| | | | | 325 | | | | | 330 | | | | | 335 | | |
| ctg | gtc | cgg | acc | gag | ttc | aag | tac | aac | gac | agc | aac | tgc | ccc | atc | acc | 1056 |
| Leu | Val | Arg | Thr | Glu | Phe | Lys | Tyr | Asn | Asp | Ser | Asn | Cys | Pro | Ile | Thr | |
| | | | 340 | | | | | 345 | | | | | 350 | | | |
| aag | tgc | cag | tac | agc | aag | ccc | gag | aac | tgc | aga | ctg | agc | atg | ggc | atc | 1104 |
| Lys | Cys | Gln | Tyr | Ser | Lys | Pro | Glu | Asn | Cys | Arg | Leu | Ser | Met | Gly | Ile | |
| | | 355 | | | | | 360 | | | | | 365 | | | | |
| cgg | ccc | aac | agc | cac | tac | atc | ctg | cgg | agc | ggc | ctg | ctg | aag | tac | aac | 1152 |
| Arg | Pro | Asn | Ser | His | Tyr | Ile | Leu | Arg | Ser | Gly | Leu | Leu | Lys | Tyr | Asn | |
| 370 | | | | | 375 | | | | | 380 | | | | | | |
| ctg | agc | gac | ggc | gag | aac | ccc | aaa | gtc | gtc | ttt | att | gag | atc | agc | gac | 1200 |
| Leu | Ser | Asp | Gly | Glu | Asn | Pro | Lys | Val | Val | Phe | Ile | Glu | Ile | Ser | Asp | |
| 385 | | | | | 390 | | | | | 395 | | | | | 400 | |
| cag | cgg | ctg | tcc | atc | ggc | agc | ccc | agc | aag | atc | tac | gac | agc | ctg | ggc | 1248 |
| Gln | Arg | Leu | Ser | Ile | Gly | Ser | Pro | Ser | Lys | Ile | Tyr | Asp | Ser | Leu | Gly | |
| | | | | 405 | | | | | 410 | | | | | 415 | | |
| cag | ccc | gtg | ttc | tac | cag | gcc | agc | ttc | agc | tgg | gac | acc | atg | atc | aag | 1296 |
| Gln | Pro | Val | Phe | Tyr | Gln | Ala | Ser | Phe | Ser | Trp | Asp | Thr | Met | Ile | Lys | |
| | | | 420 | | | | | 425 | | | | | 430 | | | |
| ttc | ggc | gac | gtg | ctg | acc | gtg | aac | ccc | ctg | gtg | gtg | aac | tgg | cgg | aac | 1344 |
| Phe | Gly | Asp | Val | Leu | Thr | Val | Asn | Pro | Leu | Val | Val | Asn | Trp | Arg | Asn | |
| | | 435 | | | | | 440 | | | | | 445 | | | | |
| aat | acc | gtg | atc | agc | aga | ccc | ggc | cag | agc | cag | tgc | ccc | cgg | ttc | aac | 1392 |
| Asn | Thr | Val | Ile | Ser | Arg | Pro | Gly | Gln | Ser | Gln | Cys | Pro | Arg | Phe | Asn | |
| 450 | | | | | 455 | | | | | 460 | | | | | | |
| acc | tgc | ccc | gcg | atc | tgc | gcg | gag | ggc | gtg | tac | aac | gac | gcc | ttc | ctg | 1440 |
| Thr | Cys | Pro | Ala | Ile | Cys | Ala | Glu | Gly | Val | Tyr | Asn | Asp | Ala | Phe | Leu | |
| 465 | | | | 470 | | | | | 475 | | | | | 480 | | |
| atc | gac | cgg | atc | aac | tgg | atc | tct | gcc | ggc | gtg | ttc | ctg | gac | tcc | aac | 1488 |
| Ile | Asp | Arg | Ile | Asn | Trp | Ile | Ser | Ala | Gly | Val | Phe | Leu | Asp | Ser | Asn | |

```
                        485                 490                 495
gcg acc gcc gcg aat ccc gtg ttc acc gtg ttt aag gac aac gag atc     1536
Ala Thr Ala Ala Asn Pro Val Phe Thr Val Phe Lys Asp Asn Glu Ile
            500                 505                 510 ctg tac cgg gcc cag ctg gcc agc gag gac acc aac gcc cag aaa acc     1584
Leu Tyr Arg Ala Gln Leu Ala Ser Glu Asp Thr Asn Ala Gln Lys Thr
        515                 520                 525 atc acc aac tgc ttt ctg ctg aag aac aag atc tgg tgc atc agc ctg     1632
Ile Thr Asn Cys Phe Leu Leu Lys Asn Lys Ile Trp Cys Ile Ser Leu
    530                 535                 540 gtg gag atc tac gat acc ggc gac aac gtg atc agg ccc aag ctg ttc     1680
Val Glu Ile Tyr Asp Thr Gly Asp Asn Val Ile Arg Pro Lys Leu Phe
545                 550                 555                 560 gcc gtg aag atc ccc gag cag tgc acc ggt atg gcc gat tgt gat att     1728
Ala Val Lys Ile Pro Glu Gln Cys Thr Gly Met Ala Asp Cys Asp Ile
                565                 570                 575 gaa ggt aaa gat ggc aaa caa tat gag agt gtt cta atg gtc agc atc     1776
Glu Gly Lys Asp Gly Lys Gln Tyr Glu Ser Val Leu Met Val Ser Ile
            580                 585                 590 gat caa tta ttg gac agc atg aaa gaa att ggt agc aat tgc ctg aat     1824
Asp Gln Leu Leu Asp Ser Met Lys Glu Ile Gly Ser Asn Cys Leu Asn
        595                 600                 605 aat gaa ttt aac ttt ttt aaa aga cat atc tgt gat gct aat aag gaa     1872
Asn Glu Phe Asn Phe Phe Lys Arg His Ile Cys Asp Ala Asn Lys Glu
    610                 615                 620 ggt atg ttt tta ttc cgt gct gct cgc aag ttg agg caa ttt ctt aaa     1920
Gly Met Phe Leu Phe Arg Ala Ala Arg Lys Leu Arg Gln Phe Leu Lys
625                 630                 635                 640 atg aat agc act ggt gat ttt gat ctc cac tta tta aaa gtt tca gaa     1968
Met Asn Ser Thr Gly Asp Phe Asp Leu His Leu Leu Lys Val Ser Glu
                645                 650                 655 ggc aca aca ata ctg ttg aac tgc act ggc cag gtt aaa gga aga aaa     2016
Gly Thr Thr Ile Leu Leu Asn Cys Thr Gly Gln Val Lys Gly Arg Lys
            660                 665                 670 cca gct gcc ctg ggt gaa gcc caa cca aca aag agt ttg gaa gaa aat     2064
Pro Ala Ala Leu Gly Glu Ala Gln Pro Thr Lys Ser Leu Glu Glu Asn
        675                 680                 685 aaa tct tta aag gaa cag aaa aaa ctg aat gac ttg tgt ttc cta aag     2112
Lys Ser Leu Lys Glu Gln Lys Lys Leu Asn Asp Leu Cys Phe Leu Lys
    690                 695                 700 aga cta tta caa gag ata aaa act tgt tgg aat aaa att ttg atg ggc     2160
Arg Leu Leu Gln Glu Ile Lys Thr Cys Trp Asn Lys Ile Leu Met Gly
705                 710                 715                 720 act aaa gaa cac gcg gcc gca aga ggt tct cat cac cat cac cat cac     2208
Thr Lys Glu His Ala Ala Ala Arg Gly Ser His His His His His His
                725                 730                 735 taa                                                                  2211
```

<210> SEQ ID NO 6
<211> LENGTH: 736
<212> TYPE: PRT
<213> ORGANISM: Artificial Sequence
<220> FEATURE:
<223> OTHER INFORMATION: Synthetic Construct

<400> SEQUENCE: 6

```
Met Lys Lys Ile Asn Glu Gly Leu Leu Asp Ser Lys Ile Leu Ser Ala
1               5                   10                  15

Phe Asn Thr Val Ile Ala Leu Leu Gly Ser Ile Val Ile Val Met
            20                  25                  30
```

```
Asn Ile Met Ile Ile Gln Asn Tyr Thr Arg Ser Thr Asp Asn Gln Ala
         35                  40                  45

Val Ile Lys Asp Ala Leu Gln Gly Ile Gln Gln Ile Lys Gly Leu
 50                  55                  60

Ala Asp Lys Ile Gly Thr Glu Ile Gly Pro Lys Val Ser Leu Ile Asp
 65                  70                  75                  80

Thr Ser Ser Thr Ile Thr Ile Pro Ala Asn Ile Gly Leu Leu Gly Ser
                 85                  90                  95

Lys Ile Ser Gln Ser Thr Ala Ser Ile Asn Glu Asn Val Asn Glu Lys
                100                 105                 110

Cys Lys Phe Thr Leu Pro Pro Leu Lys Ile His Glu Cys Asn Ile Ser
            115                 120                 125

Cys Pro Asn Pro Leu Pro Phe Arg Glu Tyr Arg Pro Gln Thr Glu Gly
        130                 135                 140

Val Ser Asn Leu Val Gly Leu Pro Asn Asn Ile Cys Leu Gln Lys Thr
145                 150                 155                 160

Ser Asn Gln Ile Leu Lys Pro Lys Leu Ile Ser Tyr Thr Leu Pro Val
                165                 170                 175

Val Gly Gln Ser Gly Thr Cys Ile Thr Asp Pro Leu Leu Ala Met Asp
            180                 185                 190

Glu Gly Tyr Phe Ala Tyr Ser His Leu Glu Arg Ile Gly Ser Cys Ser
        195                 200                 205

Arg Gly Val Ser Lys Gln Arg Ile Ile Gly Val Gly Glu Val Leu Asp
210                 215                 220

Arg Gly Asp Glu Val Pro Ser Leu Phe Met Thr Asn Val Trp Thr Pro
225                 230                 235                 240

Pro Asn Pro Asn Thr Val Tyr His Cys Ser Ala Val Tyr Asn Asn Glu
                245                 250                 255

Phe Tyr Tyr Val Leu Cys Ala Val Ser Thr Val Gly Asp Pro Ile Leu
            260                 265                 270

Asn Ser Thr Tyr Trp Ser Gly Ser Leu Met Met Thr Arg Leu Ala Val
        275                 280                 285

Lys Pro Lys Ser Asn Gly Gly Gly Tyr Asn Gln His Gln Leu Ala Leu
290                 295                 300

Arg Ser Ile Glu Lys Gly Arg Tyr Asp Lys Val Met Pro Tyr Gly Pro
305                 310                 315                 320

Ser Gly Ile Lys Gln Gly Asp Thr Leu Tyr Phe Pro Ala Val Gly Phe
                325                 330                 335

Leu Val Arg Thr Glu Phe Lys Tyr Asn Asp Ser Asn Cys Pro Ile Thr
            340                 345                 350

Lys Cys Gln Tyr Ser Lys Pro Glu Asn Cys Arg Leu Ser Met Gly Ile
        355                 360                 365

Arg Pro Asn Ser His Tyr Ile Leu Arg Ser Gly Leu Leu Lys Tyr Asn
370                 375                 380

Leu Ser Asp Gly Glu Asn Pro Lys Val Val Phe Ile Glu Ile Ser Asp
385                 390                 395                 400

Gln Arg Leu Ser Ile Gly Ser Pro Ser Lys Ile Tyr Asp Ser Leu Gly
                405                 410                 415

Gln Pro Val Phe Tyr Gln Ala Ser Phe Ser Trp Asp Thr Met Ile Lys
            420                 425                 430

Phe Gly Asp Val Leu Thr Val Asn Pro Leu Val Val Asn Trp Arg Asn
        435                 440                 445
```

```
Asn Thr Val Ile Ser Arg Pro Gly Gln Ser Gln Cys Pro Arg Phe Asn
            450                 455                 460

Thr Cys Pro Ala Ile Cys Ala Glu Gly Val Tyr Asn Asp Ala Phe Leu
465                 470                 475                 480

Ile Asp Arg Ile Asn Trp Ile Ser Ala Gly Val Phe Leu Asp Ser Asn
                485                 490                 495

Ala Thr Ala Ala Asn Pro Val Phe Thr Val Phe Lys Asp Asn Glu Ile
            500                 505                 510

Leu Tyr Arg Ala Gln Leu Ala Ser Glu Asp Thr Asn Ala Gln Lys Thr
        515                 520                 525

Ile Thr Asn Cys Phe Leu Leu Lys Asn Lys Ile Trp Cys Ile Ser Leu
    530                 535                 540

Val Glu Ile Tyr Asp Thr Gly Asp Asn Val Ile Arg Pro Lys Leu Phe
545                 550                 555                 560

Ala Val Lys Ile Pro Glu Gln Cys Thr Gly Met Ala Asp Cys Asp Ile
                565                 570                 575

Glu Gly Lys Asp Gly Lys Gln Tyr Glu Ser Val Leu Met Val Ser Ile
            580                 585                 590

Asp Gln Leu Leu Asp Ser Met Lys Glu Ile Gly Ser Asn Cys Leu Asn
        595                 600                 605

Asn Glu Phe Asn Phe Lys Arg His Ile Cys Asp Ala Asn Lys Glu
    610                 615                 620

Gly Met Phe Leu Phe Arg Ala Ala Arg Lys Leu Arg Gln Phe Leu Lys
625                 630                 635                 640

Met Asn Ser Thr Gly Asp Phe Asp Leu His Leu Leu Lys Val Ser Glu
                645                 650                 655

Gly Thr Thr Ile Leu Leu Asn Cys Thr Gly Gln Val Lys Gly Arg Lys
            660                 665                 670

Pro Ala Ala Leu Gly Glu Ala Gln Pro Thr Lys Ser Leu Glu Glu Asn
        675                 680                 685

Lys Ser Leu Lys Glu Gln Lys Lys Leu Asn Asp Leu Cys Phe Leu Lys
    690                 695                 700

Arg Leu Leu Gln Glu Ile Lys Thr Cys Trp Asn Lys Ile Leu Met Gly
705                 710                 715                 720

Thr Lys Glu His Ala Ala Ala Arg Gly Ser His His His His His His
                725                 730                 735

<210> SEQ ID NO 7
<211> LENGTH: 2229
<212> TYPE: DNA
<213> ORGANISM: Artificial Sequence
<220> FEATURE:
<223> OTHER INFORMATION: Truncated and mutated (E501A, W504A, Q530A,
      E533A) NiV G protein (GcDelta34) fused to a designed ankaryin
      repeat protein (DARPin) directed against human EpCAM
<220> FEATURE:
<221> NAME/KEY: CDS
<222> LOCATION: (1)..(2229)

<400> SEQUENCE: 7 atg aag aag atc aac gag ggc ctg ctg gac agc aag atc ctg agc gcc      48
Met Lys Lys Ile Asn Glu Gly Leu Leu Asp Ser Lys Ile Leu Ser Ala
1               5                   10                  15 ttc aac acc gtg atc gcc ctg ctg ggc agc atc gtg atc att gtg atg      96
Phe Asn Thr Val Ile Ala Leu Leu Gly Ser Ile Val Ile Ile Val Met
                20                  25                  30 aac atc atg atc atc cag aac tac acc aga agc acc gac aac cag gcc     144
Asn Ile Met Ile Ile Gln Asn Tyr Thr Arg Ser Thr Asp Asn Gln Ala
```

```
                  35                  40                  45
gtg atc aag gac gct ctc cag ggg atc cag cag cag atc aag ggc ctg      192
Val Ile Lys Asp Ala Leu Gln Gly Ile Gln Gln Gln Ile Lys Gly Leu
 50                  55                  60 gcc gac aag atc ggc acc gag atc ggc ccc aag gtg tcc ctg atc gac      240
Ala Asp Lys Ile Gly Thr Glu Ile Gly Pro Lys Val Ser Leu Ile Asp
 65                  70                  75                  80 acc agc agc acc atc acc atc ccc gcc aac atc ggc ctg ctg ggg tcc      288
Thr Ser Ser Thr Ile Thr Ile Pro Ala Asn Ile Gly Leu Leu Gly Ser
                 85                  90                  95 aag atc agc cag agc acc gcc agc atc aac gag aac gtg aac gag aag      336
Lys Ile Ser Gln Ser Thr Ala Ser Ile Asn Glu Asn Val Asn Glu Lys
            100                 105                 110 tgc aag ttc acc ctg ccc ccc ctg aag atc cac gag tgc aac atc agc      384
Cys Lys Phe Thr Leu Pro Pro Leu Lys Ile His Glu Cys Asn Ile Ser
        115                 120                 125 tgc ccc aac ccc ctg ccc ttc cgg gag tac cgg ccc cag acc gag ggc      432
Cys Pro Asn Pro Leu Pro Phe Arg Glu Tyr Arg Pro Gln Thr Glu Gly
    130                 135                 140 gtg agc aac ctg gtc ggc ctg ccc aac aac atc tgc ctg cag aaa acc      480
Val Ser Asn Leu Val Gly Leu Pro Asn Asn Ile Cys Leu Gln Lys Thr
145                 150                 155                 160 agc aac cag atc ctg aag ccc aag ctc att tcc tac acc ctg ccc gtg      528
Ser Asn Gln Ile Leu Lys Pro Lys Leu Ile Ser Tyr Thr Leu Pro Val
                165                 170                 175 gtg ggc cag agc ggc acc tgc atc acc gac ccc ctg ctg gcc atg gac      576
Val Gly Gln Ser Gly Thr Cys Ile Thr Asp Pro Leu Leu Ala Met Asp
            180                 185                 190 gag ggc tac ttc gcc tac agc cac ctg gaa cgg atc ggc agc tgc agc      624
Glu Gly Tyr Phe Ala Tyr Ser His Leu Glu Arg Ile Gly Ser Cys Ser
        195                 200                 205 agg ggc gtg tcc aag cag cgg atc atc ggc gtg ggc gag gtg ctg gac      672
Arg Gly Val Ser Lys Gln Arg Ile Ile Gly Val Gly Glu Val Leu Asp
    210                 215                 220 cgg ggc gac gag gtg ccc agc ctg ttc atg acc aac gtg tgg acc ccc      720
Arg Gly Asp Glu Val Pro Ser Leu Phe Met Thr Asn Val Trp Thr Pro
225                 230                 235                 240 ccc aac ccc aac acc gtg tac cac tgc agc gcc gtg tac aac aac gag      768
Pro Asn Pro Asn Thr Val Tyr His Cys Ser Ala Val Tyr Asn Asn Glu
                245                 250                 255 ttc tac tac gtg ctg tgc gcc gtg agc acc gtg ggc gac ccc atc ctg      816
Phe Tyr Tyr Val Leu Cys Ala Val Ser Thr Val Gly Asp Pro Ile Leu
            260                 265                 270 aac agc acc tac tgg tcc ggc agc ctg atg atg acc cgg ctg gcc gtg      864
Asn Ser Thr Tyr Trp Ser Gly Ser Leu Met Met Thr Arg Leu Ala Val
        275                 280                 285 aag cct aag agc aat ggc ggc gga tac aac cag cac cag ctg gcc ctg      912
Lys Pro Lys Ser Asn Gly Gly Gly Tyr Asn Gln His Gln Leu Ala Leu
    290                 295                 300 cgg agc atc gag aag ggc aga tac gac aaa gtg atg ccc tac ggc ccc      960
Arg Ser Ile Glu Lys Gly Arg Tyr Asp Lys Val Met Pro Tyr Gly Pro
305                 310                 315                 320 agc ggc atc aag cag ggc gac aca ctg tac ttc ccc gcc gtg ggc ttc     1008
Ser Gly Ile Lys Gln Gly Asp Thr Leu Tyr Phe Pro Ala Val Gly Phe
                325                 330                 335 ctg gtc cgg acc gag ttc aag tac aac gac agc aac tgc ccc atc acc     1056
Leu Val Arg Thr Glu Phe Lys Tyr Asn Asp Ser Asn Cys Pro Ile Thr
            340                 345                 350 aag tgc cag tac agc aag ccc gag aac tgc aga ctg agc atg ggc atc     1104
```

|     |     |     |     |     |     |     |     |     |     |     |     |     |     |     |      |
|-----|-----|-----|-----|-----|-----|-----|-----|-----|-----|-----|-----|-----|-----|-----|------|
| Lys | Cys | Gln | Tyr | Ser | Lys | Pro | Glu | Asn | Cys | Arg | Leu | Ser | Met | Gly | Ile  |
|     |     |     |     | 355 |     |     |     | 360 |     |     |     | 365 |     |     |      |

```
cgg ccc aac agc cac tac atc ctg cgg agc ggc ctg ctg aag tac aac      1152
Arg Pro Asn Ser His Tyr Ile Leu Arg Ser Gly Leu Leu Lys Tyr Asn
        370                 375                 380 ctg agc gac ggc gag aac ccc aaa gtc gtc ttt att gag atc agc gac      1200
Leu Ser Asp Gly Glu Asn Pro Lys Val Val Phe Ile Glu Ile Ser Asp
385                 390                 395                 400 cag cgg ctg tcc atc ggc agc ccc agc aag atc tac gac agc ctg ggc      1248
Gln Arg Leu Ser Ile Gly Ser Pro Ser Lys Ile Tyr Asp Ser Leu Gly
                    405                 410                 415 cag ccc gtg ttc tac cag gcc agc ttc agc tgg gac acc atg atc aag      1296
Gln Pro Val Phe Tyr Gln Ala Ser Phe Ser Trp Asp Thr Met Ile Lys
                420                 425                 430 ttc ggc gac gtg ctg acc gtg aac ccc ctg gtg gtg aac tgg cgg aac      1344
Phe Gly Asp Val Leu Thr Val Asn Pro Leu Val Val Asn Trp Arg Asn
            435                 440                 445 aat acc gtg atc agc aga ccc ggc cag agc cag tgc ccc cgg ttc aac      1392
Asn Thr Val Ile Ser Arg Pro Gly Gln Ser Gln Cys Pro Arg Phe Asn
450                 455                 460 acc tgc ccc gcg atc tgc gcg gag ggc gtg tac aac gac gcc ttc ctg      1440
Thr Cys Pro Ala Ile Cys Ala Glu Gly Val Tyr Asn Asp Ala Phe Leu
465                 470                 475                 480 atc gac cgg atc aac tgg atc tct gcc ggc gtg ttc ctg gac tcc aac      1488
Ile Asp Arg Ile Asn Trp Ile Ser Ala Gly Val Phe Leu Asp Ser Asn
                    485                 490                 495 gcg acc gcc gcg aat ccc gtg ttc acc gtg ttt aag gac aac gag atc      1536
Ala Thr Ala Ala Asn Pro Val Phe Thr Val Phe Lys Asp Asn Glu Ile
                500                 505                 510 ctg tac cgg gcc cag ctg gcc agc gag gac acc aac gcc cag aaa acc      1584
Leu Tyr Arg Ala Gln Leu Ala Ser Glu Asp Thr Asn Ala Gln Lys Thr
            515                 520                 525 atc acc aac tgc ttt ctg ctg aag aac aag atc tgg tgc atc agc ctg      1632
Ile Thr Asn Cys Phe Leu Leu Lys Asn Lys Ile Trp Cys Ile Ser Leu
530                 535                 540 gtg gag atc tac gat acc ggc gac aac gtg atc agg ccc aag ctg ttc      1680
Val Glu Ile Tyr Asp Thr Gly Asp Asn Val Ile Arg Pro Lys Leu Phe
545                 550                 555                 560 gcc gtg aag atc ccc gag cag tgc acc ggt gac ctg ggt aag aaa ctg      1728
Ala Val Lys Ile Pro Glu Gln Cys Thr Gly Asp Leu Gly Lys Lys Leu
                    565                 570                 575 ctg gaa gct gct cgt gct ggt cag gac gac gaa gtt cgt atc ctg atg      1776
Leu Glu Ala Ala Arg Ala Gly Gln Asp Asp Glu Val Arg Ile Leu Met
                580                 585                 590 gct aac ggt gct gac gtt aac gct aag gac gag tat ggt tct act ccg      1824
Ala Asn Gly Ala Asp Val Asn Ala Lys Asp Glu Tyr Gly Ser Thr Pro
            595                 600                 605 ctg cac cta gct gct act ctt ggt cac ctg gaa atc gtt gaa gtt ctg      1872
Leu His Leu Ala Ala Thr Leu Gly His Leu Glu Ile Val Glu Val Leu
610                 615                 620 ctg aag cac ggt gct gac gtt aac gct gat gac gct act ggt ctt act      1920
Leu Lys His Gly Ala Asp Val Asn Ala Asp Asp Ala Thr Gly Leu Thr
625                 630                 635                 640 ccg ctg cac ctg gct gct tgg aat ggt cac ctg gag atc gtt gaa gtt      1968
Pro Leu His Leu Ala Ala Trp Asn Gly His Leu Glu Ile Val Glu Val
                    645                 650                 655 ctg ctg aag tac ggt gct gac gtt aac gct atg gac ttt gag ggt tgg      2016
Leu Leu Lys Tyr Gly Ala Asp Val Asn Ala Met Asp Phe Glu Gly Trp
                660                 665                 670
```

-continued

| | |
|---|---|
| act ccg ctg cac ctg gct gct cat ttt ggt cac ctg gaa atc gtt gaa<br>Thr Pro Leu His Leu Ala Ala His Phe Gly His Leu Glu Ile Val Glu<br>675 680 685 | 2064 |
| gtt ctg ctg aag tac ggt gct gac gtt aac gct cag gac aaa ttc ggt<br>Val Leu Leu Lys Tyr Gly Ala Asp Val Asn Ala Gln Asp Lys Phe Gly<br>690 695 700 | 2112 |
| aag acc ccg ttc gac cta gcg atc gac aac ggt aac gag gac att gct<br>Lys Thr Pro Phe Asp Leu Ala Ile Asp Asn Gly Asn Glu Asp Ile Ala<br>705 710 715 720 | 2160 |
| gaa gtg ctg caa aaa gcg gcg aag ctt aat gcg gcc gca aga ggt tct<br>Glu Val Leu Gln Lys Ala Ala Lys Leu Asn Ala Ala Ala Arg Gly Ser<br>725 730 735 | 2208 |
| cat cac cat cac cat cac taa<br>His His His His His His<br>740 | 2229 |

<210> SEQ ID NO 8
<211> LENGTH: 742
<212> TYPE: PRT
<213> ORGANISM: Artificial Sequence
<220> FEATURE:
<223> OTHER INFORMATION: Synthetic Construct

<400> SEQUENCE: 8

Met Lys Lys Ile Asn Glu Gly Leu Leu Asp Ser Lys Ile Leu Ser Ala
1               5                   10                  15

Phe Asn Thr Val Ile Ala Leu Leu Gly Ser Ile Val Ile Ile Val Met
                20                  25                  30

Asn Ile Met Ile Ile Gln Asn Tyr Thr Arg Ser Thr Asp Asn Gln Ala
            35                  40                  45

Val Ile Lys Asp Ala Leu Gln Gly Ile Gln Gln Ile Lys Gly Leu
        50                  55                  60

Ala Asp Lys Ile Gly Thr Glu Ile Gly Pro Lys Val Ser Leu Ile Asp
65                  70                  75                  80

Thr Ser Ser Thr Ile Thr Ile Pro Ala Asn Ile Gly Leu Leu Gly Ser
                85                  90                  95

Lys Ile Ser Gln Ser Thr Ala Ser Ile Asn Glu Asn Val Asn Glu Lys
            100                 105                 110

Cys Lys Phe Thr Leu Pro Pro Leu Lys Ile His Glu Cys Asn Ile Ser
        115                 120                 125

Cys Pro Asn Pro Leu Pro Phe Arg Glu Tyr Arg Pro Gln Thr Glu Gly
    130                 135                 140

Val Ser Asn Leu Val Gly Leu Pro Asn Asn Ile Cys Leu Gln Lys Thr
145                 150                 155                 160

Ser Asn Gln Ile Leu Lys Pro Lys Leu Ile Ser Tyr Thr Leu Pro Val
                165                 170                 175

Val Gly Gln Ser Gly Thr Cys Ile Thr Asp Pro Leu Leu Ala Met Asp
            180                 185                 190

Glu Gly Tyr Phe Ala Tyr Ser His Leu Glu Arg Ile Gly Ser Cys Ser
        195                 200                 205

Arg Gly Val Ser Lys Gln Arg Ile Ile Gly Val Gly Glu Val Leu Asp
    210                 215                 220

Arg Gly Asp Glu Val Pro Ser Leu Phe Met Thr Asn Val Trp Thr Pro
225                 230                 235                 240

Pro Asn Pro Asn Thr Val Tyr His Cys Ser Ala Val Tyr Asn Asn Glu
                245                 250                 255

Phe Tyr Tyr Val Leu Cys Ala Val Ser Thr Val Gly Asp Pro Ile Leu

```
                  260                 265                 270
Asn Ser Thr Tyr Trp Ser Gly Ser Leu Met Met Thr Arg Leu Ala Val
        275                 280                 285
Lys Pro Lys Ser Asn Gly Gly Tyr Asn Gln His Gln Leu Ala Leu
290                 295                 300
Arg Ser Ile Glu Lys Gly Arg Tyr Asp Lys Val Met Pro Tyr Gly Pro
305                 310                 315                 320
Ser Gly Ile Lys Gln Gly Asp Thr Leu Tyr Phe Pro Ala Val Gly Phe
                325                 330                 335
Leu Val Arg Thr Glu Phe Lys Tyr Asn Asp Ser Asn Cys Pro Ile Thr
            340                 345                 350
Lys Cys Gln Tyr Ser Lys Pro Glu Asn Cys Arg Leu Ser Met Gly Ile
        355                 360                 365
Arg Pro Asn Ser His Tyr Ile Leu Arg Ser Gly Leu Leu Lys Tyr Asn
    370                 375                 380
Leu Ser Asp Gly Glu Asn Pro Lys Val Val Phe Ile Glu Ile Ser Asp
385                 390                 395                 400
Gln Arg Leu Ser Ile Gly Ser Pro Ser Lys Ile Tyr Asp Ser Leu Gly
                405                 410                 415
Gln Pro Val Phe Tyr Gln Ala Ser Phe Ser Trp Asp Thr Met Ile Lys
            420                 425                 430
Phe Gly Asp Val Leu Thr Val Asn Pro Leu Val Val Asn Trp Arg Asn
        435                 440                 445
Asn Thr Val Ile Ser Arg Pro Gly Gln Ser Gln Cys Pro Arg Phe Asn
    450                 455                 460
Thr Cys Pro Ala Ile Cys Ala Glu Gly Val Tyr Asn Asp Ala Phe Leu
465                 470                 475                 480
Ile Asp Arg Ile Asn Trp Ile Ser Ala Gly Val Phe Leu Asp Ser Asn
                485                 490                 495
Ala Thr Ala Ala Asn Pro Val Phe Thr Val Phe Lys Asp Asn Glu Ile
            500                 505                 510
Leu Tyr Arg Ala Gln Leu Ala Ser Glu Asp Thr Asn Ala Gln Lys Thr
        515                 520                 525
Ile Thr Asn Cys Phe Leu Leu Lys Asn Lys Ile Trp Cys Ile Ser Leu
    530                 535                 540
Val Glu Ile Tyr Asp Thr Gly Asp Asn Val Ile Arg Pro Lys Leu Phe
545                 550                 555                 560
Ala Val Lys Ile Pro Glu Gln Cys Thr Gly Asp Leu Gly Lys Lys Leu
                565                 570                 575
Leu Glu Ala Ala Arg Ala Gly Gln Asp Asp Glu Val Arg Ile Leu Met
            580                 585                 590
Ala Asn Gly Ala Asp Val Asn Ala Lys Asp Glu Tyr Gly Ser Thr Pro
        595                 600                 605
Leu His Leu Ala Ala Thr Leu Gly His Leu Glu Ile Val Glu Val Leu
    610                 615                 620
Leu Lys His Gly Ala Asp Val Asn Ala Asp Ala Thr Gly Leu Thr
625                 630                 635                 640
Pro Leu His Leu Ala Ala Trp Asn Gly His Leu Glu Ile Val Glu Val
                645                 650                 655
Leu Leu Lys Tyr Gly Ala Asp Val Asn Ala Met Asp Phe Glu Gly Trp
            660                 665                 670
Thr Pro Leu His Leu Ala Ala His Phe Gly His Leu Glu Ile Val Glu
        675                 680                 685
```

```
Val Leu Leu Lys Tyr Gly Ala Asp Val Asn Ala Gln Asp Lys Phe Gly
            690                 695                 700

Lys Thr Pro Phe Asp Leu Ala Ile Asp Asn Gly Asn Glu Asp Ile Ala
705                 710                 715                 720

Glu Val Leu Gln Lys Ala Ala Lys Leu Asn Ala Ala Arg Gly Ser
                725                 730                 735

His His His His His His
            740

<210> SEQ ID NO 9
<211> LENGTH: 602
<212> TYPE: PRT
<213> ORGANISM: Nipah virus

<400> SEQUENCE: 9

Met Pro Ala Glu Asn Lys Lys Val Arg Phe Glu Asn Thr Thr Ser Asp
1               5                   10                  15

Lys Gly Lys Ile Pro Ser Lys Val Ile Lys Ser Tyr Tyr Gly Thr Met
            20                  25                  30

Asp Ile Lys Lys Ile Asn Glu Gly Leu Leu Asp Ser Lys Ile Leu Ser
        35                  40                  45

Ala Phe Asn Thr Val Ile Ala Leu Leu Gly Ser Ile Val Ile Ile Val
50                  55                  60

Met Asn Ile Met Ile Ile Gln Asn Tyr Thr Arg Ser Thr Asp Asn Gln
65                  70                  75                  80

Ala Val Ile Lys Asp Ala Leu Gln Gly Ile Gln Gln Gln Ile Lys Gly
                85                  90                  95

Leu Ala Asp Lys Ile Gly Thr Glu Ile Gly Pro Lys Val Ser Leu Ile
            100                 105                 110

Asp Thr Ser Ser Thr Ile Thr Ile Pro Ala Asn Ile Gly Leu Leu Gly
        115                 120                 125

Ser Lys Ile Ser Gln Ser Thr Ala Ser Ile Asn Glu Asn Val Asn Glu
130                 135                 140

Lys Cys Lys Phe Thr Leu Pro Pro Leu Lys Ile His Glu Cys Asn Ile
145                 150                 155                 160

Ser Cys Pro Asn Pro Leu Pro Phe Arg Glu Tyr Arg Pro Gln Thr Glu
                165                 170                 175

Gly Val Ser Asn Leu Val Gly Leu Pro Asn Asn Ile Cys Leu Gln Lys
            180                 185                 190

Thr Ser Asn Gln Ile Leu Lys Pro Lys Leu Ile Ser Tyr Thr Leu Pro
        195                 200                 205

Val Val Gly Gln Ser Gly Thr Cys Ile Thr Asp Pro Leu Leu Ala Met
210                 215                 220

Asp Glu Gly Tyr Phe Ala Tyr Ser His Leu Glu Arg Ile Gly Ser Cys
225                 230                 235                 240

Ser Arg Gly Val Ser Lys Gln Arg Ile Ile Gly Val Gly Glu Val Leu
                245                 250                 255

Asp Arg Gly Asp Glu Val Pro Ser Leu Phe Met Thr Asn Val Trp Thr
            260                 265                 270

Pro Pro Asn Pro Asn Thr Val Tyr His Cys Ser Ala Val Tyr Asn Asn
        275                 280                 285

Glu Phe Tyr Tyr Val Leu Cys Ala Val Ser Thr Val Gly Asp Pro Ile
290                 295                 300

Leu Asn Ser Thr Tyr Trp Ser Gly Ser Leu Met Met Thr Arg Leu Ala
```

-continued

```
305                 310                 315                 320

Val Lys Pro Lys Ser Asn Gly Gly Gly Tyr Asn Gln His Gln Leu Ala
                325                 330                 335

Leu Arg Ser Ile Glu Lys Gly Arg Tyr Asp Lys Val Met Pro Tyr Gly
            340                 345                 350

Pro Ser Gly Ile Lys Gln Gly Asp Thr Leu Tyr Phe Pro Ala Val Gly
        355                 360                 365

Phe Leu Val Arg Thr Glu Phe Lys Tyr Asn Asp Ser Asn Cys Pro Ile
    370                 375                 380

Thr Lys Cys Gln Tyr Ser Lys Pro Glu Asn Cys Arg Leu Ser Met Gly
385                 390                 395                 400

Ile Arg Pro Asn Ser His Tyr Ile Leu Arg Ser Gly Leu Leu Lys Tyr
                405                 410                 415

Asn Leu Ser Asp Gly Glu Asn Pro Lys Val Val Phe Ile Glu Ile Ser
            420                 425                 430

Asp Gln Arg Leu Ser Ile Gly Ser Pro Ser Lys Ile Tyr Asp Ser Leu
        435                 440                 445

Gly Gln Pro Val Phe Tyr Gln Ala Ser Phe Ser Trp Asp Thr Met Ile
    450                 455                 460

Lys Phe Gly Asp Val Leu Thr Val Asn Pro Leu Val Val Asn Trp Arg
465                 470                 475                 480

Asn Asn Thr Val Ile Ser Arg Pro Gly Gln Ser Gln Cys Pro Arg Phe
                485                 490                 495

Asn Thr Cys Pro Glu Ile Cys Trp Glu Gly Val Tyr Asn Asp Ala Phe
            500                 505                 510

Leu Ile Asp Arg Ile Asn Trp Ile Ser Ala Gly Val Phe Leu Asp Ser
        515                 520                 525

Asn Gln Thr Ala Glu Asn Pro Val Phe Thr Val Phe Lys Asp Asn Glu
    530                 535                 540

Ile Leu Tyr Arg Ala Gln Leu Ala Ser Glu Asp Thr Asn Ala Gln Lys
545                 550                 555                 560

Thr Ile Thr Asn Cys Phe Leu Leu Lys Asn Lys Ile Trp Cys Ile Ser
                565                 570                 575

Leu Val Glu Ile Tyr Asp Thr Gly Asp Asn Val Ile Arg Pro Lys Leu
            580                 585                 590

Phe Ala Val Lys Ile Pro Glu Gln Cys Thr
        595                 600

<210> SEQ ID NO 10
<211> LENGTH: 617
<212> TYPE: PRT
<213> ORGANISM: Measles virus

<400> SEQUENCE: 10

Met Ser Pro Gln Arg Asp Arg Ile Asn Ala Phe Tyr Lys Asp Asn Pro
1               5                   10                  15

His Pro Lys Gly Ser Arg Ile Val Ile Asn Arg Glu His Leu Met Ile
            20                  25                  30

Asp Arg Pro Tyr Val Leu Leu Ala Val Leu Phe Val Met Phe Leu Ser
        35                  40                  45

Leu Ile Gly Leu Leu Ala Ile Ala Gly Ile Arg Leu His Arg Ala Ala
    50                  55                  60

Ile Tyr Thr Ala Glu Ile His Lys Ser Leu Ser Thr Asn Leu Asp Val
65                  70                  75                  80
```

```
Thr Asn Ser Ile Glu His Gln Val Lys Asp Val Leu Thr Pro Leu Phe
                85                  90                  95

Lys Ile Ile Gly Asp Glu Val Gly Leu Arg Thr Pro Gln Arg Phe Thr
            100                 105                 110

Asp Leu Val Lys Phe Ile Ser Asp Lys Ile Lys Phe Leu Asn Pro Asp
        115                 120                 125

Arg Glu Tyr Asp Phe Arg Asp Leu Thr Trp Cys Ile Asn Pro Pro Glu
    130                 135                 140

Arg Ile Lys Leu Asp Tyr Asp Gln Tyr Cys Ala Asp Val Ala Ala Glu
145                 150                 155                 160

Glu Leu Met Asn Ala Leu Val Asn Ser Thr Leu Leu Glu Thr Arg Thr
                165                 170                 175

Thr Asn Gln Phe Leu Ala Val Ser Lys Gly Asn Cys Ser Gly Pro Thr
            180                 185                 190

Thr Ile Arg Gly Gln Phe Ser Asn Met Ser Leu Ser Leu Leu Asp Leu
        195                 200                 205

Tyr Leu Gly Arg Gly Tyr Asn Val Ser Ser Ile Val Thr Met Thr Ser
    210                 215                 220

Gln Gly Met Tyr Gly Gly Thr Tyr Leu Val Glu Lys Pro Asn Leu Ser
225                 230                 235                 240

Ser Lys Arg Ser Glu Leu Ser Gln Leu Ser Met Tyr Arg Val Phe Glu
                245                 250                 255

Val Gly Val Ile Arg Asn Pro Gly Leu Gly Ala Pro Val Phe His Met
            260                 265                 270

Thr Asn Tyr Leu Glu Gln Pro Val Ser Asn Asp Leu Ser Asn Cys Met
        275                 280                 285

Val Ala Leu Gly Glu Leu Lys Leu Ala Ala Leu Cys His Gly Glu Asp
    290                 295                 300

Ser Ile Thr Ile Pro Tyr Gln Gly Ser Gly Lys Gly Val Ser Phe Gln
305                 310                 315                 320

Leu Val Lys Leu Gly Val Trp Lys Ser Pro Thr Asp Met Gln Ser Trp
                325                 330                 335

Val Pro Leu Ser Thr Asp Asp Pro Val Ile Asp Arg Leu Tyr Leu Ser
            340                 345                 350

Ser His Arg Gly Val Ile Ala Asp Asn Gln Ala Lys Trp Ala Val Pro
        355                 360                 365

Thr Thr Arg Thr Asp Asp Lys Leu Arg Met Glu Thr Cys Phe Gln Gln
    370                 375                 380

Ala Cys Lys Gly Lys Ile Gln Ala Leu Cys Glu Asn Pro Glu Trp Ala
385                 390                 395                 400

Pro Leu Lys Asp Asn Arg Ile Pro Ser Tyr Gly Val Leu Ser Val Asp
                405                 410                 415

Leu Ser Leu Thr Val Glu Leu Lys Ile Lys Ile Ala Ser Gly Phe Gly
            420                 425                 430

Pro Leu Ile Thr His Gly Ser Gly Met Asp Leu Tyr Lys Ser Asn His
        435                 440                 445

Asn Asn Val Tyr Trp Leu Thr Ile Pro Pro Met Lys Asn Leu Ala Leu
    450                 455                 460

Gly Val Ile Asn Thr Leu Glu Trp Ile Pro Arg Phe Lys Val Ser Pro
465                 470                 475                 480

Tyr Leu Phe Thr Val Pro Ile Lys Glu Ala Gly Gly Asp Cys His Ala
                485                 490                 495

Pro Thr Tyr Leu Pro Ala Glu Val Asp Gly Asp Val Lys Leu Ser Ser
```

```
              500                 505                 510
Asn Leu Val Ile Leu Pro Gly Gln Asp Leu Gln Tyr Val Leu Ala Thr
            515                 520                 525

Tyr Asp Thr Ser Arg Val Glu His Ala Val Val Tyr Val Tyr Ser
    530                 535                 540

Pro Ser Arg Ser Phe Ser Tyr Phe Tyr Pro Phe Arg Leu Pro Ile Lys
545                 550                 555                 560

Gly Val Pro Ile Glu Leu Gln Val Glu Cys Phe Thr Trp Asp Gln Lys
                565                 570                 575

Leu Trp Cys Arg His Phe Cys Val Leu Ala Asp Ser Glu Ser Gly Gly
            580                 585                 590

His Ile Thr His Ser Gly Met Val Gly Met Gly Val Ser Cys Thr Val
            595                 600                 605

Thr Arg Glu Asp Gly Thr Asn Arg Arg
    610                 615

<210> SEQ ID NO 11
<211> LENGTH: 546
<212> TYPE: PRT
<213> ORGANISM: Nipah virus

<400> SEQUENCE: 11

Met Val Val Ile Leu Asp Lys Arg Cys Tyr Cys Asn Leu Leu Ile Leu
1               5                   10                  15

Ile Leu Met Ile Ser Glu Cys Ser Val Gly Ile Leu His Tyr Glu Lys
            20                  25                  30

Leu Ser Lys Ile Gly Leu Val Lys Gly Val Thr Arg Lys Tyr Lys Ile
        35                  40                  45

Lys Ser Asn Pro Leu Thr Lys Asp Ile Val Ile Lys Met Ile Pro Asn
    50                  55                  60

Val Ser Asn Met Ser Gln Cys Thr Gly Ser Val Met Glu Asn Tyr Lys
65                  70                  75                  80

Thr Arg Leu Asn Gly Ile Leu Thr Pro Ile Lys Gly Ala Leu Glu Ile
                85                  90                  95

Tyr Lys Asn Asn Thr His Asp Leu Val Gly Asp Val Arg Leu Ala Gly
            100                 105                 110

Val Ile Met Ala Gly Val Ala Ile Gly Ile Ala Thr Ala Ala Gln Ile
        115                 120                 125

Thr Ala Gly Val Ala Leu Tyr Glu Ala Met Lys Asn Ala Asp Asn Ile
    130                 135                 140

Asn Lys Leu Lys Ser Ser Ile Glu Ser Thr Asn Glu Ala Val Val Lys
145                 150                 155                 160

Leu Gln Glu Thr Ala Glu Lys Thr Val Tyr Val Leu Thr Ala Leu Gln
                165                 170                 175

Asp Tyr Ile Asn Thr Asn Leu Val Pro Thr Ile Asp Lys Ile Ser Cys
            180                 185                 190

Lys Gln Thr Glu Leu Ser Leu Asp Leu Ala Leu Ser Lys Tyr Leu Ser
        195                 200                 205

Asp Leu Leu Phe Val Phe Gly Pro Asn Leu Gln Asp Pro Val Ser Asn
    210                 215                 220

Ser Met Thr Ile Gln Ala Ile Ser Gln Ala Phe Gly Gly Asn Tyr Glu
225                 230                 235                 240

Thr Leu Leu Arg Thr Leu Gly Tyr Ala Thr Glu Asp Phe Asp Asp Leu
                245                 250                 255
```

```
Leu Glu Ser Asp Ser Ile Thr Gly Gln Ile Ile Tyr Val Asp Leu Ser
            260                 265                 270

Ser Tyr Tyr Ile Ile Val Arg Val Tyr Phe Pro Ile Leu Thr Glu Ile
        275                 280                 285

Gln Gln Ala Tyr Ile Gln Glu Leu Leu Pro Val Ser Phe Asn Asn Asp
    290                 295                 300

Asn Ser Glu Trp Ile Ser Ile Val Pro Asn Phe Ile Leu Val Arg Asn
305                 310                 315                 320

Thr Leu Ile Ser Asn Ile Glu Ile Gly Phe Cys Leu Ile Thr Lys Arg
                325                 330                 335

Ser Val Ile Cys Asn Gln Asp Tyr Ala Thr Pro Met Thr Asn Asn Met
            340                 345                 350

Arg Glu Cys Leu Thr Gly Ser Thr Glu Lys Cys Pro Arg Glu Leu Val
        355                 360                 365

Val Ser Ser His Val Pro Arg Phe Ala Leu Ser Asn Gly Val Leu Phe
    370                 375                 380

Ala Asn Cys Ile Ser Val Thr Cys Gln Cys Gln Thr Thr Gly Arg Ala
385                 390                 395                 400

Ile Ser Gln Ser Gly Glu Gln Thr Leu Leu Met Ile Asp Asn Thr Thr
                405                 410                 415

Cys Pro Thr Ala Val Leu Gly Asn Val Ile Ile Ser Leu Gly Lys Tyr
            420                 425                 430

Leu Gly Ser Val Asn Tyr Asn Ser Glu Gly Ile Ala Ile Gly Pro Pro
        435                 440                 445

Val Phe Thr Asp Lys Val Asp Ile Ser Ser Gln Ile Ser Ser Met Asn
    450                 455                 460

Gln Ser Leu Gln Gln Ser Lys Asp Tyr Ile Lys Glu Ala Gln Arg Leu
465                 470                 475                 480

Leu Asp Thr Val Asn Pro Ser Leu Ile Ser Met Leu Ser Met Ile Ile
                485                 490                 495

Leu Tyr Val Leu Ser Ile Ala Ser Leu Cys Ile Gly Leu Ile Thr Phe
            500                 505                 510

Ile Ser Phe Ile Ile Val Glu Lys Lys Arg Asn Thr Tyr Ser Arg Leu
        515                 520                 525

Glu Asp Arg Arg Val Arg Pro Thr Ser Ser Gly Asp Leu Tyr Tyr Ile
    530                 535                 540

Gly Thr
545

<210> SEQ ID NO 12
<211> LENGTH: 553
<212> TYPE: PRT
<213> ORGANISM: Measles virus

<400> SEQUENCE: 12

Met Ser Ile Met Gly Leu Lys Val Asn Val Ser Ala Ile Phe Met Ala
1               5                   10                  15

Val Leu Leu Thr Leu Gln Thr Pro Thr Gly Gln Ile His Trp Gly Asn
            20                  25                  30

Leu Ser Lys Ile Gly Val Val Gly Ile Gly Ser Ala Ser Tyr Lys Val
        35                  40                  45

Met Thr Arg Ser Ser His Gln Ser Leu Val Ile Lys Leu Met Pro Asn
    50                  55                  60

Ile Thr Leu Leu Asn Asn Cys Thr Arg Val Glu Ile Ala Glu Tyr Arg
65                  70                  75                  80
```

-continued

```
Arg Leu Leu Arg Thr Val Leu Glu Pro Ile Arg Asp Ala Leu Asn Ala
                85                  90                  95
Met Thr Gln Asn Ile Arg Pro Val Gln Ser Val Ala Ser Ser Arg Arg
            100                 105                 110
His Lys Arg Phe Ala Gly Val Val Leu Ala Gly Ala Ala Leu Gly Val
        115                 120                 125
Ala Thr Ala Ala Gln Ile Thr Ala Gly Ile Ala Leu His Gln Ser Met
    130                 135                 140
Leu Asn Ser Gln Ala Ile Asp Asn Leu Arg Ala Ser Leu Glu Thr Thr
145                 150                 155                 160
Asn Gln Ala Ile Glu Ala Ile Arg Gln Ala Gly Gln Glu Met Ile Leu
                165                 170                 175
Ala Val Gln Gly Val Gln Asp Tyr Ile Asn Asn Glu Leu Ile Pro Ser
            180                 185                 190
Met Asn Gln Leu Ser Cys Asp Leu Ile Gly Gln Lys Leu Gly Leu Lys
        195                 200                 205
Leu Leu Arg Tyr Tyr Thr Glu Ile Leu Ser Leu Phe Gly Pro Ser Leu
    210                 215                 220
Arg Asp Pro Ile Ser Ala Glu Ile Ser Ile Gln Ala Leu Ser Tyr Ala
225                 230                 235                 240
Leu Gly Gly Asp Ile Asn Lys Val Leu Glu Lys Leu Gly Tyr Ser Gly
                245                 250                 255
Gly Asp Leu Leu Gly Ile Leu Glu Ser Arg Gly Ile Lys Ala Arg Ile
            260                 265                 270
Thr His Val Asp Thr Glu Ser Tyr Phe Ile Val Leu Ser Ile Ala Tyr
        275                 280                 285
Pro Thr Leu Ser Glu Ile Lys Gly Val Ile Val His Arg Leu Glu Gly
    290                 295                 300
Val Ser Tyr Asn Ile Gly Ser Gln Glu Trp Tyr Thr Thr Val Pro Lys
305                 310                 315                 320
Tyr Val Ala Thr Gln Gly Tyr Leu Ile Ser Asn Phe Asp Glu Ser Ser
                325                 330                 335
Cys Thr Phe Met Pro Glu Gly Thr Val Cys Ser Gln Asn Ala Leu Tyr
            340                 345                 350
Pro Met Ser Pro Leu Leu Gln Glu Cys Leu Arg Gly Ser Thr Lys Ser
        355                 360                 365
Cys Ala Arg Thr Leu Val Ser Gly Ser Phe Gly Asn Arg Phe Ile Leu
    370                 375                 380
Ser Gln Gly Asn Leu Ile Ala Asn Cys Ala Ser Ile Leu Cys Lys Cys
385                 390                 395                 400
Tyr Thr Thr Gly Thr Ile Ile Asn Gln Asp Pro Asp Lys Ile Leu Thr
                405                 410                 415
Tyr Ile Ala Ala Asp His Cys Pro Val Val Glu Val Asn Gly Val Thr
            420                 425                 430
Ile Gln Val Gly Ser Arg Arg Tyr Pro Asp Ala Val Tyr Leu His Arg
        435                 440                 445
Ile Asp Leu Gly Pro Pro Ile Ser Leu Glu Arg Leu Asp Val Gly Thr
    450                 455                 460
Asn Leu Gly Asn Ala Ile Ala Lys Leu Glu Asp Ala Lys Glu Leu Leu
465                 470                 475                 480
Glu Ser Ser Asp Gln Ile Leu Arg Ser Met Lys Gly Leu Ser Ser Thr
                485                 490                 495
```

```
Ser Ile Val Tyr Ile Leu Ile Ala Val Cys Leu Gly Gly Leu Ile Gly
                500                 505                 510

Ile Pro Ala Leu Ile Cys Cys Cys Arg Gly Arg Cys Asn Lys Lys Gly
            515                 520                 525

Glu Gln Val Gly Met Ser Arg Pro Gly Leu Lys Pro Asp Leu Thr Gly
        530                 535                 540

Thr Ser Lys Ser Tyr Val Arg Ser Leu
545                 550

<210> SEQ ID NO 13
<211> LENGTH: 2328
<212> TYPE: DNA
<213> ORGANISM: Artificial Sequence
<220> FEATURE:
<223> OTHER INFORMATION: Truncated and mutated (Y481A, R533A, S548L,
      F549S) MeV H protein (Hcdelta15) fused to IL-17
<220> FEATURE:
<221> NAME/KEY: CDS
<222> LOCATION: (1)..(2328)

<400> SEQUENCE: 13 atg cat ccc aag gga agt agg ata gtc att aac aga gaa cat ctt atg      48
Met His Pro Lys Gly Ser Arg Ile Val Ile Asn Arg Glu His Leu Met
1               5                   10                  15 att gat aga cct tat gtt ttg ctg gct gtt ctg ttt gtc atg ttt ctg      96
Ile Asp Arg Pro Tyr Val Leu Leu Ala Val Leu Phe Val Met Phe Leu
                20                  25                  30 agc ttg atc ggg ttg cta gcc att gca ggc att aga ctt cat cgg gca     144
Ser Leu Ile Gly Leu Leu Ala Ile Ala Gly Ile Arg Leu His Arg Ala
            35                  40                  45 gcc atc tac acc gca gag atc cat aaa agc ctc agc acc aat cta gat     192
Ala Ile Tyr Thr Ala Glu Ile His Lys Ser Leu Ser Thr Asn Leu Asp
        50                  55                  60 gta act aac tca atc gag cat cag gtc aag gac gtg ctg aca cca ctc     240
Val Thr Asn Ser Ile Glu His Gln Val Lys Asp Val Leu Thr Pro Leu
65                  70                  75                  80 ttc aaa atc atc ggt gat gaa gtg ggc ctg agg aca cct cag aga ttc     288
Phe Lys Ile Ile Gly Asp Glu Val Gly Leu Arg Thr Pro Gln Arg Phe
                85                  90                  95 act gac cta gtg aaa ttc atc tct gac aag att aaa ttc ctt aat ccg     336
Thr Asp Leu Val Lys Phe Ile Ser Asp Lys Ile Lys Phe Leu Asn Pro
                100                 105                 110 gat agg gag tac gac ttc aga gat ctc act tgg tgt atc aac ccg cca     384
Asp Arg Glu Tyr Asp Phe Arg Asp Leu Thr Trp Cys Ile Asn Pro Pro
            115                 120                 125 gag aga atc aaa ttg gat tat gat caa tac tgt gca gat gtg gct gct     432
Glu Arg Ile Lys Leu Asp Tyr Asp Gln Tyr Cys Ala Asp Val Ala Ala
        130                 135                 140 gaa gag ctc atg aat gca ttg gtg aac tca act cta ctg gag acc aga     480
Glu Glu Leu Met Asn Ala Leu Val Asn Ser Thr Leu Leu Glu Thr Arg
145                 150                 155                 160 aca acc aat cag ttc cta gct gtc tca aag gga aac tgc tca ggg ccc     528
Thr Thr Asn Gln Phe Leu Ala Val Ser Lys Gly Asn Cys Ser Gly Pro
                165                 170                 175 act aca atc aga ggt caa ttc tca aac atg tcg ctg tcc ctg tta gac     576
Thr Thr Ile Arg Gly Gln Phe Ser Asn Met Ser Leu Ser Leu Leu Asp
                180                 185                 190 ttg tat tta ggt cga ggt tac aat gtg tca tct ata gtc act atg aca     624
Leu Tyr Leu Gly Arg Gly Tyr Asn Val Ser Ser Ile Val Thr Met Thr
            195                 200                 205 tcc cag gga atg tat ggg gga act tac cta gtg gaa aag cct aat ctg     672
```

```
          Ser Gln Gly Met Tyr Gly Gly Thr Tyr Leu Val Glu Lys Pro Asn Leu
              210             215                 220 agc agc aaa agg tca gag ttg tca caa ctg agc atg tac cga gtg ttt       720
Ser Ser Lys Arg Ser Glu Leu Ser Gln Leu Ser Met Tyr Arg Val Phe
225             230                 235                 240 gaa gta ggt gtt atc aga aat ccg ggt ttg ggg gct ccg gtg ttc cat       768
Glu Val Gly Val Ile Arg Asn Pro Gly Leu Gly Ala Pro Val Phe His
                245                 250                 255 atg aca aac tat ctt gag caa cca gtc agt aat gat ctc agc aac tgt       816
Met Thr Asn Tyr Leu Glu Gln Pro Val Ser Asn Asp Leu Ser Asn Cys
                260                 265                 270 atg gtg gct ttg ggg gag ctc aaa ctc gca gcc ctt tgt cac ggg gaa       864
Met Val Ala Leu Gly Glu Leu Lys Leu Ala Ala Leu Cys His Gly Glu
            275                 280                 285 gat tct atc aca att ccc tat cag gga tca ggg aaa ggt gtc agc ttc       912
Asp Ser Ile Thr Ile Pro Tyr Gln Gly Ser Gly Lys Gly Val Ser Phe
        290                 295                 300 cag ctc gtc aag cta ggt gtc tgg aaa tcc cca acc gac atg caa tcc       960
Gln Leu Val Lys Leu Gly Val Trp Lys Ser Pro Thr Asp Met Gln Ser
305             310                 315                 320 tgg gtc ccc tta tca acg gat gat cca gtg ata gac agg ctt tac ctc      1008
Trp Val Pro Leu Ser Thr Asp Asp Pro Val Ile Asp Arg Leu Tyr Leu
                325                 330                 335 tca tct cac aga ggt gtt atc gct gac aat caa gca aaa tgg gct gtc      1056
Ser Ser His Arg Gly Val Ile Ala Asp Asn Gln Ala Lys Trp Ala Val
                340                 345                 350 ccg aca aca cga aca gat gac aag ttg cga atg gag aca tgc ttc caa      1104
Pro Thr Thr Arg Thr Asp Asp Lys Leu Arg Met Glu Thr Cys Phe Gln
            355                 360                 365 cag gcg tgt aag ggt aaa atc caa gca ctc tgc gag aat ccc gag tgg      1152
Gln Ala Cys Lys Gly Lys Ile Gln Ala Leu Cys Glu Asn Pro Glu Trp
        370                 375                 380 gca cca ttg aag gat aac agg att cct tca tac ggg gtc ttg tct gtt      1200
Ala Pro Leu Lys Asp Asn Arg Ile Pro Ser Tyr Gly Val Leu Ser Val
385             390                 395                 400 gat ctg agt ctg aca gtt gag ctt aaa atc aaa att gct tcg gga ttc      1248
Asp Leu Ser Leu Thr Val Glu Leu Lys Ile Lys Ile Ala Ser Gly Phe
                405                 410                 415 ggg cca ttg atc aca cac ggt tca ggg atg gac cta tac aaa tcc aac      1296
Gly Pro Leu Ile Thr His Gly Ser Gly Met Asp Leu Tyr Lys Ser Asn
                420                 425                 430 cac aac aat gtg tat tgg ctg act atc ccg cca atg aag aac cta gcc      1344
His Asn Asn Val Tyr Trp Leu Thr Ile Pro Pro Met Lys Asn Leu Ala
            435                 440                 445 tta ggt gta atc aac aca ttg gag tgg ata ccg aga ttc aag gtt agt      1392
Leu Gly Val Ile Asn Thr Leu Glu Trp Ile Pro Arg Phe Lys Val Ser
        450                 455                 460 ccc gcg ctc ttc aat gtc cca att aag gaa gca ggc gaa gac tgc cat      1440
Pro Ala Leu Phe Asn Val Pro Ile Lys Glu Ala Gly Glu Asp Cys His
465             470                 475                 480 gcc cca aca tac cta cct gcg gag gtg gat ggt gat gtc aaa ctc agt      1488
Ala Pro Thr Tyr Leu Pro Ala Glu Val Asp Gly Asp Val Lys Leu Ser
                485                 490                 495 tcc aat ctg gtg att cta cct ggt caa gat ctc caa tat gtt ttg gca      1536
Ser Asn Leu Val Ile Leu Pro Gly Gln Asp Leu Gln Tyr Val Leu Ala
                500                 505                 510 acc tac gat act tcc gcg gtt gaa cat gct gtg gtt tat tac gtt tac      1584
Thr Tyr Asp Thr Ser Ala Val Glu His Ala Val Val Tyr Tyr Val Tyr
            515                 520                 525
```

```
agc cca agc cgc tca ttt tct tac ttt tat cct ttt agg ttg cct ata    1632
Ser Pro Ser Arg Ser Phe Ser Tyr Phe Tyr Pro Phe Arg Leu Pro Ile
    530                 535                 540 aag ggg gtc ccc atc gaa tta caa gtg gaa tgc ttc aca tgg gac caa    1680
Lys Gly Val Pro Ile Glu Leu Gln Val Glu Cys Phe Thr Trp Asp Gln
545                 550                 555                 560 aaa ctc tgg tgc cgt cac ttc tgt gtg ctt gcg gac tca gaa tct ggt    1728
Lys Leu Trp Cys Arg His Phe Cys Val Leu Ala Asp Ser Glu Ser Gly
                565                 570                 575 gga cat atc act cac tct ggg atg gag ggc atg gga gtc agc tgc aca    1776
Gly His Ile Thr His Ser Gly Met Glu Gly Met Gly Val Ser Cys Thr
    580                 585                 590 gtc acc cgg gaa gat gga acc aat atc gag gga agg gcg gcc cag ccg    1824
Val Thr Arg Glu Asp Gly Thr Asn Ile Glu Gly Arg Ala Ala Gln Pro
595                 600                 605 gcc atg gcc gat tgt gat att gaa ggt aaa gat ggc aaa caa tat gag    1872
Ala Met Ala Asp Cys Asp Ile Glu Gly Lys Asp Gly Lys Gln Tyr Glu
    610                 615                 620 agt gtt cta atg gtc agc atc gat caa tta ttg gac agc atg aaa gaa    1920
Ser Val Leu Met Val Ser Ile Asp Gln Leu Leu Asp Ser Met Lys Glu
625                 630                 635                 640 att ggt agc aat tgc ctg aat aat gaa ttt aac ttt ttt aaa aga cat    1968
Ile Gly Ser Asn Cys Leu Asn Asn Glu Phe Asn Phe Phe Lys Arg His
                645                 650                 655 atc tgt gat gct aat aag gaa ggt atg ttt tta ttc cgt gct gct cgc    2016
Ile Cys Asp Ala Asn Lys Glu Gly Met Phe Leu Phe Arg Ala Ala Arg
                    660                 665                 670 aag ttg agg caa ttt ctt aaa atg aat agc act ggt gat ttt gat ctc    2064
Lys Leu Arg Gln Phe Leu Lys Met Asn Ser Thr Gly Asp Phe Asp Leu
                675                 680                 685 cac tta tta aaa gtt tca gaa ggc aca aca ata ctg ttg aac tgc act    2112
His Leu Leu Lys Val Ser Glu Gly Thr Thr Ile Leu Leu Asn Cys Thr
    690                 695                 700 ggc cag gtt aaa gga aga aaa cca gct gcc ctg ggt gaa gcc caa cca    2160
Gly Gln Val Lys Gly Arg Lys Pro Ala Ala Leu Gly Glu Ala Gln Pro
705                 710                 715                 720 aca aag agt ttg gaa gaa aat aaa tct tta aag gaa cag aaa aaa ctg    2208
Thr Lys Ser Leu Glu Glu Asn Lys Ser Leu Lys Glu Gln Lys Lys Leu
                725                 730                 735 aat gac ttg tgt ttc cta aag aga cta tta caa gag ata aaa act tgt    2256
Asn Asp Leu Cys Phe Leu Lys Arg Leu Leu Gln Glu Ile Lys Thr Cys
                740                 745                 750 tgg aat aaa att ttg atg ggc act aaa gaa cac gcg gcc gca aga gga    2304
Trp Asn Lys Ile Leu Met Gly Thr Lys Glu His Ala Ala Ala Arg Gly
                755                 760                 765 tcg cat cac cat cac cat cac tga                                    2328
Ser His His His His His His
    770                 775

<210> SEQ ID NO 14
<211> LENGTH: 775
<212> TYPE: PRT
<213> ORGANISM: Artificial Sequence
<220> FEATURE:
<223> OTHER INFORMATION: Synthetic Construct

<400> SEQUENCE: 14

Met His Pro Lys Gly Ser Arg Ile Val Ile Asn Arg Glu His Leu Met
1               5                   10                  15

Ile Asp Arg Pro Tyr Val Leu Leu Ala Val Leu Phe Val Met Phe Leu
            20                  25                  30
```

```
Ser Leu Ile Gly Leu Leu Ala Ile Ala Gly Ile Arg Leu His Arg Ala
        35                  40                  45

Ala Ile Tyr Thr Ala Glu Ile His Lys Ser Leu Ser Thr Asn Leu Asp
50                  55                  60

Val Thr Asn Ser Ile Glu His Gln Val Lys Asp Val Leu Thr Pro Leu
65                  70                  75                  80

Phe Lys Ile Ile Gly Asp Glu Val Gly Leu Arg Thr Pro Gln Arg Phe
                85                  90                  95

Thr Asp Leu Val Lys Phe Ile Ser Asp Lys Ile Lys Phe Leu Asn Pro
                100                 105                 110

Asp Arg Glu Tyr Asp Phe Arg Asp Leu Thr Trp Cys Ile Asn Pro Pro
        115                 120                 125

Glu Arg Ile Lys Leu Asp Tyr Asp Gln Tyr Cys Ala Asp Val Ala Ala
        130                 135                 140

Glu Glu Leu Met Asn Ala Leu Val Asn Ser Thr Leu Glu Thr Arg
145                 150                 155                 160

Thr Thr Asn Gln Phe Leu Ala Val Ser Lys Gly Asn Cys Ser Gly Pro
                165                 170                 175

Thr Thr Ile Arg Gly Gln Phe Ser Asn Met Ser Leu Ser Leu Leu Asp
        180                 185                 190

Leu Tyr Leu Gly Arg Gly Tyr Asn Val Ser Ser Ile Val Thr Met Thr
        195                 200                 205

Ser Gln Gly Met Tyr Gly Gly Thr Tyr Leu Val Glu Lys Pro Asn Leu
        210                 215                 220

Ser Ser Lys Arg Ser Glu Leu Ser Gln Leu Ser Met Tyr Arg Val Phe
225                 230                 235                 240

Glu Val Gly Val Ile Arg Asn Pro Gly Leu Gly Ala Pro Val Phe His
                245                 250                 255

Met Thr Asn Tyr Leu Glu Gln Pro Val Ser Asn Asp Leu Ser Asn Cys
            260                 265                 270

Met Val Ala Leu Gly Glu Leu Lys Leu Ala Ala Leu Cys His Gly Glu
        275                 280                 285

Asp Ser Ile Thr Ile Pro Tyr Gln Gly Ser Gly Lys Gly Val Ser Phe
        290                 295                 300

Gln Leu Val Lys Leu Gly Val Trp Lys Ser Pro Thr Asp Met Gln Ser
305                 310                 315                 320

Trp Val Pro Leu Ser Thr Asp Asp Pro Val Ile Asp Arg Leu Tyr Leu
                325                 330                 335

Ser Ser His Arg Gly Val Ile Ala Asp Asn Gln Ala Lys Trp Ala Val
        340                 345                 350

Pro Thr Thr Arg Thr Asp Asp Lys Leu Arg Met Glu Thr Cys Phe Gln
        355                 360                 365

Gln Ala Cys Lys Gly Lys Ile Gln Ala Leu Cys Glu Asn Pro Glu Trp
        370                 375                 380

Ala Pro Leu Lys Asp Asn Arg Ile Pro Ser Tyr Gly Val Leu Ser Val
385                 390                 395                 400

Asp Leu Ser Leu Thr Val Glu Leu Lys Ile Lys Ile Ala Ser Gly Phe
                405                 410                 415

Gly Pro Leu Ile Thr His Gly Ser Gly Met Asp Leu Tyr Lys Ser Asn
            420                 425                 430

His Asn Asn Val Tyr Trp Leu Thr Ile Pro Pro Met Lys Asn Leu Ala
        435                 440                 445
```

```
Leu Gly Val Ile Asn Thr Leu Glu Trp Ile Pro Arg Phe Lys Val Ser
        450                 455                 460
Pro Ala Leu Phe Asn Val Pro Ile Lys Glu Ala Gly Glu Asp Cys His
465                 470                 475                 480
Ala Pro Thr Tyr Leu Pro Ala Glu Val Asp Gly Asp Val Lys Leu Ser
                485                 490                 495
Ser Asn Leu Val Ile Leu Pro Gly Gln Asp Leu Gln Tyr Val Leu Ala
                500                 505                 510
Thr Tyr Asp Thr Ser Ala Val Glu His Ala Val Val Tyr Tyr Val Tyr
            515                 520                 525
Ser Pro Ser Arg Ser Phe Ser Tyr Phe Tyr Pro Phe Arg Leu Pro Ile
530                 535                 540
Lys Gly Val Pro Ile Glu Leu Gln Val Glu Cys Phe Thr Trp Asp Gln
545                 550                 555                 560
Lys Leu Trp Cys Arg His Phe Cys Val Leu Ala Asp Ser Glu Ser Gly
                565                 570                 575
Gly His Ile Thr His Ser Gly Met Glu Gly Met Gly Val Ser Cys Thr
                580                 585                 590
Val Thr Arg Glu Asp Gly Thr Asn Ile Glu Gly Arg Ala Ala Gln Pro
            595                 600                 605
Ala Met Ala Asp Cys Asp Ile Glu Gly Lys Asp Gly Lys Gln Tyr Glu
        610                 615                 620
Ser Val Leu Met Val Ser Ile Asp Gln Leu Leu Asp Ser Met Lys Glu
625                 630                 635                 640
Ile Gly Ser Asn Cys Leu Asn Asn Glu Phe Asn Phe Phe Lys Arg His
                645                 650                 655
Ile Cys Asp Ala Asn Lys Glu Gly Met Phe Leu Phe Arg Ala Ala Arg
                660                 665                 670
Lys Leu Arg Gln Phe Leu Lys Met Asn Ser Thr Gly Asp Phe Asp Leu
            675                 680                 685
His Leu Leu Lys Val Ser Glu Gly Thr Thr Ile Leu Leu Asn Cys Thr
        690                 695                 700
Gly Gln Val Lys Gly Arg Lys Pro Ala Ala Leu Gly Glu Ala Gln Pro
705                 710                 715                 720
Thr Lys Ser Leu Glu Glu Asn Lys Ser Leu Lys Glu Gln Lys Lys Leu
                725                 730                 735
Asn Asp Leu Cys Phe Leu Lys Arg Leu Leu Gln Glu Ile Lys Thr Cys
                740                 745                 750
Trp Asn Lys Ile Leu Met Gly Thr Lys Glu His Ala Ala Ala Arg Gly
            755                 760                 765
Ser His His His His His His
    770                 775

<210> SEQ ID NO 15
<211> LENGTH: 523
<212> TYPE: PRT
<213> ORGANISM: Artificial Sequence
<220> FEATURE:
<223> OTHER INFORMATION: Truncated MeV fusion glycoprotein (FcDelta30)

<400> SEQUENCE: 15

Met Ser Ile Met Gly Leu Lys Val Asn Val Ser Ala Ile Phe Met Ala
1               5                   10                  15
Val Leu Leu Thr Leu Gln Thr Pro Thr Gly Gln Ile His Trp Gly Asn
            20                  25                  30
```

```
Leu Ser Lys Ile Gly Val Val Gly Ile Gly Ser Ala Ser Tyr Lys Val
         35                  40                  45

Met Thr Arg Ser Ser His Gln Ser Leu Val Ile Lys Leu Met Pro Asn
 50                  55                  60

Ile Thr Leu Leu Asn Asn Cys Thr Arg Val Glu Ile Ala Glu Tyr Arg
 65                  70                  75                  80

Arg Leu Leu Arg Thr Val Leu Glu Pro Ile Arg Asp Ala Leu Asn Ala
                 85                  90                  95

Met Thr Gln Asn Ile Arg Pro Val Gln Ser Val Ala Ser Arg Arg
             100                 105                 110

His Lys Arg Phe Ala Gly Val Val Leu Ala Gly Ala Ala Leu Gly Val
         115                 120                 125

Ala Thr Ala Ala Gln Ile Thr Ala Gly Ile Ala Leu His Gln Ser Met
 130                 135                 140

Leu Asn Ser Gln Ala Ile Asp Asn Leu Arg Ala Ser Leu Glu Thr Thr
 145                 150                 155                 160

Asn Gln Ala Ile Glu Ala Ile Arg Gln Ala Gly Gln Glu Met Ile Leu
                 165                 170                 175

Ala Val Gln Gly Val Gln Asp Tyr Ile Asn Asn Glu Leu Ile Pro Ser
             180                 185                 190

Met Asn Gln Leu Ser Cys Asp Leu Ile Gly Gln Lys Leu Gly Leu Lys
         195                 200                 205

Leu Leu Arg Tyr Tyr Thr Glu Ile Leu Ser Leu Phe Gly Pro Ser Leu
         210                 215                 220

Arg Asp Pro Ile Ser Ala Glu Ile Ser Ile Gln Ala Leu Ser Tyr Ala
225                 230                 235                 240

Leu Gly Gly Asp Ile Asn Lys Val Leu Glu Lys Leu Gly Tyr Ser Gly
                 245                 250                 255

Gly Asp Leu Leu Gly Ile Leu Glu Ser Arg Gly Ile Lys Ala Arg Ile
             260                 265                 270

Thr His Val Asp Thr Glu Ser Tyr Phe Ile Val Leu Ser Ile Ala Tyr
         275                 280                 285

Pro Thr Leu Ser Glu Ile Lys Gly Val Ile Val His Arg Leu Glu Gly
 290                 295                 300

Val Ser Tyr Asn Ile Gly Ser Gln Glu Trp Tyr Thr Thr Val Pro Lys
305                 310                 315                 320

Tyr Val Ala Thr Gln Gly Tyr Leu Ile Ser Asn Phe Asp Glu Ser Ser
                 325                 330                 335

Cys Thr Phe Met Pro Glu Gly Thr Val Cys Ser Gln Asn Ala Leu Tyr
             340                 345                 350

Pro Met Ser Pro Leu Leu Gln Glu Cys Leu Arg Gly Ser Thr Lys Ser
         355                 360                 365

Cys Ala Arg Thr Leu Val Ser Gly Ser Phe Gly Asn Arg Phe Ile Leu
         370                 375                 380

Ser Gln Gly Asn Leu Ile Ala Asn Cys Ala Ser Ile Leu Cys Lys Cys
385                 390                 395                 400

Tyr Thr Thr Gly Thr Ile Ile Asn Gln Asp Pro Asp Lys Ile Leu Thr
                 405                 410                 415

Tyr Ile Ala Ala Asp His Cys Pro Val Val Glu Val Asn Gly Val Thr
             420                 425                 430

Ile Gln Val Gly Ser Arg Arg Tyr Pro Asp Ala Val Tyr Leu His Arg
         435                 440                 445

Ile Asp Leu Gly Pro Pro Ile Ser Leu Glu Arg Leu Asp Val Gly Thr
```

```
            450                 455                 460
Asn Leu Gly Asn Ala Ile Ala Lys Leu Glu Asp Ala Lys Glu Leu Leu
465                 470                 475                 480

Glu Ser Ser Asp Gln Ile Leu Arg Ser Met Lys Gly Leu Ser Ser Thr
                485                 490                 495

Ser Ile Val Tyr Ile Leu Ile Ala Val Cys Leu Gly Gly Leu Ile Gly
                500                 505                 510

Ile Pro Ala Leu Ile Cys Cys Cys Arg Gly Arg
            515                 520

<210> SEQ ID NO 16
<211> LENGTH: 524
<212> TYPE: PRT
<213> ORGANISM: Artificial Sequence
<220> FEATURE:
<223> OTHER INFORMATION: Truncated NiV fusion glycoprotein (FcDelta22)

<400> SEQUENCE: 16

Met Val Val Ile Leu Asp Lys Arg Cys Tyr Cys Asn Leu Leu Ile Leu
1               5                   10                  15

Ile Leu Met Ile Ser Glu Cys Ser Val Gly Ile Leu His Tyr Glu Lys
                20                  25                  30

Leu Ser Lys Ile Gly Leu Val Lys Gly Val Thr Arg Lys Tyr Lys Ile
            35                  40                  45

Lys Ser Asn Pro Leu Thr Lys Asp Ile Val Ile Lys Met Ile Pro Asn
        50                  55                  60

Val Ser Asn Met Ser Gln Cys Thr Gly Ser Val Met Glu Asn Tyr Lys
65                  70                  75                  80

Thr Arg Leu Asn Gly Ile Leu Thr Pro Ile Lys Gly Ala Leu Glu Ile
                85                  90                  95

Tyr Lys Asn Asn Thr His Asp Leu Val Gly Asp Val Arg Leu Ala Gly
                100                 105                 110

Val Ile Met Ala Gly Val Ala Ile Gly Ile Ala Thr Ala Ala Gln Ile
            115                 120                 125

Thr Ala Gly Val Ala Leu Tyr Glu Ala Met Lys Asn Ala Asp Asn Ile
        130                 135                 140

Asn Lys Leu Lys Ser Ser Ile Glu Ser Thr Asn Glu Ala Val Val Lys
145                 150                 155                 160

Leu Gln Glu Thr Ala Glu Lys Thr Val Tyr Val Leu Thr Ala Leu Gln
                165                 170                 175

Asp Tyr Ile Asn Thr Asn Leu Val Pro Thr Ile Asp Lys Ile Ser Cys
            180                 185                 190

Lys Gln Thr Glu Leu Ser Leu Asp Leu Ala Leu Ser Lys Tyr Leu Ser
        195                 200                 205

Asp Leu Leu Phe Val Phe Gly Pro Asn Leu Gln Asp Pro Val Ser Asn
    210                 215                 220

Ser Met Thr Ile Gln Ala Ile Ser Gln Ala Phe Gly Gly Asn Tyr Glu
225                 230                 235                 240

Thr Leu Leu Arg Thr Leu Gly Tyr Ala Thr Glu Asp Phe Asp Asp Leu
                245                 250                 255

Leu Glu Ser Asp Ser Ile Thr Gly Gln Ile Ile Tyr Val Asp Leu Ser
            260                 265                 270

Ser Tyr Tyr Ile Ile Val Arg Val Tyr Phe Pro Ile Leu Thr Glu Ile
        275                 280                 285

Gln Gln Ala Tyr Ile Gln Glu Leu Leu Pro Val Ser Phe Asn Asn Asp
```

```
                    290                 295                 300
Asn Ser Glu Trp Ile Ser Ile Val Pro Asn Phe Ile Leu Val Arg Asn
305                 310                 315                 320

Thr Leu Ile Ser Asn Ile Glu Ile Gly Phe Cys Leu Ile Thr Lys Arg
                325                 330                 335

Ser Val Ile Cys Asn Gln Asp Tyr Ala Thr Pro Met Thr Asn Asn Met
                340                 345                 350

Arg Glu Cys Leu Thr Gly Ser Thr Glu Lys Cys Pro Arg Glu Leu Val
            355                 360                 365

Val Ser Ser His Val Pro Arg Phe Ala Leu Ser Asn Gly Val Leu Phe
        370                 375                 380

Ala Asn Cys Ile Ser Val Thr Cys Gln Cys Gln Thr Thr Gly Arg Ala
385                 390                 395                 400

Ile Ser Gln Ser Gly Glu Gln Thr Leu Leu Met Ile Asp Asn Thr Thr
                405                 410                 415

Cys Pro Thr Ala Val Leu Gly Asn Val Ile Ile Ser Leu Gly Lys Tyr
            420                 425                 430

Leu Gly Ser Val Asn Tyr Asn Ser Glu Gly Ile Ala Ile Gly Pro Pro
        435                 440                 445

Val Phe Thr Asp Lys Val Asp Ile Ser Ser Gln Ile Ser Ser Met Asn
    450                 455                 460

Gln Ser Leu Gln Gln Ser Lys Asp Tyr Ile Lys Glu Ala Gln Arg Leu
465                 470                 475                 480

Leu Asp Thr Val Asn Pro Ser Leu Ile Ser Met Leu Ser Met Ile Ile
                485                 490                 495

Leu Tyr Val Leu Ser Ile Ala Ser Leu Cys Ile Gly Leu Ile Thr Phe
            500                 505                 510

Ile Ser Phe Ile Ile Val Glu Lys Lys Arg Asn Thr
            515                 520
```